(12) United States Patent
Wu et al.

(10) Patent No.: US 7,220,893 B1
(45) Date of Patent: May 22, 2007

(54) PLASMIDS AND METHODS FOR CONSTRUCTION OF NON-REDUNDANT, INDEXED, SATURATION, GENE-DISRUPTION PLANT AND ANIMAL LIBRARIES

(75) Inventors: Ray Wu, Ithaca, NY (US); Christine W. Wu, Long Beach, CA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 397 days.

(21) Appl. No.: 10/228,133

(22) Filed: Aug. 26, 2002

Related U.S. Application Data

(63) Continuation-in-part of application No. 09/574,038, filed on May 18, 2000, now abandoned.

(60) Provisional application No. 60/134,830, filed on May 19, 1999.

(51) Int. Cl.
*C12N 15/82* (2006.01)
*C12N 15/90* (2006.01)
*A01H 1/00* (2006.01)
*C12N 5/10* (2006.01)

(52) U.S. Cl. .................. 800/278; 435/320.1; 435/468; 800/266

(58) Field of Classification Search ............... 435/91.2, 435/320.1, 419, 468; 800/278, 295, 298, 800/291
See application file for complete search history.

(56) References Cited

U.S. PATENT DOCUMENTS

| | | | |
|---|---|---|---|
| 4,732,856 A | 3/1988 | Federoff | 435/468 |
| 5,013,658 A | 5/1991 | Dooner et al. | 435/468 |
| 5,225,341 A | 7/1993 | Yoder et al. | 435/468 |
| 5,658,772 A | 8/1997 | Odell et al. | 800/278 |
| 5,723,765 A | 3/1998 | Oliver et al. | 800/278 |
| 5,733,744 A | 3/1998 | Hamilton | 435/69.1 |
| 5,749,169 A | 5/1998 | Briggs | 47/58 |
| 5,792,924 A | 8/1998 | Yoder et al. | 800/278 |
| 5,808,034 A | 9/1998 | Bridges et al. | 536/24.1 |

FOREIGN PATENT DOCUMENTS

| | | |
|---|---|---|
| EP | 0 721 016 A2 | 7/1996 |
| EP | 0 425 004 B1 | 9/1996 |
| EP | 0 596 885 B1 | 9/1997 |

OTHER PUBLICATIONS

Walbot, V., Curr. Opin. Curr. Biol., Apr. 2000, vol. 3, pp. 103-107.*
Bancroft et al., "Transposition Pattern of the Maize Element *Ds* in *Arabidopsis Thaliana*," *Genetics* 134:1221-1229 (1993).
Feldman et al, "A Dwarf Mutant of *Arabidopsis* Generated by T-DNA Insertion Mutagenesis," *Science* 243:1351-1354 (1989).
Gorbunova et al., "Circularized *Ac/Ds* Transposons: Formation, Structure and Fate," *Genetics* 145:1161-1169 (1997).
Grevelding et al., "High Rates of *Ac/Ds* Germinal Transposition in *Arabidopsis* Suitable for Gene Isolation by Insertional Mutagenesis," *Proc. Natl. Acad. Sci. USA* 89:6085-6089 (1992).
Hehl et al., "Induced Transposition of *Ds* by a Stable *Ac* in Crosses of Transgenic Tobacco Plants," *Mol. Gen. Genet.* 217:53-59 (1989).
Spiker et al., "Nuclear Matrix Attachment Regions and Transgene Expression in Plants," *Plant Physiol.* 110:15-21 (1996).
Hirochika et al., "Retrotransposons of Rice Involved in Mutations Induced by Tissue Culture," *Proc. Natl. Acad. Sci. USA* 93:7783-7788 (1996).
Enoki et al., "*Ac* as a Tool for the Functional Genomics of Rice," *The Plant Journal* 19(5):605-613 (1999).
Wu, "Report of the Committee on Genetic Engineering (Functional Genomics of Plants)," *Rice Genetics Newsletter* 16:10-14 (1999).
Cao et al., Regeneration of Herbicide Resistant Transgenic Rice Plants Following Microprojectile-Mediated Transformation of Suspension Culture Cells, *Plant Cell Reports* 11:586-591 (1992).
Rommens et al., "Characterization of the *Ac/Ds* Behavior in Transgenic Tomato Plants Using Plasmid Rescue," *Plant Molecular Biology.* 20:61-70 (1992).
Sundaresan et al., "Patterns of Gene Action in Plant Development Revealed by Enhancer Trap and Gene Trap Transposable Elements," *Genes & Development* 9:1797-1810 (1995).
Liu et al., "Efficient Isolation and Mapping of *Arabidopsis Thaliana* T-DNA Insert Junctions by Thermal Asymmetric Interlaced PCR," *The Plant Journal* 8(3):457-463 (1995).
Martienssen, "Functional Genomics: Probing Plant Gene Function and Expression with Transposons," *Proc. Natl. Acad. Sci. USA* 95:2021-2026 (1998).
Wirtz et al., "Ds Excision from Extrachromosomal Geminivirus Vector DNA is Coupled to Vector DNA Replication in Maize," *The Plant Journal* 11(1):125-135 (1997).
ATA Gene, ING Systems, Stragene Catalog, p. 314 (1993).
Raz et al., "Transposition of the Nematode *Caenorhabditis elegans* Tc3 Element in the Zebrafish *Danio rerio*," *Current Biology* 8:82-88 (1998).
Fischer et al., "Regulated Transposition of a Fish Transposon in the Mouse Germ Line," *PNAS* 98(12):6759-6764 (2001).
Galiano et al., "Highly Efficient Germ-Line Transmission of Proviral Insertions in Zebrafish," *Proc. Natl. Acad. Sci. USA* 93:7777-7782 (1996).
Fadool et al., "Transposition of the *Mariner* Element from *Drosophila mauritiana* in Zebrafish," *Proc. Natl. Acad. Sci. USA* 95:5182-5186 (1998).
Liu et al., "Thermal Asymmetric Interlaced PCR: Automatable Amplification and Sequencing of Insert End Fragments from P1 and YAC Clones for Chromosome Walking," *Germomics* 25:674-681 (1995).

(Continued)

*Primary Examiner*—Ashwin Mehta
(74) *Attorney, Agent, or Firm*—Nixon Peabody LLP

(57) ABSTRACT

The present invention relates to methods of constructing non-redundant, indexed, saturation, gene-disruption genomic libraries in plants and animals. The invention also relates to gene-disruption transformation plasmids for use in the method. The present invention also relates to plants, animals, and vertebrate and invertebrate cells transformed with such plasmids.

40 Claims, 29 Drawing Sheets

OTHER PUBLICATIONS

Barnes, "PCR Amplification of Up to 35kb DNA with High Fidelity and High Yield from λ Bacteriophage Templates," *Proc. Natl. Acad. Sci. USA* 91:2216-2220 (1994).

Liu et al., "Efficient Isolation and Mapping of *Arabidopsis thaliana* T-DNA Insert Junctions by Thermal Asymmetric Interlaced PCR," *The Plant Journal* 8(3):457-463 (1995).

Wagner et al., "Cre-Mediated Gene Deletion in the Mammary Gland," *Nucleic Acids Research* 25(21):4323-4330 (1997).

Cheng et al., "Effective Amplification of Long Targets from Cloned Inserts and Human Genomic DNA," *Proc. Natl. Acad. Sci. USA* 91:5695-5699 (1994).

Gueiros-Filho et al., "Trans-Kingdom Transposition of the *Drosophila* Element *Mariner* Within the Protozoan *Leishmania*," *Science* 276:1716-1719 (1997).

Aoyama & Chua, "A Glucocorticoid-Mediated Transcriptional Induction System in Transgenic Plants," *Plant J.* 11(3):605-612 (1997).

Bensen et al., "Cloning and Characterization of the Maize *An1* Gene," *Plant Cell* 7:75-84 (1995).

Bourouis & Jarry, "Vectors Containing a Prokaryotic Dihydrofolate Reductase Gene Transform *Drosophila* Cells to Methotrexate-Resistance," *EMBO J.* 2(7):1099-1104 (1983).

Bruce et al., "Expression Profiling of the Maize Flavonoid Pathway Genes Controlled by Estradiol-Inducible Transcription Factors CRC and P," *Plant Cell* 12:65-79 (2000).

Chin et al., "Molecular Analysis of Rice Plants Harboring an *Ac/Ds* Transposable Element-Mediated Gene Trapping System," *Plant J.* 19(5):615-623 (1999).

Fraley et al., "Expression of Bacterial Genes in Plant Cells," *Proc. Natl. Acad. Sci. USA* 80:4803-4807 (1983).

Halloran et al., "Laser-Induced Gene Expression in Specific Cells of Transgenic Zebrafish," *Development* 127:1953-1960 (2000).

Holmes-Davis et al., "Nuclear Matrix Attachment Regions and Plant Gene Expressions," *Trends Plant Sci.* 3(3):91-97 (1998).

Izawa et al., "Transposon Tagging in Rice," *Plant Molecular Biology* 35:219-229 (1997).

Li et al., "Assignment of 44 Ds Insertions to the Linkage Map of *Arabidopsis*," *Plant Mol. Biol. Reporter* 17:109-122 (1999).

Liu & Wu, "Protection of Megabase-Sized Chromosomal DNA from Breakage by DNase Activity in Plant Nuclei," *BioTechniques* 26:258-261 (1999).

Luo et al., "Chromosomal Transposition of a Tc1/Mariner-Like Element in Mouse Embryonic Stem Cells," *Proc. Natl. Acad. Sci. USA* 95:10769-10773 (1998).

Ma et al., "Molecular Cloning and Characterization of GPA1, a G Protein αSubunit Gene from *Arabidopsis thaliana*," *Proc. Natl. Acad. Sci. USA* 87:3821-3825 (1990).

Machida et al., "Characterization of the Transposition Pattern of the Ac Element in *Arabidopsis thaliana* Using Endonuclease I-SceI," *Proc. Natl. Acad. Sci. USA* 94:8675-8680 (1997).

Maier-Greiner et al., "Isolation and Properties of a Nitrile Hydratase from the Soil Fungus *Myrothecium verrucaria* That is Highly Specific for the Fertilizer Cyanamide and Cloning of Its Gene," *Proc. Natl. Acad. Sci. USA* 88:4260-4264 (1991).

Muscarella et al., "Characterization of I-*Ppo*, an Intron-Encoded Endonuclease That Mediates Homing of a Group I Intron in the Ribosomal DNA of *Physarum polycephalum*," *Mol. Cell. Biol.* 10(7):3386-3396 (1990).

Odell et al., "Identification of DNA Sequences Required for Activity of the Cauliflower Mosaic Virus 35S Promoter," *Nature* 313(6005):810-812 (1985).

OW, "Recombinase-Directed Chromosome Engineering in Plants," *Curr. Opin. Biotech.* 7:181-186 (1996).

Parinov et al., "Analysis of Flanking Sequences from *Dissociation* Insertion Lines: A Database for Reverse Genetics in Arabidopsis," *Plant Cell* 11:2263-2270 (1999).

Salminen et al., "Efficient Poly A Trap Approach Allows the Capture of Genes Specifically Active in Differentiated Embryonic Stem Cell and in Mouse Embryos," *Develop. Dynamics* 212:326-333 (1998).

Schouten et al., "Transposon Tc1 of the Nematode *Caenorhabditis elegans* Jumps in Human Cells," *Nucl. Acids Res.* 26(12):3013-3017 (1998).

Shimamoto et al., "*Trans*-Activation and Stable Integration of the Maize Transposable Element *Ds* Cotransfected with the *Ac* Transposase Gene in Transgenic Rice Plants," *Mol. Gen. Genet.* 239:354-360 (1993).

Siebert et al., "An Improved PCR Method for Walking in Uncloned Genomic DNA," *Nucl. Acids Res.* 23(6):1087-1088 (1995).

Stark & Gudkov, "Forward Genetics in Mammalian Cells: Functional Approaches to Gene Discovery," *Human Mol. Genetics* 8(10):1925-1938 (1999).

Walbot, "Strategies for Mutagenesis and Gene Cloning Using Transposon Tagging and T-DNA Insertional Mutagenesis," *Annu. Rev. Plant Physiol. Plant Mol. Biol.* 43:49-82 (1992).

Weigel et al., "Activation Tagging in Arabidopsis," *Plant Physiol.* 122:1003-1013 (2000).

Yu et al., "A Draft Sequence of the Rice Genome (*Oryza sativa* L. ssp. *indica*)," *Science* 296:79-92 (2002).

Zuo et al., "An Estrogen Receptor-Based Transactivator XVE Mediates Highly Inducible Gene Expression in Transgenic Plants," *Plant J.* 24(2):265-273 (2000).

Zuo & Chua, "Chemical-Inducible Systems for Regulated Expression of Plant Genes," *Current Opin. Biotech.* 11:146-151 (2000).

Feldmann, "T-DNA Insertion Mutagenesis in Arabidopsis: Mutational Spectrum," *Plant J.* 1(1):71-82 (1991).

Fromm et al., "Expression of Genes Transferred into Monocot and Dicot Plant Cells by Electroporation," *Proc. Nat'l Acad. Sci. USA* 82:5824-5828 (1985).

Gatz et al., "Promoters that Respond to Chemical Inducers," *Trends Plant Sci.* 3(9):352-358 (1998).

Goff et al., "A Draft Sequence of the Rice Genome (Oryza sativa L. ssp. japonica)," *Science* 296:92-100 (2002).

Hiei et al., "Efficient Transformation of Rice (Oryza sativa L.) Mediated by Agrobacterium and Sequence Analysis of the Boundaries of the T-DNA," *Plant J.* 6(2):271-282 (1994).

Ju et al., "Faithful Expression of Green Fluorescent Protein (GFP) in Transgenic Zebrafish Embryos Under Control of Zebrafish Gene Promoters," *Develop. Genet.* 25:158-167 (1999).

Krysan et al., "T-DNA as an Insertional Mutagen in Arabidopsis," *Plant Cell* 11:2283-2290 (1999).

Ramachandran et al., "Transposons as Tools for Functional Genomics," *Plant Physiol. Biochem.* 39:243-252 (2001).

Smith et al., "Characterization and Mapping of Ds-GUS-T-DNA Lines for Targeted Insertional Mutagenesis," *Plant J.* 10(4):721-732 (1996).

\* cited by examiner

V–LB–Hyg–35P–Ipo–B–Bar–3' Ds–Ipo–B–CN–Gus–RAMP–5' Ds–Act Pro–RB–V

FIGURE 2

A  LB-V-Hyg-35P-Ipo-N-Bar-3' Ds-Ipo-N-CN-Gus-3-AAI-5' Ds-AAP-V-RB

B  LB-V-Hyg-35P-Ipo-N-Bar-3' Ds-Ipo-N-CN-Gus-AAMP-5' Ds-AAP-V-RB

FIGURE 3

A  V-TMAR-UbiP-TPase-NosT-TMAR-AP-Hyg-PinT-A4P-IAAH-NosT-Vector

B  Vector-TMAR-GIP-TPase-PinT-TMAR-A4P-IAAH-NosT-Vector

C  LB-TMAR-35P-TPase-35T-TMAR-GapP-NPTII-NosT-AAP-IAAH-NosT-RB

V-CN-E1-E2-SM2-3' Ds-PM1-VM1-SM1-PM2-E1-E2-*lox*-VM2-3SA-I-5' Ds-PM3-V

FIGURE 7

V-LB-CN-E1-TPase-GIP-Bar-3' Ds-1'P-*gfp*-Hpt-35P-E1-*lox*-Gus-3SA-AI-5' Ds-AP2-RB-V

FIGURE 8

V-LB-CN-E1-E2-Bar-3' Ds-1'P-*gfp*-Hpt-35P-E1-E2-*lox*-Gus-3SA-A1-5' Ds-A2P-RB-V

FIGURE 10

A  V-LB-CN-GIP-Cre-TPase-3' Ds-35SP-35S Enh-Hpt-1'P-E1-*lox*-ActP-5' Ds-Bar-*lox*-E1-RB-V B  V-LB-CN-EIP-Cre-GIP-TPase-3' Ds-35SP-35S Enh-Hpt-1'P-E1-*lox*-ActP-5' Ds-Bar-*lox*-E1-RB-V

FIGURE 11

Step

A. Prepare transformation plasmid

B. Transform plurality of plants/cells

C. Selection by marker gene identifies transgenics

D. Determine transgene copy number in transgenic plants/cells

E. Select "anchor" plants/cells with one copy of transgene

F. Determine physical location of transgene in chromosome after transformation event G. Pick anchor lines to have plasmid inserted every 200-600 kb in the chromosome H. Treat anchor plant with inducing agent to activate transposase I. Determine transposition distance from Anchor site J. Select transposants such that the genome of plant/cell is disrupted by a transposon every 3-6 kb, preferably 3 ± 0.5 kb to create a non-redundant, indexed, saturated, gene disruption library for that plant, animal or cell

FIGURE 12

Vector-LB-I-PpoI-5' Ds-I-PpoI-3' Ds-NPTII-RB-Vector

FIGURE 22

A. BS-EIP-Cre-*lox*-35S P-Cah-Y-BS

B. *lox*-Y-BS-EIP-Cre

FIGURE 23

A ~~~E1-Bar-3' Ds-gfp-Hpt-E1-lox-GUS-5' Ds-A2P-RA~~~

B ~~~E1-Bar-A2P-RA~~~NS~3' Ds-gfp-Hpt-E1-lox-GUS-5' Ds~~~

A. Bar-3' Ds-Hpt-E1-*lox*-Gus-5' Ds-A2P

B. ~~Bar-3' Ds-Hpt-E1-*lox*-Gus-5' Ds-A2P~~
   a                                          b C. ~~Bar-A2P~~3' Ds-Hpt-E1-*lox*-Gus-5' Ds~~
   a          b                                   c D. ~~Bar-A2P~~Y1-3' Ds-Hpt-E1-*lox*-Gus-5' Ds-Y2~~
   a          b                                        c E. *lox*-Y-BS-EIP-Cre F. ~~Bar-A2p~~Y1-3' Ds-Hpt-E1-*lox*-Y-BS-EIP-Cre-*lox*-Gus-5' Ds-Y2~~
   a          b                                                           c

FIGURE 27

PLASMIDS AND METHODS FOR CONSTRUCTION OF NON-REDUNDANT, INDEXED, SATURATION, GENE-DISRUPTION PLANT AND ANIMAL LIBRARIES

This application is a continuation-in-part of U.S. patent application Ser. No. 09/574,038, filed May 18, 2000, now abandoned, which claims the benefit of U.S. Provisional Patent Application Ser. No. 60/134,830, filed May 19, 1999.

FIELD OF THE INVENTION

The present invention relates to the design and construction of a series of plasmids which are used to produce non-redundant, indexed, saturation, gene-disruption libraries in plants and animals. This invention also relates to plants and plant and animal cells transformed with these plasmids, the progeny of such plants, and invertebrate and vertebrate cells transformed with these plasmids.

BACKGROUND OF THE INVENTION

An ultimate goal of many plant scientists is to identify and discover the function of each gene in plants. The use of molecular biology techniques allows for the manipulation of genomes directed to this objective. Such a genome project can be arbitrarily divided into three phases. Phase I involves mapping the genome by genetic and physical methods. Phase II involves cloning and sequencing all, or most, of the genes. Phase III involves determining the function of each gene, before or after the sequence of the entire genome or that of the cDNAs is known. For convenience, Phase III can be further divided into two major steps. Step one is to construct an insertional-mutant library, with the goal of disrupting each gene separately. Step one also includes determining the DNA sequence that flanks the inserted plasmid, and the chromosomal location of the inserted plasmid, in each mutant plant. Step two involves the determination of the function of each gene by examining the phenotypic, physiological, or biochemical changes of each mutant line of the saturation gene-disruption library.

Rice is used as an example, in part, because as the major staple food for over two billion people, it is one of the most important food crops in the world. Rice production must be increased by 50% by the year 2030 to feed the projected growth of population. Understanding how rice genes function will help to increase rice yields. Rice is also a convenient model system for studying gene function, because it has a relatively small genome and it was the earliest cereal plant to undergo transformation and regeneration procedures. Moreover, due to synteny of genes with other cereal plants, any information obtained on rice genes will likely be applicable to other important cereal crops, such as maize, wheat, and barley.

After about 10 years of efforts by many scientists, physical mapping of the rice genome was virtually completed several years ago. In April 2000, it was announced by the Monsanto Company (St. Louis, Mo.) that most of the rice genome sequences have been determined. Additional rice genomic sequences were released in April 2002 (Yu et al., "A Draft Sequence of the Rice Genome (*Oryza sativa* L. ssp. indica)," *Science* 296:79–92 (2002); Goff et al., "A Draft Sequence of the Rice Genome (*Oryza sativa* L. ssp. japonica)," *Science* 296:92–100 (2002)). Thus, the work in Phases I and II is essentially concluded. Small-scale Phase III work started several years ago, but progress has been slow, because the current methods of generating specific mutant lines are time-consuming and imprecise.

A significant amount of genomic work has been carried out in *Arabidopsis*, a model system, because of the relatively small genome and short generation time of *Arabidopsis*. Several partial gene-disruption libraries have already been made. One type of library uses T-DNA to disrupt the gene in the *Arabidopsis* genome, which includes some 8,000 T-DNA gene-disrupted "tagged" mutants (Feldmann et al., "A Dwarf Mutant of *Arabidopsis* Generated by T-DNA Insertion Mutagenesis," *Science* 243:1351–1354 (1989)). A major disadvantage of T-DNA tagging, and similar approaches, is that one needs as many transformation events as the number of T-tagged mutants. Since transformation of *Arabidopsis* is efficient, it is now possible to obtain 100,000 T-DNA tagged mutants with brute force (Krysan et al., "T-DNA As an Insertional Mutagen in *Arabidopsis*," *Plant Cell* 11: 2283–2290 (1999)). On the other hand, transformation of rice is much less efficient. It is not yet practical to obtain anywhere close to 200,000 T-DNA tagged rice mutants.

A second type of library makes use of an endogenous transposon, such as Mu in maize (Bensen et al., "Cloning and Characterization of the Maize An1 Gene," *Plant Cell* 7: 75–84 (1995)); tos17 Transposon in Rice (Hirochika et al., "Retrotransposons of Rice Involved in Mutations Induced by Tissue Culture," *Proc. Natl. Acad. Sci. USA* 93:7783–7788 (1996)). Although a large number of insertional mutants can be obtained, a major disadvantage of this method is that it is difficult to get desired revertants, especially if a large number of insertions are present in each plant.

A third type of library involves transferring mobile genomic sequences, known as transposable elements, or transposons, from one plant to other plants. Transposable elements are either autonomous or nonautonomous. Autonomous elements carry the gene(s) encoding for the enzymes required for transposition, thus autonomous elements have the ability to excise and transpose. Nonautonomous elements do not transpose spontaneously. They become mobile only when an autonomous member of the same family is present elsewhere in the genome. One well-characterized plant transposon is the maize Activator ("Ac") and Dissociation ("Ds") family of transposable elements. The family is comprised of the autonomous element Ac, and the non-autonomous Ds element. Ds elements are not capable of autonomous transposition, but can be trans-activated to transpose by Ac (Hehl et al., "Induced Transposition of Ds by a Stable Ac in Crosses of Transgenic Tobacco Plants," *Mol. Gen. Genet.* 217:53–59 (1989)). Thus, transposable elements, such as Ac/Ds of maize, can be transferred to other plants to generate a relatively small number of anchor plants (such as 500), and then to produce a much larger number of secondary insertional-mutant plant lines. The major advantage to this method is that one needs a relatively small number of anchor plant lines (such as several thousand) to generate a large population of secondary mutant plant lines (such as 200,000) after transposition (Hehl et al., "Induced Transposition of Ds by a Stable Ac in Crosses of Transgenic Tobacco Plants," *Mol. Gen. Genet.* 217:53–59 (1989); Bancroft et al., "Transposition Pattern of the Maize Element Ds in *Arabidopsis Thaliana*," *Genetics* 134:1211–1229 (1993)).

From published reports, it is known that over 70% of the insertional mutants in *Arabidopsis* have no readily visible phenotype, which makes identification of transposition sites difficult, if not impossible. The Ac/Ds system was improved by using enhancer- and gene-trap plasmids (Sundaresan et al., "Patterns of Gene Action in Plant Development Revealed by Enhancer Trap and Gene Trap Transposable Elements," *Genes &Develop.* 9:1797–1810 (1995)), which allow disrupted genes with no phenotype to be detected by expression of a reporter gene (such as Gus). As of 1999, this type of library includes less than 15,000 Ac/Ds-tagged rice plant lines (Chin et al., "Molecular Analysis of Rice Plants Harboring An Ac/Ds Transposable Element-Mediated Gene Trapping System," *Plant J.* 19: 615–623 (1999)). Therefore, many more additional plant lines both in rice and *Arabidopsis* are still needed to produce a saturation library. One advantage of this type of insertional-mutant library is that it includes both gene tagging and knockout features. Another advantage of Ac/Ds-tagged plants is that revertants can be obtained relatively easily.

Another type of insertion-mutant library is known as the activation-trap library. Activation tagging uses T-DNA vectors that contain multimerized transcriptional enhancer from cauliflower mosaic virus ("CaMV") 35S genes. After insertion in the plant genome, the enhancers in the T-DNA can cause transcriptional activation of nearby genes in the plant genome. Thus, use of the activation trap future results in over-expression of the nearby genes which may result in changes in phenotype (Weigel et al., "Activation Tagging in *Arabidopsis,*" *Plant Physiology* 112:1003–1013 (2000)).

Each of the three types of libraries: the gene-trap, enhancer-trap, and activation-trap, also suffers from the same problem as T-DNA tagged plants, or use of an endogenous transposon to produce gene-disruption libraries, i.e., all of these libraries are constructed by a random "shotgun"-type approach. In any random approach, large amounts of time are wasted analyzing a high percentage of redundant plant lines. The general practice by most scientists is to generate and then analyze a tenfold excess of randomly generated plant lines to cover approximately 99% of the genome by calculation. For example, to achieve a 99% probability of tagging all the genes in the rice genome, 400,000 tagged plant lines are needed. The laboratory of Shimamoto obtained around 500 tagged mutant rice lines in 1993 (Shimamoto et al., "Trans-Activation and Stable Integration of the Maize Transposable Element Ds Cotransfected with the Ac Transposase Gene in Transgenic Rice Plants," *Mol. Gen. Genet.* 239: 354–360 (1993)), and close to 8,000 by 1999 (Enoki et al., "Ac as a Tool for the Functional Genomics of Rice," *The Plant J.* 19:605–613 (1999)). There are at least three publications which show that after Ac/Ds-containing plasmids are integrated into the rice genome, transposition does occur and that the frequency of transposition in rice is relatively high, in the range of 3–15% (Shimamoto et al., "Trans-Activation and Stable Integration of the Maize Transposable Element Ds Cotransfected with the Ac Transposase Gene in Transgenic Rice Plants," *Mol. Gen. Genet.* 239: 354–360 (1993); Enoki et al., "Ac as a Tool for the Functional Genomics of Rice," *Plant J.* 19:605–613 (1999); Chin et al., "Molecular Analysis of Rice Plants Harboring An Ac/Ds Transposable Element-mediated Gene Trapping System," *Plant J.* 19: 615–623 (1999)).

Production of still another type of insertion-mutant has been reported by applying a poly A-trap approach in differentiated mouse embryonic stem cells and mouse embryos (Salminen et al., "Efficient Poly A Trap Approach Allows the Capture of Genes Specifically Active in Differentiated Embryonic Stem Cell and in Mouse Embryos," *Develop. Dynamics* 212:328–333 (1998)). In this approach, only expressed genes are trapped. This is because special vectors have been constructed that allow the trapping of only expressed genes in mouse embryonic stem (ES) cells. One plasmid included the neomycin phosphotransferase gene (neo) for selection. However, the polyadenylation (poly A) sequence of neo was not present. Thus, neo-resistant ES cells were obtained only when the plasmid was integrated next to a poly A sequence of an endogenous gene. These transformed cells then represent those that trapped the expressed genes. In the next step, selected ES cell clones were introduced into mouse embryos by microinjection or aggregation of cells and chimeric mice were generated. The advantage of producing a poly A trap library is that one need not generate a very large number (such as one million) of insertion mutants since the number of genes in most eukaryotes are in the range of 25,000 to 80,000. The disadvantage of this approach is that the efficiency of poly A trapping is relatively low, and not all expressed genes can be trapped. Moreover, the mutant library produced by this method is not indexed, and it is not known what percent of the expressed genes are actually trapped.

Even though some methods are already available for studying the functions of individual genes in a genome, the existing methods are very time-consuming and labor intensive because of the large number (>200,00) of mutant lines that need to be screened following gene disruption. It has been estimated that the amount of work needed for Phase III research is on the order of ten times the combined efforts of Phase I and II work.

Within Phase III research, two major steps are included. Step one involves generating a well-spaced saturation gene-disrupted library, followed by determination of the flanking DNA sequences of the transposed genes. Step two involves the examination for phenotypic, physiological, or biochemical changes in all insertion mutant lines. Using the current methods, the time and effort needed for Step two analysis of a saturation gene-disruption plant library are far greater than those required for Step one. This is because the identification of the function of specific genes, for example, 25,000 genes in *Arabidopsis* plant lines, may require the generation and then analysis of 250,000 randomly produced plant lines due to redundancy. For each plant line, at least five plants are usually needed. Thus, improvements in the current methods are needed to make both Steps of Phase III work faster and less labor-intensive. What is needed to improve Step one is a method which systematically tags all genes in a given plant genome to produce an indexed insertion-mutant library. This, in turn, can eliminate the need for extreme redundancy in screening for phenotypic, physiological, or biochemical changes in Step two, thereby drastically reducing the time and labor required for subsequent gene identification. The present invention is directed to improving Step one so that the work involved in Step two can be greatly reduced, thereby overcoming these and other deficiencies in the current art.

SUMMARY OF THE INVENTION

The present invention relates to a method of constructing a non-redundant, saturation, gene-disruption plant library. This involves providing a plasmid having two clusters of unique enzyme-cutting sites and two dissociation elements, and transforming a plurality of plants with the plasmid to produce a plurality of transformed plants with the plasmid integrated at different locations within the genome of the plants. Next, the locations of the integrated plasmid in the transgenic plants are mapped to identify anchor transgenic plant lines with the integrated plasmid suitably spaced within the genome of the plants. Each of the homozygous anchor transgenic plant lines is then crossed with a plant having an activator element to form progeny plants. The crossing activates transposition of a portion of the plasmid bounded by the two dissociation elements to form a plurality of progeny plants having different genes disrupted. Next, the method of the present invention involves digesting the plant genome at different unique enzyme-cutting sites to release a DNA fragment from each of the transgenic progeny plants, and measuring the size of each of the released DNA fragments to determine transposition distances in each of the transgenic progeny plants. Next, progeny transgenic plants are selected with the transposition distances which are different from the transposition distances of the other progeny transgenic plants by a pre-determined amount to prepare a non-redundant saturation, gene-disruption plant library.

The present invention also relates to a plasmid having an insert containing two dissociation elements and two clusters of unique enzyme-cutting sites. One cluster of unique enzyme-cutting sites is between the two dissociation elements in the insert, and the second cluster of unique enzyme-cutting sites is not between the two dissociation elements in the insert.

The present invention also relates to plants transformed with the plasmid of the present invention, and the progeny thereof.

The present invention also relates to another method of constructing a non-redundant, indexed, saturation, gene-disruption genomic library of an organism. This method involves providing a first plasmid that includes a transposon-specific recognition sequence having 5' and 3' ends which form the boundaries of the transposon-specific recognition sequence, and 2 clusters of restriction enzyme recognition sites. One cluster is located inside the boundaries of the transposon-specific recognition sequence and the second cluster is located outside the boundaries of the transposon-specific recognition sequence. The enzyme recognition sites in one cluster are identical to the enzyme recognition sites in the second cluster but the enzyme recognition sites in both clusters either do not exist or are rare in the organism in which the library is being constructed. This first plasmid also has one or more promoter elements operably linked to each gene in the plasmid, and one or more 3' terminator elements operably linked 3' to each gene in the plasmid. The plasmid also contains one or more first selection marker genes located inside the boundaries of the transposon recognition sequence and operably linked to a promoter element and a 3' terminator element. Also included in the plasmid are one or more detection genes, where at least one of the one or more detection genes is located inside the boundaries of the transposon recognition sequence, and is operably linked to a promoter element and a 3' terminator element. A second plasmid is also provided, having a transposase gene that is operably linked to at least one promoter element and to a 3' terminator element. This plasmid also has one or more second selection marker genes, with each selection marker gene operably linked to a promoter element and a 3' terminator element and where the first selection marker gene is different from the second selection marker gene. A plurality of organisms are co-transformed with the first plasmid and the second plasmid to produce a plurality of co-transformed anchor transgenic organisms with the first and second plasmids integrated at different sites within the transgenic organism's genome. The integration site of a first plasmid due to transformation is defined as a plasmid's anchor location. A plurality of transgenic anchor organisms are selected, each having one copy of the first and second plasmid integrated into the genome. An anchor location for each integrated first plasmid in the plurality of transgenic organisms is mapped to identify anchor transgenic lines, each identified anchor transgenic line harboring a first plasmid within its genome at a location at least 200–600 kilobases away from the location of a first plasmid in the other anchor transgenic lines. Transposition is allowed to occur to produce a plurality of transposants having different genes disrupted. The transposon-specific recognition sequence of the first plasmid has transposed from its anchor location to a different reintegration location in the transposant's genome, which defines a "transposition distance" between the anchor location and the reintegration location. Next, the transposition distances of the transposed transposon-specific recognition sequences is determined in a plurality of transposants resulting in a given anchor line. Next, a plurality of transposants are selected, each having a transposition distance that is different from the transposition distances of the other transposants to prepare a non-redundant, indexed, saturation, gene disruption library.

The present invention also relates to a transformation plasmid for constructing a gene-disruption library having an insert containing a transposon-specific recognition sequence with 5' and 3' ends which form the boundaries of the transposon-specific recognition sequence, and 2 clusters of restriction enzyme recognition sites. One cluster is located inside the boundaries of the transposon-specific recognition sequence and the second cluster is located outside the boundaries of the transposon-specific recognition sequence. The enzyme recognition sites in one cluster are identical to the enzyme recognition sites in the second cluster but the enzyme recognition sites in both clusters either do not exist or are rare in the organism which is to be transformed with the plasmid. This plasmid also includes one or more promoter elements operably linked to each gene in the plasmid, and one or more 3' terminator elements linked 3' to each gene in the plasmid. This plasmid also has one or more first selection marker genes, located inside the boundaries of the transposon-recognition sequence and operably linked to a promoter element and a 3' terminator element. The plasmid also contains one or more detection genes located inside the boundaries of the transposon-recognition sequence and which is operably linked to a promoter element and a 3' terminator element.

The present invention also relates to organisms transformed with the plasmid of the preceding paragraph.

The present invention also relates to a transformation plasmid for constructing a gene disruption library having an insert containing a transposase gene operably linked to a promoter element and a 3' terminator element. The plasmid also contains one or more selection marker genes, where each of the one or more selection marker genes is operably linked to a promoter element and a 3' terminator element.

The present invention also relates to organisms transformed with the plasmid of the preceding paragraph.

The present invention additionally pertains to a method of replacing a disrupted gene of interest at a specific location on an organism's genome.

The present invention also relates to a method of constructing a non-redundant, indexed, saturation, gene-disruption activation-tagging library in an organism. This method involves providing a plasmid having a transposon-specific recognition sequence with 5' and 3' ends which form the boundaries of the transposon-specific recognition sequence, and 2 clusters of restriction enzyme recognition sites. One cluster is located inside the boundaries of the transposon-specific recognition sequence and the second cluster is located outside the boundaries of the transposon-specific recognition sequence. The enzyme recognition sites in one cluster are identical to the enzyme recognition sites in the second cluster but the enzyme recognition sites in both clusters either do not exist or are rare in the organism in which the library is being constructed. Also included in this plasmid is a transposase gene, which is located outside the boundaries of the transposon-specific recognition sequence and is operably linked to an inducible promoter and a 3' terminator element. The plasmid also contains one or more 5' promoter elements operably linked to each gene in the plasmid, and also has one or more 3' terminator elements operably linked to each gene in the plasmid. The plasmid also contains one or more enhancer elements located inside the boundaries of the transposon-recognition sequence and situated next to a promoter. Also included is a Cre recombinase gene located outside the boundaries of the transposon-recognition sequence and which is operably linked to a promoter element and a 3' terminator element. In addition, the plasmid contains one or two Cre-lox recombinase recognition sequences, where at least one lox sequence is located inside the boundaries of the transposon recognition sequence. The plasmid also contains one or more selection marker genes, with at least one of the selection marker genes located inside the boundaries of the transposon-recognition sequence, and where each selection marker gene is operably linked to a promoter element and a 3' terminator element. This method also involves transforming a plurality of organisms with the plasmid to produce a plurality of transformed anchor organisms having the plasmid integrated at different sites within the transgenic organisms' genome, where the integration site of a plasmid due to transformation is defined as a plasmid's anchor location. A plurality of anchor transgenic organisms are selected, each having one copy of the plasmid integrated into the anchor transgenic organism's genome. The anchor location of each integrated plasmid in the plurality of transgenic organisms is mapped to identify anchor transgenic lines, where each identified anchor transgenic line harbors a plasmid within its genome at a location least 200–600 kilobases away from the location of a plasmid in other anchor transgenic lines. Expression of the transposase gene in the anchor transgenic organisms is induced, where inducing activates transposition of a portion of the plasmid bounded by the 5' and 3' ends of the transposon recognition sequence to form a plurality of transposants having different genes disrupted. The transposon-specific recognition sequence of the plasmid transposes from its anchor location to a different reintegration location in the anchor transgenic organism's genome, which defines a "transposition distance" between the anchor location and the reintegration location in a transposant's genome. Next, the transposition distances of transposed transposon-specific recognition sequences in a plurality of transposants in a given anchor transgenic line are determined. A plurality of transposants are selected, each having a transposition distance which is different from the transposition distances of the other transposants to prepare non-redundant, indexed, saturation, gene-disruption library.

The present invention also relates to an activation-tagging transformation plasmid for gene disruption in an organism having a transposon-specific recognition sequence having 5' and 3' ends which form boundaries of the transposon-specific recognition sequence and 2 clusters of restriction enzyme recognition sites. One cluster is located inside the boundaries of the transposon-specific recognition sequence and the second cluster is located outside the boundaries of the transposon-specific recognition sequence. The enzyme recognition sites in one cluster are identical to the enzyme recognition sites in the second cluster, but the enzyme recognition sites in both clusters either do not exist, or are rare, in the organism in which the library is being constructed. This plasmid of the present invention also includes a transposase gene, which is located outside the boundaries of the transposon-specific recognition sequence and is operably linked to a promoter element and a 3' terminator element. The plasmid also contains one or more 5' promoter elements operably linked to each gene in the plasmid, and one or more 3' terminator elements operably linked 3' to each gene in the plasmid. This plasmid also contains one or more selection marker genes located inside the boundaries of the transposon-recognition sequence and which is operably linked to a promoter element and a 3' terminator element. The plasmid also contains one or more detection genes located inside the boundaries of the transposon-recognition sequence, and where each detection gene is operably linked to a promoter element and a 3' terminator element. Also included in this plasmid are one or more enhancer elements located inside the boundaries of the transposon-recognition sequence next to a promoter. The plasmid also contains a Cre recombinase gene located outside the boundaries of the transposon-recognition sequence and which is operably linked to a promoter element and a 3' terminator element. There is also included in this plasmid one or two Cre-lox recombinase recognition sequences, with at least one lox sequence located inside the boundaries of the transposon-recognition sequence.

The present invention also relates to organisms transformed with the plasmid of the preceding paragraph.

The present invention additionally pertains to a method of replacing a disrupted gene of interest at a specific location of interest on an organism's genome. This method involves providing an organism in which a heterologous integrated transposition plasmid with a Cre-lox recombinase recognition sequence has disrupted a gene to produce a transposant organism. The disrupted gene's nucleic acid sequence is determined. Next a circular transformation plasmid is provided which has a Cre recombinase gene, operably linked to an inducible promoter and a 3' terminator element; a Cre-lox recognition sequence, and a nucleic acid molecule encoding the disrupted gene of interest. The transposant organism is transformed with the circular plasmid, and the expression of the Cre gene is induced. Inducing activates the Cre recombinase to cleave the plasmid at Cre-lox recognition sequence, which integrates the circular plasmid into the transposant, thereby replacing the disrupted gene with an intact gene.

The present invention also relates to a method of deleting a DNA segment of a given size, at any chromosomal location, from the genome of a transformed organism. This method involves providing an organism transformed with one copy of an activation tagging transformation plasmid of the present invention, where transformation has integrated the plasmid within the organism's genome to create a transgenic organism. The genomic integration site of the plasmid is defined as the plasmid's anchor site. The Cre recombinase gene of the integrated plasmid is under the control of an inducible promoter operably linked to the nucleic acid encoding the Cre gene, and the plasmid contains two lox recombinase recognition sequences, with one of the two lox recombinase recognition sequences located within the boundaries of the transposon-specific recognition sequence. The plasmid's location in the transgenic organism is mapped to identify anchor organisms. Then, transposition is allowed to occur to produce a plurality of transposant organisms having different genes disrupted. The genomic DNA of a plurality of transposants is digested with a specific enzyme to release from each transposant a DNA segment located between the clusters of enzyme recognition sequence. The released DNA segment sizes are measured to determine transposition distances in each transposant, and a plurality of transposants are selected in which each transposant has a transposition distance which is different from the transposition distances of other transposants to prepare a non-redundant, indexed, saturation, gene-disruption library. Expression of the inducible promoter operably linked to the Cre gene is induced, thereby activating the Cre recombinase to catalyze excision of a DNA segment from any specific location in transposant in between two lox sites, thereby deleting the DNA segment.

The present invention also relates to a method for over-producing a gene product of interest in an organism. This method involves providing a gene-trap and gene-enhancer insertion-mutant library having a plurality of transposant organisms harboring a single Cre-lox recombinase recognition sequence site. A genomic locus of a transposant organism is identified at which transcription activity is high based on the results from specific transposants in the gene-trap and enhancer-trap insertion-mutant library as compared with the same locus in a non-transposant organism. A gene is inserted using the gene replacement method according to the present invention, wherein the gene of interest is inserted into a specific transposant at the single lox site, thereby allowing the gene product of interest to be over-produced.

By providing for an insertional-mutant library that is more complete and less redundant than those libraries produced by current methods, the present invention provides three major advantages. First, the present invention requires only a small fraction of the time and labor currently needed to analyze the same number of plant or cell lines. Second, the present invention requires sequencing only the flanking sequences by inverse PCR of those pre-selected transposant lines without having to sequence a ten- to twenty-fold larger number of all mutant plants. Third, the method of the present invention leaves no gaps in this region or any other regions in the entire genome. In other words, all the genes can be systematically tagged (disrupted). Thus, the present invention provides an advantage over current methods not only by making the entire process of producing an indexed insertion-mutant library simpler and faster, but also increasing the probability of tagging a larger percent of the genes for analysis. Moreover, others in the future can make use of these superior, indexed, insertion-mutant libraries for Phase III, Step two, analysis of the function of a very large number of genes much more rapidly than is now possible. Finally, the same principle and approach are applicable to many living organisms, including plants and animals as well as vertebrate and invertebrate cells.

BRIEF DESCRIPTION OF THE DRAWINGS

FIG. 1A shows details of the construction of plasmid pSDsG, designed for rice or other monocot transformation. FIG. 1B is an abbreviated view of the components of pSDsG, shown without 3' terminators. FIG. 1C shows the abbreviated structure of the remaining pSDsG plasmid following integration and transposition of the dissociation ("Ds") element. FIG. 1D is a plasmid similar to pSDsG with two lysozyme matrix ("MAR") sequences added.

FIG. 2 shows an abbreviated view of the structure and components of an enhancer-trap plasmid, pSDsE, designed for transformation of rice or other monocot cells.

FIGS. 3A–B show the components of plasmids pSDsG and pSDsE for dicot transformation. FIG. 3A shows an abbreviated super gene-trap plasmid, pSDsG, for dicot transformation. FIG. 3B shows an abbreviated super enhancer-trap plasmid, pSDsE, for dicot transformation, which has the *Arabidopsis* Act2 minimal promoter ("AAMP") included.

FIGS. 4A–C show an abbreviated view of three Ac-containing plasmids. FIG. 4A is an Ac-containing plasmid for transforming monocots, such as rice. It also contains a tobacco matrix attachment region ("TMAR") sequence. FIG. 4B shows an Ac-containing plasmid with an inducible promoter ("GIP"). FIG. 4C shows an Ac-containing plasmid for transforming dicots such as *Arabidopsis*, which also includes two tobacco MAR sequences.

FIG. 6 shows the general components of a plasmid that includes both a gene-trap and an enhancer-trap feature for transformation of plants. "V" is a vector (in certain cases, it may include the left and right border sequence of 10 *Agrobacterium*), "CN" is a nucleic acid sequence endogenous to the plant for rapid analysis of copy number of the transgene, "SM1" and "SM2" are selectable marker genes 1 and 2, 3' Ds and 5' Ds are recognition sequences of the mini maize Ac transposon, "PM1", "PM2" and "PM3" are promoters, "VM1" and "VM2" are visible marker genes, "E1" and "E2" are rare restriction enzyme recognition sites, "3SA" is splicing acceptor sequences, and "1" is an intron.

FIG. 7 shows the components of an advanced plasmid that includes both a gene-trap and an enhancer-trap feature as shown in FIG. 6, but with the addition of a lox sequence. lox is the 34 bp Cre recombinase recognition sequence.

FIG. 8 shows an exemplary gene-disruption transformation plasmid of the third embodiment of the present invention that harbors both an Ac-transposase gene and the Ds element. GIP is a glucocorticoid inducible promoter and TPase is the maize Ac transposase gene. E1 represents the identical cluster of rare restriction enzyme sites located inside and outside of the boundaries of the Ds element. The plasmid of FIG. 8 also contains both a gene-trap and an enhancer-trap feature.

FIG. 9A shows the integrated version of the plant-specific activation-tagging plasmid following transformation into an anchor site in a plant chromosome. FIG. 9B shows the re-integration of the Ds transposon element after activation of the TPase with dexamethasone treatment. Wavy lines designated "a," "b," and "c" represent segments of plant chromosome.

FIG. 10 shows a specific plasmid for transformation of *Arabidopsis* (as an example) that includes both the gene-trap and the enhancer-trap features. Here the vector may be CAMBIA 1300, LB and RB are the left and right border sequences, CN is an internally truncated *Arabidopsis* AP3 gene, E1 and E2 are IppoI and PmeI recognition sequences, Bar is a phosphinothricin acetyltransferase gene, 1'P is the 1' promoter, gfp is a green fluorescent protein gene, Hpt is a hygromycin phosphotransferase gene, 35P is the minimal CaMV 35S promoter, Gus is a beta-glucuronidase gene, 3SA is a three splicing acceptor site of *Arabidopsis*, AI is an *Arabidopsis* gene intron, and A2P is an *Arabidopsis* actin 2 promoter. Note that for simplicity of presentation, 3' terminators of genes are not included in this plasmid.

FIGS. 11A–B show exemplary versions of plasmids harboring both a self-activating, self-inactivating Ac-transposase gene and Ds elements to generate an activation-tagging library, and a Cre-lox recombinase feature. FIG. 11A shows a plasmid with the TPase gene under control of a constitutive promoter, and the glucocorticoid-inducible promoter, GIP, driving expression of the Cre gene. FIG. 11B shows a plasmid with TPase under the control of GIP, while EIP, the estrogen-inducible promoter, is driving expression of the Cre gene. 35S Enh is four copies of the 35S enhancer element (350 bp per copy) from the CaMV 35S promoter; Hpt is hygromycin phosphotransferase gene, which confers resistance to the antibiotic hygromycin; is Bar is the phosphinothricin acetyl transferase gene to confer herbicide resistance; 1'P is an *Agrobacterium* promoter; lox is the lox recognition site for Cre recombinase.

FIG. 12 is a diagram of the steps involved in constructing a non-redundant, indexed, saturation, gene-disruption activation-tagging library in an organism.

Figure 13:
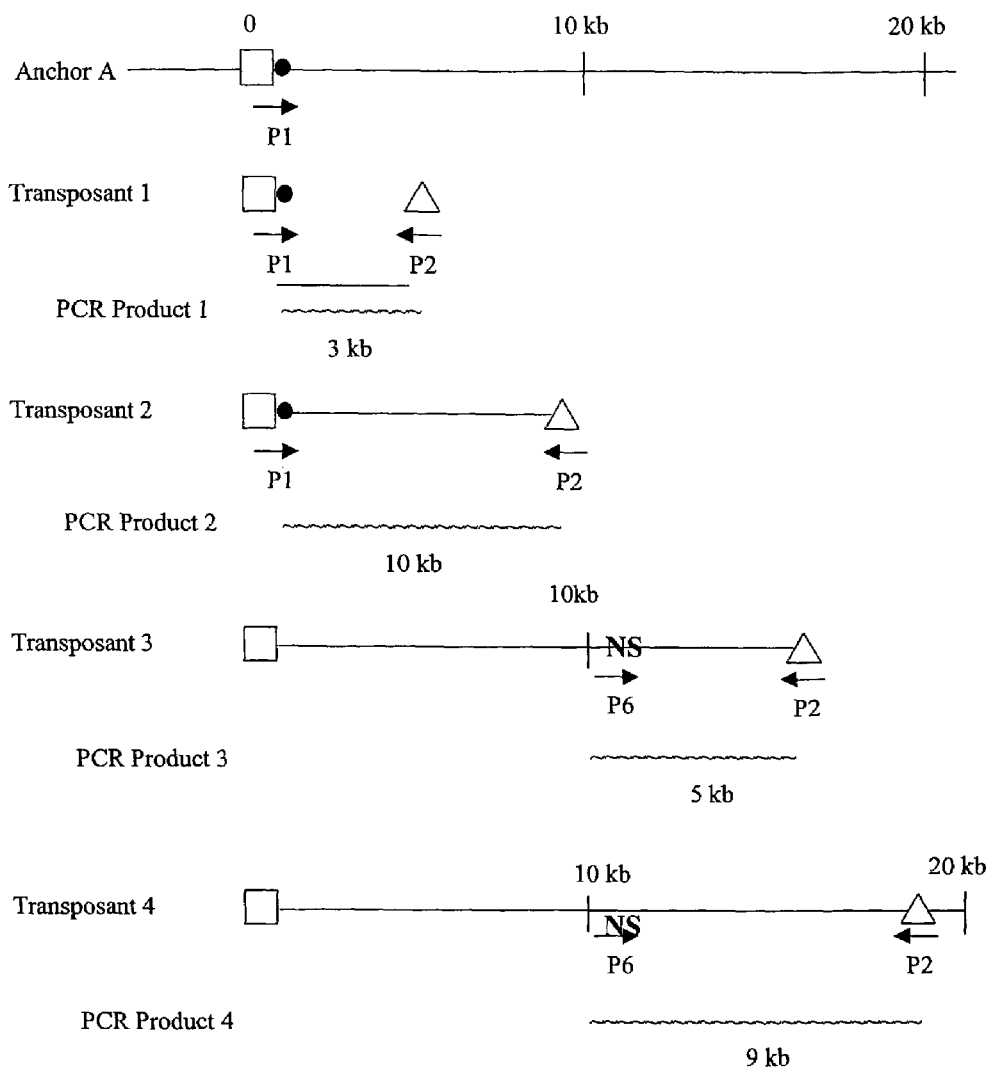

FIG. 13 is a diagram of the steps involved in determining the transposition distance in a transposant using the long PCR method. The square designates the "anchor," i.e., insertion site of the transformation plasmid. The triangle designates the transposition site of the plasmid following the transposition event. "P1," "P2," and "P6" represent PCR primers 1, 2, 6, respectively, for four exemplary transposants. NS is the flanking sequence of the transposed transposon recognition sequence.

Figure 14:
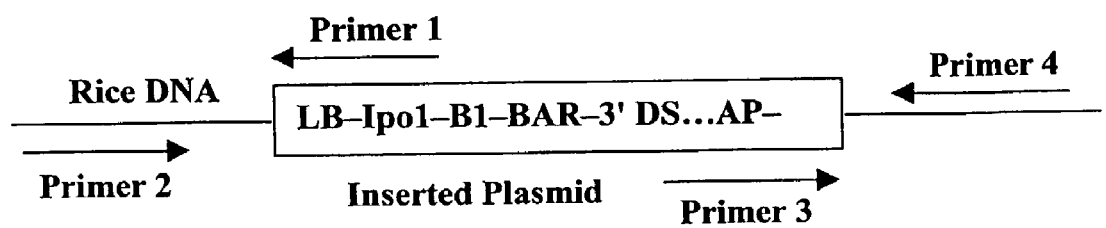

FIG. 14 shows a PCR-based amplification scheme for use in determining the physical location of the inserted plasmids in transformed Ds-containing rice plants.

Figure 15:
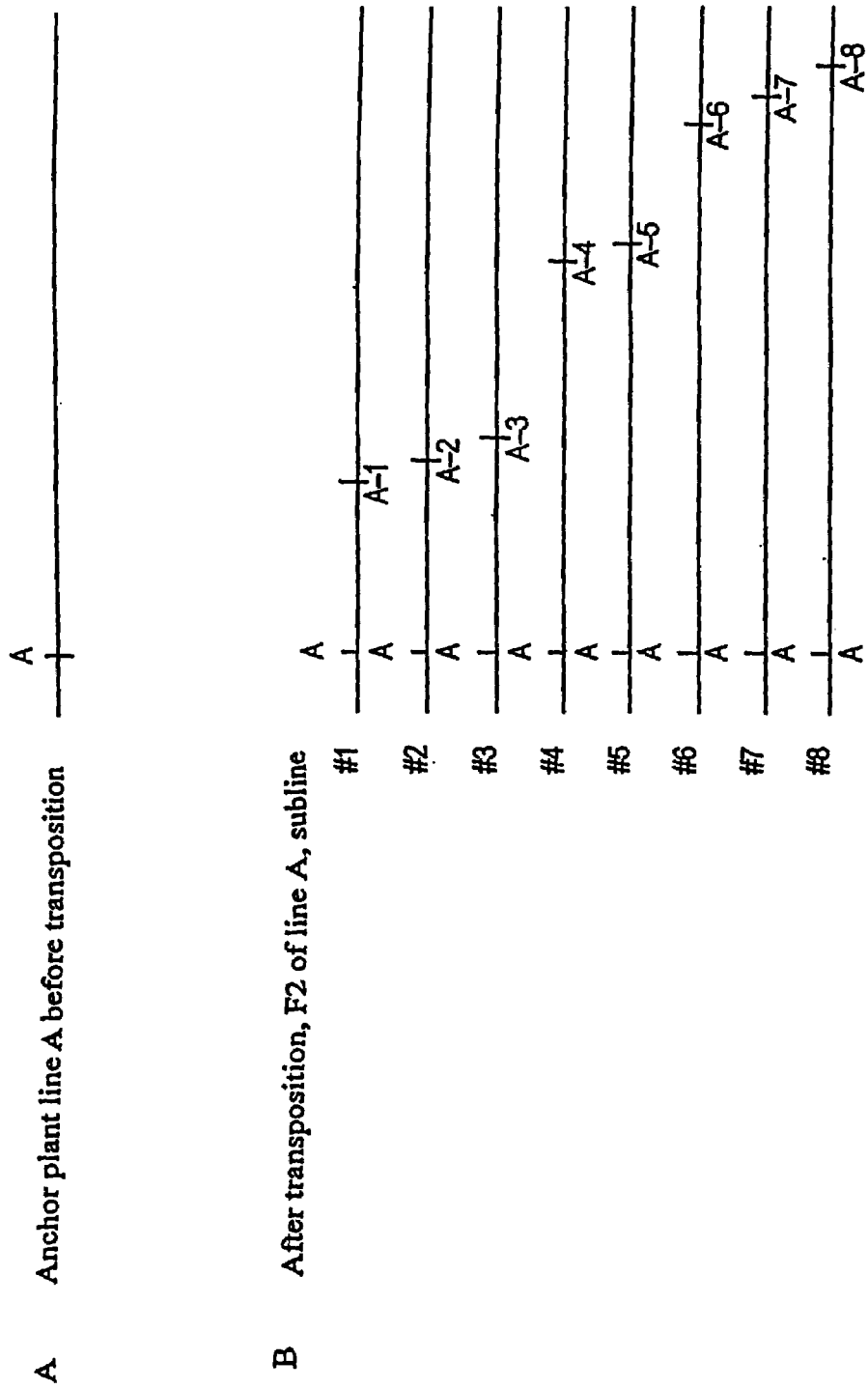

FIGS. 15A–B show an analysis of transgenic plants for determining the location (distance) of transposition. FIG. 15A shows anchor line A before transposition. "A" indicates the site of integration of the Ds-containing transformation plasmid into the chromosome of the transformed plant. FIG. 15B shows F2 plant lines #1–8 after transposition of the Ds-containing segment. "A-1" through "A-8" designate the plasmid transposition site on the chromosome relative to anchor.

FIGS. 16A–B illustrate the analysis of an F2 plant line in which the Ds-containing segment from pSDsG is assumed to be transposed to a location approximately 90 kb away from the anchor position. FIG. 16A is an expanded map of the right-hand side of anchor line A shown in FIG. 15A, before transposition. "LA" and "RA" represent the plant sequence immediately beyond the left and right borders of the plasmid, respectively. The box above FIG. 16A shows the Ds element transposing, i.e, "jumping" from its anchor location next to the Bar gene, to the right of the right anchor site border. FIG. 16B shows the same anchor line after transposition of the Ds element to the right of RA on the chromosome.

Figure 17:
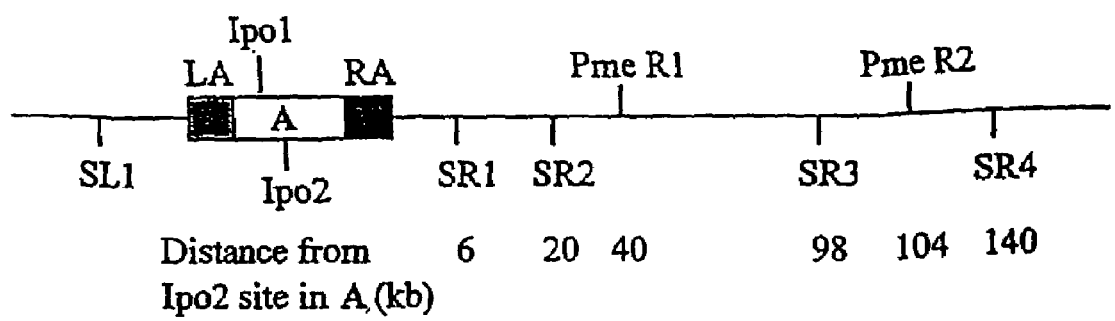

FIG. 17 is an abbreviated physical map of the components around the original integration site in anchor Plant A.

Figure 18:
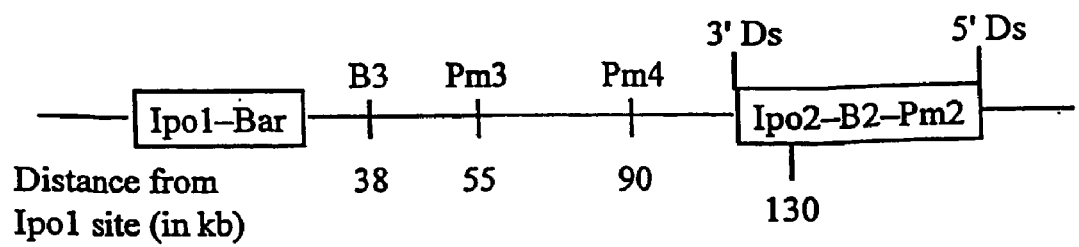

FIG. 18 shows the determination of the transposition distance in subline #7 from FIG. 15B using progressive restriction digestion and gel electrophoresis to determine the distance from the anchor site. "Ipo1-Bar" in the box represents the anchor site, "B3" represents a BglI site, "Pm3" and "Pm4" represent two consecutive Pme 1 sites.

Figure 19:
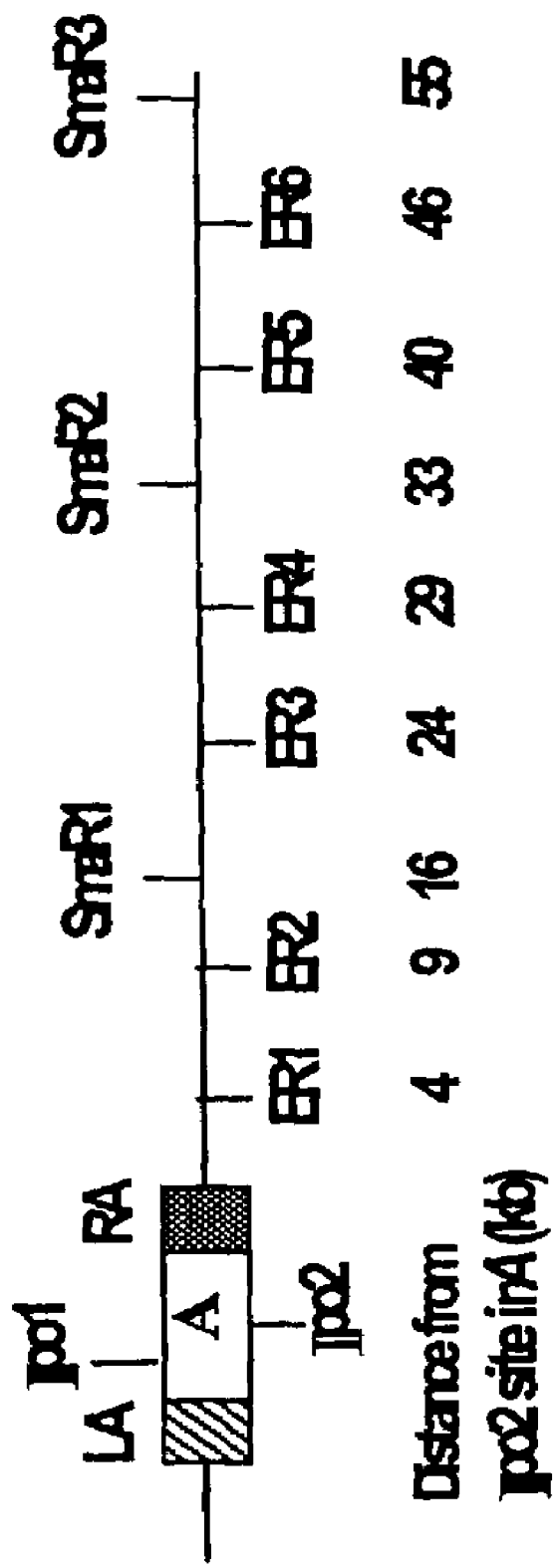

FIG. 19 shows an expanded map of the right-hand side of Anchor line A before transposition, where ER1, ER2, ER3, etc., are the approximate location of any rare enzyme recognition sites on the right-hand side of the Anchor position A and SmaR1 and SmaR2 represent two consecutive chromosomal Sma1 sites.

Figure 20:
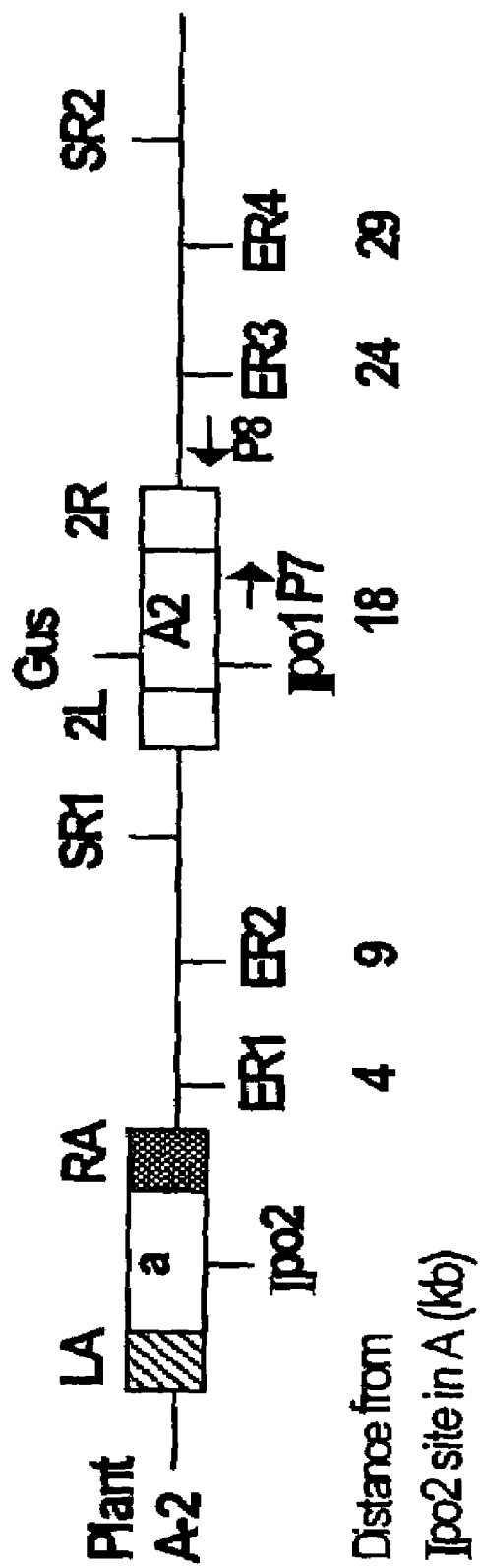

FIG. 20 shows the location of the transposed plasmid in plant line A-2. The position of the reinserted Ds-containing part of the plasmid is shown as the box in the center of this figure, which includes the visible Gus marker gene.

Figure 21:
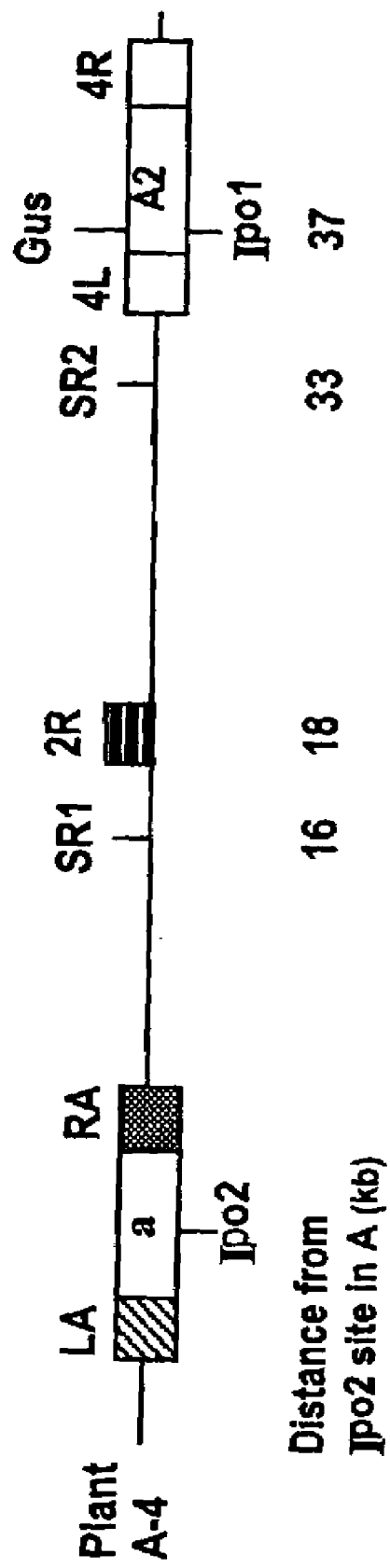

FIG. 21 shows transformed plant A-4 after transposition, where the distance of transposition is approximately 37 kb (±3 kb) from Ipo2 site in A, and an SR2 site is known to be approximately 33 kb from the Ipo2 site.

FIG. 22 shows the major components of a Ds-containing plasmid, pEDI, for transformation of *Arabidopsis*. Included in the plasmid is an NPTII gene for kanamycin resistance and two restriction endonuclease recognition site cluster, designated only as "I-PpoI," for determination of transposition distance.

FIG. 23A shows a Cre-lox-containing gene-replacement transformation plasmid, where BS represents the pBluescript vector, EIP is an estrogen inducible promoter, Cre is the Cre recombinase gene, and Y is a gene to be used to replace an interrupted gene, Cah is the cyanamide hydrolase gene for selection during transformation. FIG. 23B is an abbreviated version of FIG. 23A. Since this plasmid is in the circular form, the symbol shown on the left-hand side can be any one of the components.

Figure 24:
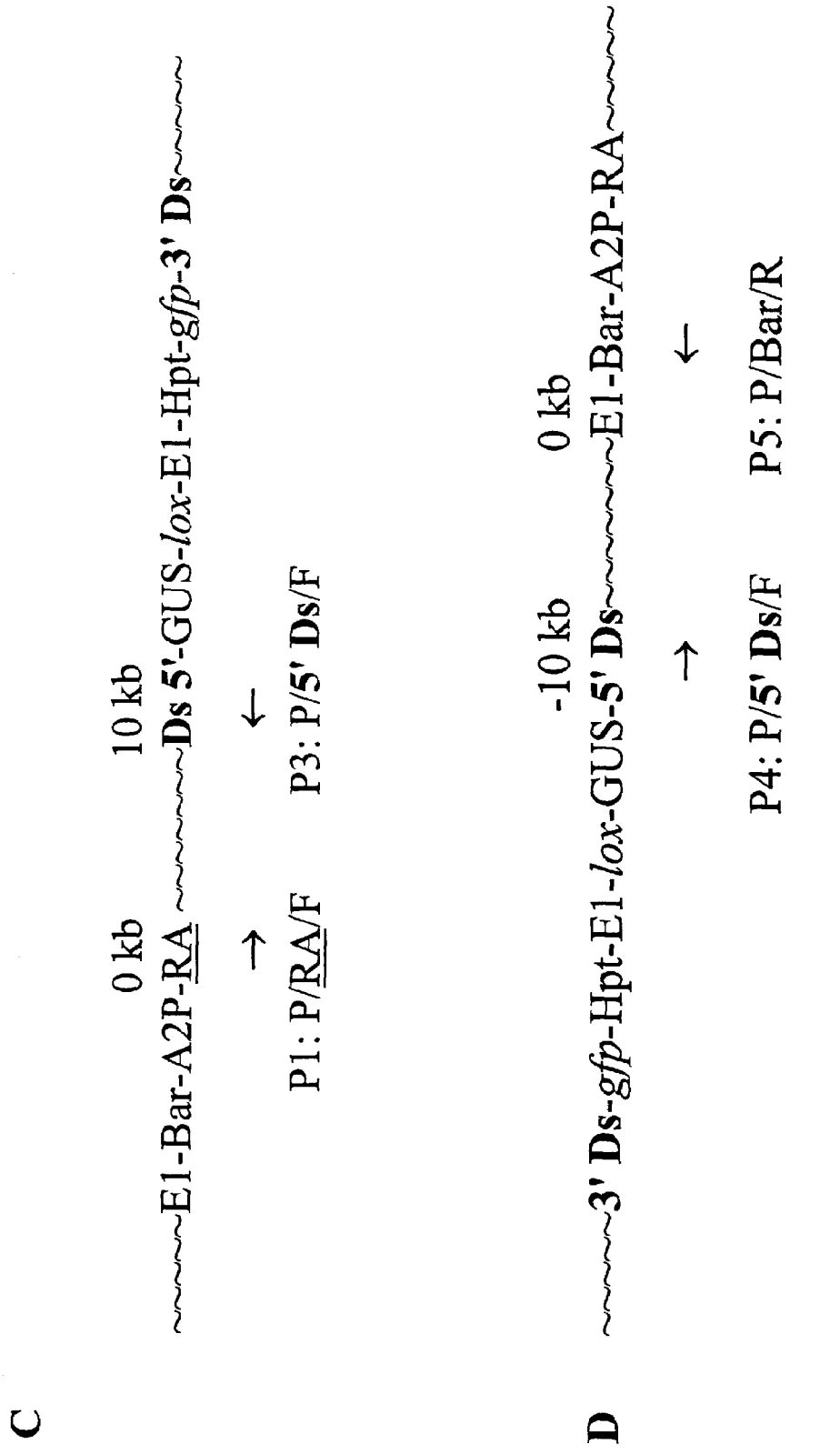
Figure 24:
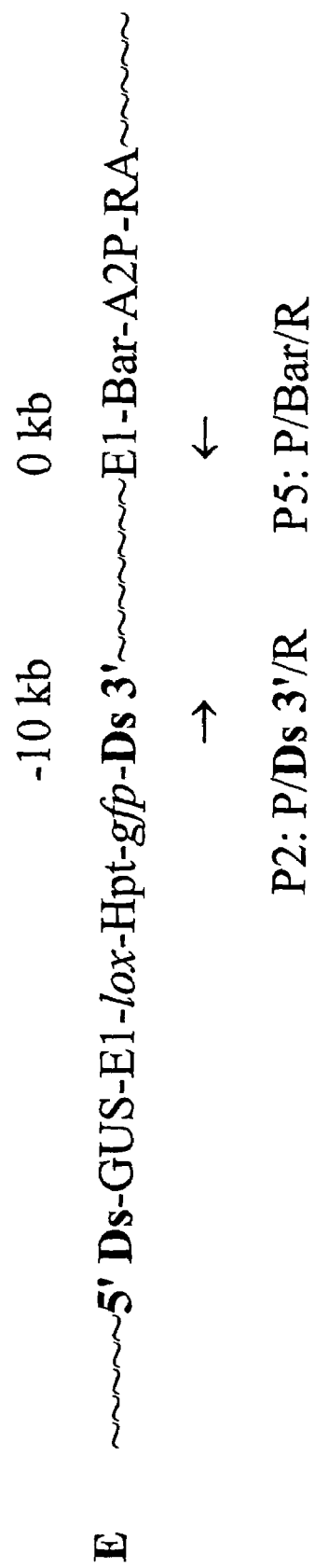

FIGS. 24A–E show a variety of possible structures of an integrated Ds-containing plasmid in an exemplary transformed anchor plant, "A2-3," and its progeny. FIG. 24A shows the integration of a Ds-containing plasmid into the host genome of A2-3 following transformation, but prior to transposition. "RA" is the right-side flanking sequence of anchor plant A2-3. FIG. 24B shows the Ds element inserted approximately 10 kb from the anchor site in an F2 plant A2-3-4A following the transposition event. The flanking sequence of Ds after transposition is shown as "NS." "P1" and "P2" are the primers used for long PCR to determine the location relative to the anchor site by simply measuring the length of the PCR product. The locations of the primer sequences and their directional orientation are shown by arrows below the diagram in FIG. 24B. FIG. 24C shows plant A2-3-4B following transposition. The Ds element has transposed to the right of the anchor site and inverted its orientation during reinsertion. The location of primers "P1" and "P3" used to determine the transposition distance are indicated by the arrows below the diagram. FIG. 24D shows plant A2-3-4C following transposition. The Ds element has transposed to the left of the anchor site, maintaining its original orientation. Primers "P4" and "P5" are indicated below the diagram. FIG. 24E shows plant A2-3-4D following transposition. The Ds element has transposed to the left of the anchor site, and inverted its original orientation during reinsertion. Primers "P2" and "P5" are indicated below the diagram.

Figure 25:
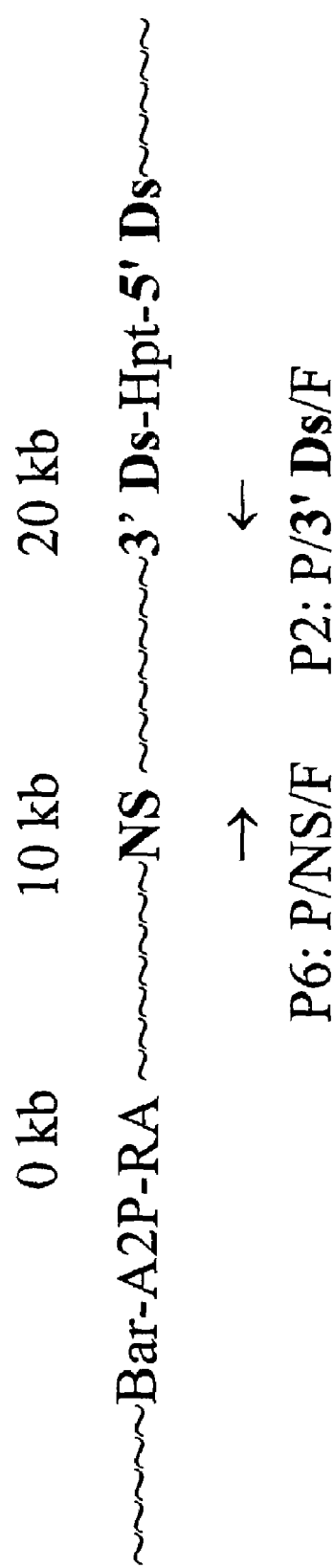

FIG. 25 shows how subline walking is used to determine distances of sequences that are transposed between 10 and 20 kb from the anchor position. Primers "P6" and "P2," used to determine the distance between the flanking sequence "NS" and the Ds element in plant "A2-3-7A," are indicated below the diagram.

Figure 9:
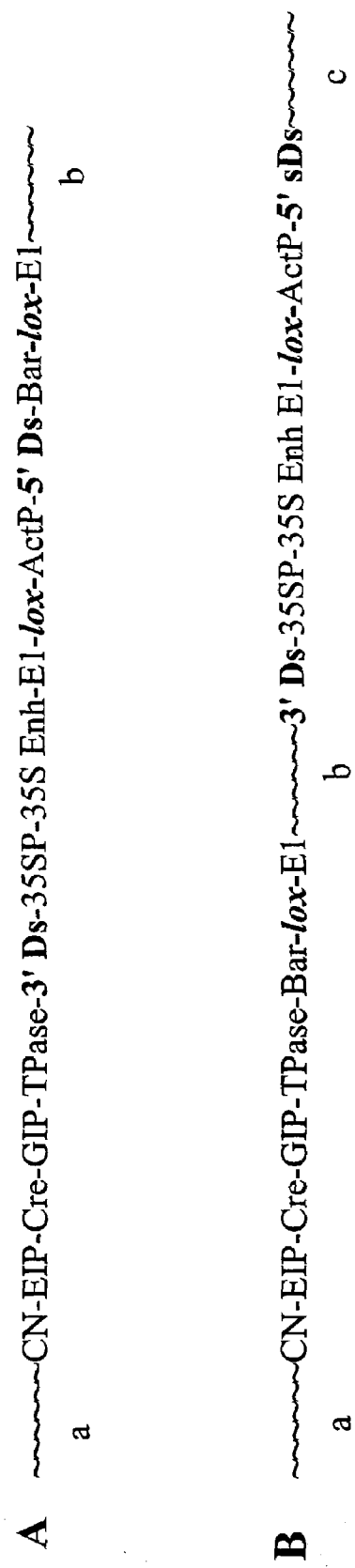
FIGS. 9A–B show the use of a Cre-lox system to delete a DNA segment from the genome of a transposant using an activation plasmid of the present invention.
Figure 26:
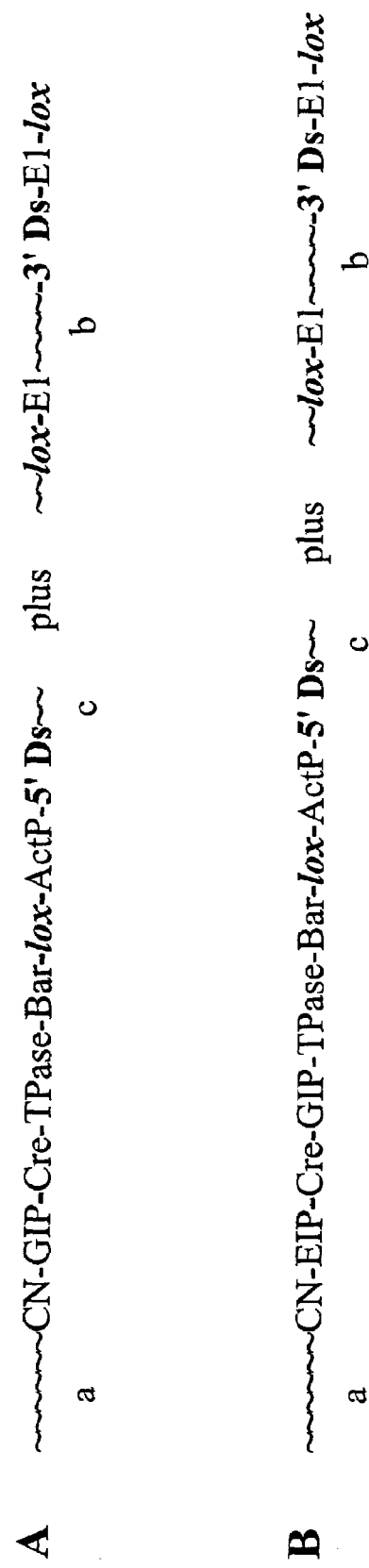

FIGS. 26A–B show the results of Cre-directed recombination starting with the structures shown in FIGS. 9A–B. The left-hand side of the structure in FIG. 26A shows the product after CRE splices each lox site of FIG. 9A, and re-joins the spliced half-lox sequences. The structure shown on the right hand side of FIG. 26A contains chromosomal fragment "b," and exists as a circular DNA by joining the two half-lox sequences. FIG. 26B shows the products after Cre-directed recombination starting with the structure shown in FIG. 9B.

FIGS. 27A–F show an exemplary transgenic plant of the third embodiment of the present invention "A2-3-7A," and the steps involved in utilization of the lox-site containing sequence in the T-DNA integrated in the transgenic plant. FIG. 27A shows the portion of an enhancer-trap, gene-trap containing gene-disruption transformation plasmid with a Ds transposon element including a lox sequence, indicated by "lox." FIG. 27B shows the same plasmid in the chromosome of "A2-3-7A," following transformation. The wavy lines designated "a" and "b" indicate chromosomal DNA on either side of the integrated plasmid. FIG. 27C shows the transposition site of the plasmid in "A2-3-7A," following the transposition event. FIG. 27D shows the that gene "Y" is disrupted by the plasmid to give "Y1" and "Y2." FIG. 27E shows an abbreviated Cre-containing plasmid that also contains in intact "Y" gene. "BS" is the pBluescript vector, "EIP" is the estradiol-activated inducible promoter. FIG. 27F shows the integration of plasmid in FIG. 27E into the structure shown in plasmid of FIG. 27D, thereby introducing an intact gene "Y" into the transgene plant.

DETAILED DESCRIPTION OF THE INVENTION

The first embodiment of the present invention relates to a method of constructing a non-redundant, saturation, gene-disruption plant library. This involves providing a plasmid having two clusters of unique restriction enzyme-cutting sites and two dissociation elements, and transforming a plurality of plants with the plasmid to produce a plurality of transformed plants with the plasmid integrated at different locations within the genome of the plants. Next, the locations of the integrated plasmid in the transgenic plants are mapped to identify anchor transgenic plant lines with the integrated plasmid suitably spaced within the genome of the plants. "Anchor" as used herein refers to the site of insertion of the plasmid due to the transformation event, and is used subsequently to assess the movement of the transposon following the later transposition event.

Each of the homozygous anchor transgenic plant lines is then crossed with a plant having an activator element to form progeny plants. The crossing activates transposition of the two dissociation elements to form a plurality of progeny plants having different genes disrupted by the insertion of the re-located Ds-containing element. Next, the method of the present invention involves digesting the plant genome at different unique enzyme-cutting sites to release a DNA fragment from each of the transgenic progeny plants, and measuring the size of each of the released DNA fragments to determine transposition distances in each of the transgenic progeny plants. Next, progeny transgenic plants are selected with the transposition distances which are different from the transposition distances of the other progeny transgenic plants by a pre-determined amount to prepare a non-redundant, saturation, gene-disruption plant library.

The present invention also relates to a plasmid having an insert containing two dissociation elements and two clusters of unique enzyme-cutting sites. One cluster of unique enzyme-cutting sites is between the two dissociation elements in the insert, and the second cluster of unique enzyme-cutting sites is not between the two dissociation elements in the insert. The present invention also relates to plant cells and plants transformed with the plasmid of the present invention, and the progeny thereof.

In accordance with this aspect of the present invention, two exemplary Ds-containing "super plasmids" were constructed. Each plasmid contains two maize Ds elements and two clusters of relatively rare enzyme-cutting sites, which allows the construction of non-redundant, saturation, gene-disruption plant libraries. As used herein, "rare" means "infrequently occurring, uncommon." (The American Heritage College Dictionary, p. 1132, 3 ed. Houghton Mifflin Co., New York (1993), which is hereby incorporated by reference in its entirety). This generally involves inserting the desired the nucleic acid molecules into an expression system to which the nucleic acid molecules are exogenous (i.e., not normally present). The exogenous nucleic acid molecules are inserted into an expression system which includes the necessary elements for the transcription and translation of the inserted protein coding sequences. While different components can be combined to create a plasmid with the ability to transform various types of plants (monocots and dicots) and animals, the plasmids of the invention are generally constructed as follows. Table 1 provides a list of abbreviations for the components of the plasmids to be described herein.

TABLE 1

| Abbreviation | Represents |
| --- | --- |
| 3 or 3SA | Triple splice acceptor sequence from a rice gene |
| 35P | CaMV 35S promoter |
| 35T | CaMV 35S 3' terminator sequence |
| Ac | Activation sequence of maize |
| A4P | Rice Actin 4 promoter |
| AAI | *Arabidopsis* Act2 intron |
| AAP | *Arabidopsis* Act2 promoter, or a similar strong promoter for dicot plants |
| AI | Rice Actin 1 intron (Act1 intron) |
| AAMP | *Arabidopsis* Act2 minimal promoter |
| AP or Act Pro | Rice Actin 1 promoter or a similar strong promoter from a cereal plant |
| Act100 P or RAMP | Rice Actin-100 minimal promoter |
| Bar | Phosphinothricin acetyl transferase gene to confer herbicide resistance |
| Cah | Cyanamide hydrolase gene |
| CN | A partially deleted single-copy gene in the genome for rapid PCR-based copy number analysis; for rice, a 132-bp segment of cytochrome c gene is shortened to 107 bp |
| Ds | Dissociation sequence of maize |
| DMIP or GIP | Dexamethasone inducible promoter |
| E | A restriction enzyme recognition sequence, which is rare in the genome |
| GapP or Gapc Pro | *Arabidopsis* cytoplasmic glyceraldehyde 3-P dehydrogenase promoter |
| GFP | Green Fluorescent Protein marker for visible selection |
| GIP | Glucocorticoid inducible promoter |
| Gus | β-glucuronidase gene |
| Hyg | Hygromycin phosphotransferase gene for selection |
| I or Ipo | Synthetic oligonucleotide sequence including the 15-bp recognition sequence of I-PpoI; where I-PpoI is an intron-encoded endonuclease |
| IAAH | A gene that encodes an enzyme to convert naphthalene acetamide (NAM) to naphthalene acetic acid |
| L | A chicken lysozyme matrix attachment region (MAR) sequence |
| Lox or loxP | 34 bp Cre recombinase recognition sequence |

TABLE 1-continued

| Abbreviation | Represents |
| --- | --- |
| M or CN | A partially deleted single-copy gene in the genome for rapid PCR-based copy number analysis; for rice, a 132-bp segment of cytochrome c gene is shortened to 107 bp |
| MAR | Matrix attachment region used to enhance the expression of TPase. |
| NosT | Nopaline synthase (Nos) 3' terminator sequence |
| N or Not | NotI restriction enzyme recognition sequence; when more than one identical restriction enzyme recognition sequence, such as N, is present, they are designated as N1, N2, etc. |
| NPTII | Neomycin phosphotransferase II gene |
| Pin2 | Potato proteinase inhibitor II gene |
| PinP | Potato proteinase inhibitor II promoter |
| PinT | Potato proteinase inhibitor II 3' terminator sequence |
| P or Pro | Promoter |
| S or Sma | SmaI recognition sequence |
| T | 3' terminator sequence |
| TMAR | Tobacco matrix attachment region sequence used to enhance the expression of TPase. |
| TPase | Ac transposase gene |
| UP or UbiP | Maize ubiquitin promoter or a similar strong promoter from a cereal plant |
| V | Plasmid vector such as pCAMBIA1300, which includes the left border (LB) and right border (RB) sequence of T-DNA, or the plasmid pBluescript SK |

Figure 1:
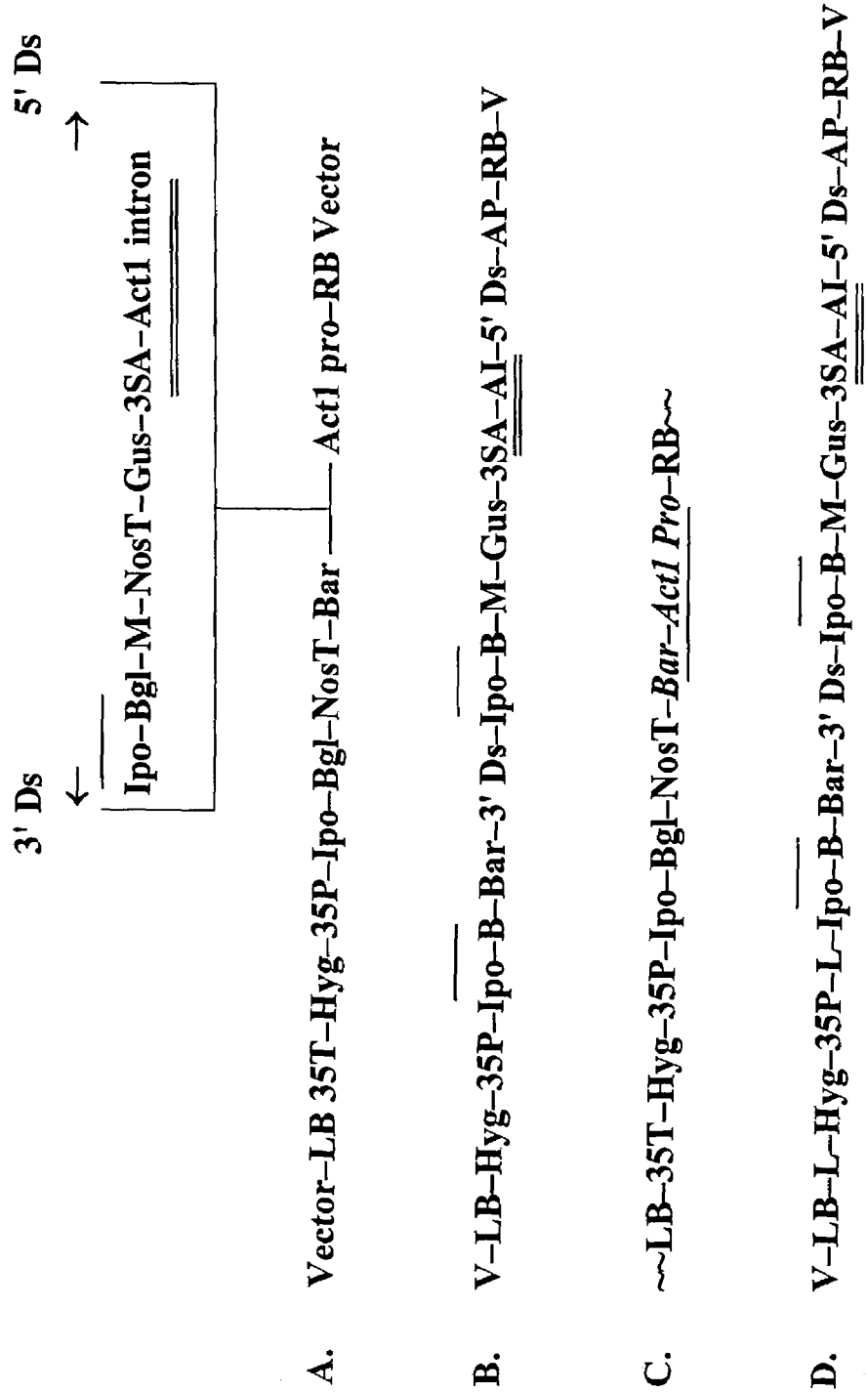
FIGS. 1A–D show the components of the super gene-trap plasmid, pSDsG.

The introduction of a gene into host cells is facilitated by first introducing the gene sequence into a suitable nucleic acid vector. "Vector" is used herein to mean any genetic element, such as a plasmid, phage, cosmid, chromosome, virus, virion, etc., which is capable of replication when associated with the proper control elements and which is capable of transferring gene sequences into cells. Thus, the term includes cloning and expression vectors, as well as viral vectors, including adenoviral and retroviral vectors. Suitable vectors for embodiments involving the transformation of plants, for example, include pCAMBIA 1300, which includes the left border ("LB") and right border ("RB") sequence of T-DNA, and the phagemid pBluescript SK (Stratagene, La Jolla, Calif.). The plasmid is then constructed in such a way as to be useful for the species of the genome under study. The most important feature of this series of novel super plasmids of the first embodiment of the present invention is the inclusion of two identical clusters of enzyme recognition sequences placed in strategic locations in each super plasmid. This is because after transformation with a super plasmid to produce anchor plant lines, and Ac/Ds-mediated transposition in transgenic plants, the distance of transposition can be quickly and accurately measured (using enzyme digestion and gel electrophoresis) between the original anchor position and the newly transposed position in each plant line. The placement of the two clusters of enzyme recognition sites in the transformation plasmid is crucial. One cluster is located within the boundaries, i.e., the 5', 3' ends, of the transposable element, and an identical cluster is located in the plasmid outside of the boundaries of the transposable element, as seen in FIG. 1A.

FIG. 1A is an expanded view of an exemplary Ds-containing plasmid, pSDsG, designed for monocot transformation. FIG. 1B shows the same plasmid in an abbreviated form. As shown in FIG. 1C, when transposition occurs, the portion of the integrated plasmid that is within the boundaries of the Ds element relocates to another site on the chromosome of the transgenic organism, in this case bringing the Bar gene adjacent to the Act1 promoter. The rest of the plasmid outside the boundaries of the transposable element remains at the anchor site. The distance between the anchor site (where the rest of the plasmid remains) and the relocation site of the transposable element is the "transposition distance." The transposition distance of any transposon can then be determined by digesting the plant genome with one or more of the restriction enzymes present in the two clusters of enzyme recognition sites. The fragment size can be resolved by gel electrophoresis, thereby allowing the determination of the distance, in kb, that the transposable element has moved from the anchor site during transposition. Exemplary restriction sites include, but are not limited to, I-PpoI, I-CeuI, AscI, NotI, PmeI, ApaI, BglI, and SmaI.

The plasmids of the first embodiment may also include a gene-trap or enhancer-trap feature that includes a β-glucuronidase gene (Gus) (Jefferson, "Assaying Chimeric Genes in Plants: The GUS Gene Fusion System," *Plant Mol. Biol. Reporter* 5:387–405 (1987), which is hereby incorporated by reference in its entirety), or any other suitable reporter gene-containing cassette that allows visualization of expression in the transgenic plants after transposition, even though there may not be readily detectable phenotypic changes in those plant lines. Thus, the gene-trap and enhancer-trap libraries are not only knockout libraries, but also have the additional feature of tagging and identifying plant lines and genes that have no visible phenotype. A partially deleted endogenous gene segment (designated as "M" or "CN" herein) is also included in the plasmid, so that the transgene copy number in each plant, as well as the homozygosity of second or third generation plant lines, can be easily and rapidly determined by a PCR method. Finally, a selectable marker cassette, e.g., CaMV 35S promoter-Hyg (hygromycin phosphotransferase gene), is included for selection of transformed calli during transformation and regeneration of the plants. A second selectable marker cassette, e.g., Act1 promoter-Bar, is activated only after transposition, as shown in FIG. 1C.

In the gene-trap system (also known as promoter-trap and exon-trap), the plasmid has no promoter. When a gene-trap plasmid disrupts a gene, it can detect the expression of a chromosomal gene (using the Gus reporter) when the Ds-containing segment is inserted within a transcribed region (including the introns) or the promoter region on the chromosome. Thus, the expression of Gus depends on the promoter in the chromosome adjacent to the re-insertion location of the Ds-containing portion of the integrated plasmid. FIGS. 1A–D show the structure of a super gene-trap plasmid, pSDsG, for transformation of rice.

Promoters are chosen for inclusion in the construct in relation to the function of the particular plasmid. Promoters vary in their "strength" (i.e., their ability to promote transcription). For the purposes of expressing a cloned gene, it is usually desirable to use strong promoters in order to obtain a high level of transcription and, hence, expression of the gene. Suitable "strong" promoters for inclusion on the construct of the present invention for plants include, but are not limited to, the maize ubiquitin promoter (ubi) or a similar strong promoter from a cereal plant such as rice actin1 promoter (Act1 Pro) or the CaMV 35S promoter and the glyceraldehyde 3-P dehydrogenase promoter of *Arabidopsis* (GapP). In some instances, a weak, or "minimal" promoter is preferable, such as in the construct of the present invention known as a super enhancer-gene, described in further detail herein. Other examples of promoters appropriate for the plasmids of the present invention are shown in Table 1 and further described below.

The plasmid of the present invention also includes an operable 3' terminator, selected from among those which are capable of providing correct transcription termination and polyadenylation of mRNA for expression in the host cell of choice, operably linked to a DNA molecule which encodes for a protein of choice. A number of 3' terminators are known to be operable in plants. Exemplary 3' terminators include, without limitation, those from the nopaline synthetase gene ("Nos") (Fraley, et al., "Expression of Bacterial Genes in Plant Cells," Proc. Nat'l Acad. Sci. USA 80:4803–4807 (1983), which is hereby incorporated by reference in its entirety), the cauliflower mosaic virus "CaMV 35S" gene (Odell, et al., "Identification of DNA Sequences Required for Activity of the Cauliflower Mosaic Virus 35S Promoter," Nature 313(6005):810–812 (1985), which is hereby incorporated by reference in its entirety), rice actin 1 gene ("Act1"), potato proteinase inhibitor II gene ("Pin2") for plants, and the simian virus ("SV40") polyA region for animals. Many 3' terminators known to be operable in a given organism of interest are suitable for proper expression of the coding sequence of the DNA constructs of the present invention.

The vector of choice, enzyme recognition clusters, promoters, Ac or Ds elements, reporter cassettes, selection cassettes, and an appropriate 3' terminator can be ligated together to produce the Ac/Ds plasmids of this first embodiment of the present invention using well known molecular cloning techniques as described in Sambrook et al., Molecular Cloning: A Laboratory Manual, Second Edition, Cold Spring Harbor Press, NY (1989), which is hereby incorporated by reference in its entirety.

FIG. 1A and FIG. 1D show the structure of an exemplary super gene-trap plasmid, pSDsG, of the present invention for transformation of rice (Sundaresan et al., "Patterns of Gene Action in Plant Development Revealed by Enhancer Trap and Gene Trap Transposable Elements," *Genes &Develop.* 9:1797–1810 (1995), which is hereby incorporated by reference in its entirety). The gene-trap plasmid is designed to disrupt a gene and then detect the expression of a chromosomal gene using a visible marker gene (Gus or gfp reporter, for example) when the Ds-containing segment is inserted within a transcribed region on the chromosome. The expression of the reporter gene depends on the promoter in the chromosome. FIG. 1A shows plasmid pSDsG for rice or monocot transformation. Note that the recognition sequences of two enzymes, Ipo-Bg1 (shown in FIG. 1A with a line on top of these sequences), represent only some of the recognition sequences. "Ipo" is a synthetic oligonucleotide sequence including the 15-bp recognition sequence of 1-PpoI; where I-PpoI is an intron-encoded endonuclease (Muscarella et al., "Characterization of I-Ppo, an Intron-Encoded Endonuclease that Mediates Homing of a Group I Intron in the Ribosomal DNA of *Physarum polycephalum*," *Mol. Cell Biol.* 10:3386–3396 (1990), which is hereby incorporated by reference in its entirety). Many more recognition sequences are actually included in the plasmid, such as I-PpoI, I-CeuI, AscI, NotI, PmeI, ApaI, BglI, and SmaI. The plasmid also includes a CaMV 35S promoter, the hygromycin phosphotransferase gene for selection purposes, a Bar gene to confer herbicide resistance, maize Ds transposon recognition sequences (i.e., 3' and 5' Ds), a Gus gene for selection purposes, a rice Actin1 intron, and an rice Actin1 promoter, all which are operably fused into a plasmid vector. As can be seen in FIG. 1C, after transposition the Bar gene is adjacent to the Act1 promoter, and thus Bar is activated and can synthesize phosphinothricin acetyl transferase to make the rice plant resistant to the herbicide glufosinate ammonium (available commercially as "Basta"). This constitutes an easy and rapid way of recognizing a transposition event that is low in frequency (around 3–15%). This means that out of 100 F2 plants, transposition may have occurred in only 3 to 15 plants.

FIG. 1B is an abbreviated view of the components of pSDsG, shown without 3' terminators. After integration of this plasmid in the rice genome and after transposition, the remaining part of the plasmid, including the empty site, has the abbreviated structure shown in FIG. 1C. FIG. 1D shows a similar plasmid with two lysozyme matrix attachment regions (L) added to enhance the expression of selectable marker gene (Hyg).

An example of a super enhancer-trap plasmid of the present invention, pSDsE, is shown in FIG. 2. In the enhancer-trap system, the plasmid has a minimal promoter that only expresses when inserted near a cis-acting enhancer in the chromosome. The pSDsE enhancer-trap plasmid includes a Gus gene, fused to a rice Act1-100 minimal promoter ("RAMP"). The Gus gene under control of the minimal promoter RAMP provides the enhancer-trap feature. The super enhancer-trap plasmid is designed so that expression of the Gus reporter gene is dependent on its insertion near chromosomal enhancer elements. Enhancer elements are DNA sequences located considerably up- or downstream from the normal "startpoint" of a gene. Enhancer regions contain elements that bind transcription factors or related proteins. Most important is the fact that enhancer elements are not dependent on location for functionality. Enhancers can work bi-directionally, stimulating any promoter placed in the vicinity of the enhancer, even at a considerable distance from the gene's constitutive promoter. This is important because transposon elements can "flip" during transposition, and may reinsert in the reverse orientation, i.e., 3'Ds→5'Ds, rather than 5'Ds→3'Ds. Thus, regardless of the orientation of the enhancer-trap plasmid following transposition (3'Ds→5'Ds or 5'Ds→3'Ds), or the distance (usually between 0.2 and 6 kb) from the transposition site, the reporter gene is activated and can be identified using the substrate 5-bromo-4-chloro-3-indolyl β-D-glucuronide (X-Gluc) according to the method described by Jefferson, "Assaying Chimeric Genes in Plants: The GUS Gene Fusion System," *Plant Mol. Biol. Reporter* 5:387–405 (1987), which is hereby incorporated by reference in its entirety. The enhancer-trap plasmid of the present invention is designed to take advantage of the presence of endogenous enhancer elements in the target genome. The Gus gene of the enhancer-trap plasmid is fused to a minimal promoter derived from any suitable source. For example, a rice Act1-100 minimal promoter can be used for monocots, and a 47-bp minimal 35S promoter of CaMV can be used for dicots, as seen in FIG. 2. Transposition of the Ds element to a site proximal to an enhancer region activates the promoter, allowing for identification of the transgenic plant by increasing the expression of the Gus genes. The super enhancer-trap plasmids share the same advantage of the super gene-trap plasmids in that the exact distance between the anchor site and the newly transposed site can be easily and accurately measured in a transgenic plant.

Using the gene-trap and enhancer-trap containing plasmids in concert doubles the chances of tagging different genes in genome of a given transformed host cell, thereby reducing the number of transformed units to be analyzed.

FIGS. 3A–B show the components of exemplary plasmids pSDsG and pSDsE for transformation of dicots such as *Arabidopsis*. FIG. 3A is an abbreviated super gene-trap plasmid, pSDsG, useful for dicot transformation. The pSDsG plasmid includes the 35S CaMV minimal "35P" promoter (Hayashi et al., "Activation of a Plant Gene by T-DNA Tagging: Auxin-Dependent Growth In Vitro," *Science* 258: 1350–1353 (1992), which is hereby incorporated by reference in its entirety), or the cytoplasmic glyceraldehyde 3-P dehydrogenase promoter of *Arabidopsis* to replace the maize ubiquitin promoter; the *Arabidopsis* Act2 intron ("AAI") is used to replace the rice Act1 intron, and the *Arabidopsis* Act2 promoter ("AAP") is included in the Ds element to replace the rice Act1 promoter. In addition, the T-DNA left border (LB) and right border (RB) are always used to flank the plasmid, which are joined to the vector part of the plasmid as shown in FIGS. 3A–B. If the vector is pCAMBIA 1300, the LB and RB are included automatically. FIG. 3B shows an exemplary abbreviated super enhancer-trap plasmid, pSDsE, for dicot transformation, where AAMP is the *Arabidopsis* Act2 minimal promoter. In each plasmid Gus is under the control of a minimal promoter, providing the gene-trap feature in the plasmid.

In addition to the Ds plasmids disclosed above, the present invention relates to an Ac-containing plasmid for plant transformation. FIGS. 4A–C show representative Ac-containing plasmids in abbreviated format. FIG. 4A is an Ac-containing plasmid for transforming monocots such as rice, where TMAR is a tobacco matrix attachment region sequence, and TPase is the maize Ac transposase gene and flanking sequences. The TMAR sequence acts as an enhancer, and therefore does not require its own promoter or 3' regulatory element. TMAR enhances the activity of any promoter that is nearby. The inclusion of the TMAR sequence increases the level of expression of the TPase gene and minimizes the chance of gene silencing (Spiker et al., "Nuclear Matrix Attachment Regions and Transgenic Expression in Plants," *Plant Physiol.* 110:15–21 (1996); and Holmes-Davis et al., "Nuclear Matrix Attachment Regions and Plant Gene Expression," *Trends in Plant Science* 3:91–96 (1998), which are hereby incorporated by reference in their entirety). IAAH is an indole acetic acid hydrolase gene; it is used to eliminate plants that still harbor the Ac-containing plasmid after crossing an Ac-plant with a Ds-plant and allowing the progeny to segregate (Sundaresan et al., "Patterns of Gene Action in Plant Development Revealed by Enhancer Trap and Gene Trap Transposable Elements," *Genes &Develop.* 9:1797–1810 (1995), which is hereby incorporated by reference in its entirety).

FIG. 4B is an Ac-containing plasmid with an inducible promoter for co-transformation of monocots, where GIP is the glucocorticoid (dexamethasone) inducible promoter (Aoyama et al., "A Glucocorticoid-Mediated Transcriptional Induction System in Transgenic Plants," *Plant J.* 11: 605–612 (1997), which is hereby incorporated by reference in its entirety). When the plasmid shown in FIG. 4B is used for transformation, the Ac transposase gene is not expressed until the plants are sprayed with dexamethasone. Other inducible promoters that may be used in place of GIP include, but are not limited to, an estrogen-inducible promoter EIP (Bura et al., "Expression Profiling of the Maize Flavonoid Pathway Genes Controlled by Estradiol-Inducible Transcription Factors CRC and P," *Plant Cell* 12:65–80 (2000); (Zuo et al., "An Estrogen Receptor-Based Transactivator XVE Mediates Highly Inducible Gene Expression in Transgenic Plants," *Plant J.* 24:265–273 (2000), which are hereby incorporated by reference in their entirety), and TetR, a tetracycline-inducible (depressible) promoter (Gatz et al., "Promoters That Respond to Chemical Inducers," *Trend Plant Sci.* 3:352–358 (1998), which is hereby incorporated by reference in its entirety). Other suitable features are identified in Table 1, above.

The Ac-containing plasmid shown in FIG. 4C is suitable for transforming dicots such as *Arabidopsis* in the present invention includes the Ac-containing plasmid published by Sundaresan et al., "Patterns of Gene Action in Plant Development Revealed by Enhancer Trap and Gene Trap Transposable Elements," *Genes and Develop.* 9:1797–1810 (1995), which is hereby incorporated by reference in its entirety; the plasmid also includes two tobacco MAR sequences to increase the level of TPase expression.

In addition to the maize Ac/Ds system to produce a gene-disruption library, other transposable elements, such as Mu (for a review, see Walbot, "Strategies for Mutagenesis and Gene Cloning Using Transposon Tagging and T-DNA Insertional Mutagenesis," *Annu. Rev. Plant Physiol. Plant Mol. Biol.* 43:49–82 (1992), which is hereby incorporated by reference in its entirety), En/Spm (for a review, see Federoff, "Maize Transposable Elements," Berg., eds., *Mobile DNA*, pp. 375–411 (1989), which is hereby incorporated by reference in its entirety), are suitable for the preparation of the plasmids in this embodiment of the present invention.

A further aspect of the present invention relates to a host cell which contains one or more plasmids of the present invention. As described more fully hereinafter, the host cell can be either a bacterial cell (e.g., *Agrobacterium*), a plant cell or an animal cell. There are several methods of transformation of host cells known to those skilled in the art. The biolistic method (Cao et al., "Regeneration of Herbicide-Resistant Transgenic Rice Plants Following Microprojectile-Mediated Transformation Suspension Cells," *Plant Cell Reports* 11:586–591 (1992), which is hereby incorporated by reference in its entirety), which is also known as particle bombardment (U.S. Pat. Nos. 4,945,050, 5,036,006, and 5,100,792, all to Sanford, et al., which are hereby incorporated by reference in their entirety), or the *Agrobacterium*-mediated method (Hiei et al., "Efficient Transformation of Rice (*Oryza sativa* L) Mediated by *Agrobacterium* and Sequence Analysis of the Boundaries of the T-DNA," *Plant J.* 6:271–282 (1994), which is hereby incorporated by reference in its entirety) are well suited for the transformation of rice, as well as many other plants. Recombinant constructs can also be introduced into cells via transduction, conjugation, mobilization, protoplast fusion, electrofusion, or electroporation (Fromm, et al., *Proc. Natl. Acad. Sci. USA,* 82:5824 (1985); Stark et al., "Forward Genetics in Mammalian Cells: Functional Approaches to Gene Discovery," *Human Molecular Genetics* 8:1925–1938 (1999), which are hereby incorporated by reference in their entirety). Other variations of transformation, now known to those skilled in art, or hereafter developed, can also be used. Suitable host cells include, but are not limited to, bacterial, viral, mammalian, insect, plant, and the like. Because the method of the present invention is particularly suited to reducing the time and labor spent reaching a functional understanding of the genome to which it is applied, many plants are suitable target cells for the method. These include, but are not limited to, cereal crop plants, such as barley, maize, and wheat; vegetables, such as soybeans, tomatoes, and broccoli; also flowers, and fruit trees.

Following transformation, the cells are grown on a selective medium. Preferably, transformed cells are first identified using a selection marker simultaneously introduced into the host cells along with the plasmid of the present invention. Suitable selection markers include, without limitation, markers coding for antibiotic resistance, such as the nptII gene which confers kanamycin resistance (Kan$^R$)(Fraley, et al., Expression of Bacterial Genes in Plant Cells," *Proc. Natl. Acad. Sci. USA*, 80:4803–4807 (1983), which is hereby incorporated by reference in its entirety); the IAAH gene, which confers resistance to naphthalene acetamide ("NAM") (Sundaresan et al., "Patterns of Gene Action in Plant Development Revealed by Enhancer Trap and Gene Trap Transposable Elements," *Genes &Develop.* 9:1797–1810 (1995), which is hereby incorporated by reference in its entirety); the dhfr gene, which confers resistance to methotrexate (Bourouis et al., Vectors Containing a Prokaryotic Dihydrofolate Reductase Gene Transform *Drosophila* Cells to Methotrexate-Resistance," *EMBO J.* 2(7):1099–1104 (1983), which is hereby incorporated by reference in its entirety); and the Hyg gene, which confers resistance to hygromycin. Any known antibiotic-resistance marker can be used to transform and select transformed host cells in accordance with the present invention. Cells or tissues are grown on a selection media containing an antibiotic, whereby generally only those transformants expressing the antibiotic resistance marker continue to grow. Similarly, enzymes providing for production of a compound identifiable by color change are useful as visible selection markers, such as Gus, and gfp, or luminescence, such as luciferase.

Two approaches for transformation are involved in the first embodiment of the present invention. In the first approach, a first group of plants is transformed with Ds-containing plasmid of the present invention, and a second group is transformed with an Ac-containing plasmid of the present invention, each element of the transposon system under the control of a constitutive promoter. In the second approach, a group of plants are co-transformed with two plasmids, one a Ds-containing plasmid and the other an Ac-containing plasmid. These plasmids are prepared generally as described above; however, the transposase gene in the Ac-containing plasmid of this aspect of the present invention is under the control of an inducible promoter, for example, GIP, as shown in FIG. 4B. Thus, transposase gene expression can be controlled to allow transposition of the Ds-containing plasmid in the same transgenic plant at the desired time. Transformed plants are allowed to regenerate, and organisms or cells are cultured in suitable medium until stabilized. The copy number of the transgene in each cell, cell line, or T0 plant is determined using PCR methodology. Plants with only one or two copies of each transgene are chosen for further analysis. One copy of the transgene is preferable, because it is simpler to analyze the gene disruption when only one copy is present in a transposant. However, when two copies are present, it may be possible to reduce the total number of anchor plants needed to analyze the genome, because one plant can be used for the analysis of the disruption of two genes rather than just one. Therefore, whenever one copy of a transgene is suggested herein, it means that two copies are also acceptable, for all embodiments of the present invention described herein.

In the first approach, after transformation, the first step is to generate Ds-plasmid-containing anchor plant lines (primary gene-disrupted mutant plant lines); for example, approximately 150 lines are needed for *Arabidopsis*, and 500 for rice. The experimental design allows one to rapidly select one anchor plant line for approximately every 0.8–1.2 megabase pairs of chromosomal DNA. After producing homozygous anchor plant lines, each line is crossed with an Ac-plasmid-containing plant to activate transposition of the Ds-containing plasmid in the F1 and F2 generation plants.

In the second approach, after homozygous plants are produced and Ds plasmid location mapped, the inducible promoter is activated by the appropriate chemical/procedure to allow expression of the transposase gene, which then catalyzes transposition. Next, the locations of the integrated plasmid in the transgenic plants are mapped to identify anchor transgenic plants lines with the integrated plasmid suitably spaced within the genome of the plants. Next, the method of the present invention involves digesting the plant genome at one of the different enzyme-cutting sites to release a DNA fragment from each of the transgenic progeny plants, and measuring the size of each of the released DNA fragments to determine transposition distances in each of the transgenic progeny plants. Restriction digestion is carried out using the manufacturer's recommended method for a given enzyme, or according to those methods well-known in the art. Next, the present invention involves selecting progeny transgenic plants with transposition distances which are different from the transposition distances of the other progeny transgenic plants by a pre-determined amount to prepare a non-redundant, saturation, gene-disruption plant library.

The present invention also relates to another method of constructing a non-redundant, indexed, saturation, gene-disruption genomic library of an organism. This method involves providing a first plasmid that includes a transposon-specific recognition sequence having 5' and 3' ends which form the boundaries of the transposon-specific recognition sequence, and 2 clusters of restriction enzyme recognition sites. One cluster is located inside the boundaries of the transposon-specific recognition sequence and the second cluster is located outside the boundaries of the transposon-specific recognition sequence. The enzyme recognition sites in one cluster are identical to the enzyme recognition sites in the second cluster but the enzyme recognition sites in both clusters either do not exist or are rare in the organism in which the library is being constructed. This first plasmid also has one or more promoter elements operably linked to each gene in the plasmid, and one or more 3' terminator elements operably linked 3' to each gene in the plasmid. The plasmid also contains one or more first selection marker genes located inside the boundaries of the transposon recognition sequence and operably linked to a promoter element and a 3' terminator element. Also included in the plasmid are one or more detection genes, where at least one of the one or more detection genes is located inside the boundaries of the transposon recognition sequence, and is operably linked to a promoter element and a 3' terminator element. A second plasmid is also provided, having a transposase gene that is operably linked to at least one promoter element and to a 3' terminator element. This plasmid also has one or more second selection marker genes, with each selection marker gene operably linked to a promoter element and a 3' terminator element and where the first selection marker gene is different from the second selection marker gene. A plurality of organisms are co-transformed with the first plasmid and the second plasmid to produce a plurality of co-transformed anchor transgenic organisms with the first and second plasmids integrated at different sites within the transgenic organism's genome. The integration site of a first plasmid due to transformation is defined as a plasmid's anchor location. A plurality of transgenic anchor organisms are selected, each having one copy of the first and second plasmid integrated into the genome. An anchor location for each integrated first plasmid in the plurality of transgenic organisms is mapped to identify anchor transgenic lines, each identified anchor transgenic line harboring a first plasmid within its genome at a location at least 200–600 kilobases away from the location of a first plasmid in the other anchor transgenic lines. Transposition is allowed to occur to produce a plurality of transposants having different genes disrupted. The transposon-specific recognition sequence of the first plasmid has transposed from its anchor location to a different reintegration location in the transposant's genome, which defines a "transposition distance" between the anchor location and the reintegration location. Next, the transposition distances of the transposed transposon-specific recognition sequences is determined in a plurality of transposants resulting in a given anchor line. A plurality of transposants are then selected, each having a transposition distance that is different from the transposition distances of the other transposants to prepare a non-redundant, indexed, saturation, gene disruption library in an organism.

The present invention utilizes two-component transposition systems because they can be readily controlled and manipulated, and are particularly useful transposon systems because they do not require host-specific factors for transposition. Two-component systems include a transposase enzyme and a specific flanking sequence for recognition by the transposase to initiate transposition. The transposon-specific recognition sequence suitable for the first plasmid of this aspect of the present invention may be from any two-component transposon system. "Specific" as used herein means that the transposon recognition sequence will be recognized by the transposase gene chosen for integration in the second plasmid of this aspect of the present invention. Choice of a transposon system will be dictated by the choice of organism. The following systems have been shown to work in heterologous organisms. For plants (and some animal cell lines), the maize Ac/Ds, and En/Spm systems are among the most useful (Bancroft et al., "Transposition Pattern of the Maize Element Ds in *Arabidopsis thaliana*," *Genetics* 134:1211–1229 (1993); and Walbot, V., "Saturation Mutagenesis Using Maize Transposons," *Curr. Opin. In Plant Biol.* 3:103–107 (2000), which are hereby incorporated by reference in their entirety). For animals, including humans, the Sleeping Beauty (SB) transposon system of zebrafish and the Tc1 and Tc3 of *C. elegans* are among the most useful (Fischer et al., "Regulated Transposition of a Fish Transposon in the Mouse Germ Line," *Proc. Natl. Acad. Sci. USA* 98: 6759–6764 (2001), which is hereby incorporated by reference in its entirety). Also suitable is the mariner element isolated from *Drosophila mauritiana*, which has been proposed for use in a wide range of eukaryotes (Fadool et al., "Transposition of the Mariner Element from *Drosophila Mauritania* in Zebrafish," *Proc. Natl. Acad. Sci. USA* 95:5182–5186 (1998), which is hereby incorporated by reference in its entirety). Other transposon systems now used or later identified are also suitable for use in the present invention. The "transposon-specific recognition sequence" used in this embodiment corresponds to the "Ds", or "dissociation" element, of the maize transposon system described above, and the 5' and 3' ends correspond to the "two dissociation elements" described in the first embodiment herein.

The two clusters of enzyme recognition sites in the first plasmid provided in this aspect of the present invention are identical in composition, but the enzyme recognition sites in both clusters either do not exist or are rare in the organism in which the library is being constructed. When the genome of the organism in which the gene disruption library is being constructed is known, the restriction enzyme recognition sites to be included in the transformation plasmid clusters can be chosen so that those same sites are either not present or are rare in the genome of the organism of interest. When the genome is not wholly known, using rare enzyme recognition sites reduces the possibility that the sites in the transformation plasmid will be present in the organism of interest. Exemplary restriction sites include, without limitation, I-PpoI, I-CeuI, AscI, NotI, PmeI, ApaI, BglI, and SmaI.

Suitable selection markers for the first and second plasmids of this aspect of the present invention include those described above, including those that confer antibiotic resistance or herbicide resistance. Exemplary selection markers include, without limitation, Hpt, hygromycin phosphotransferase gene, which confers resistance to the antibiotic hygromycin; Bar, the phosphinothricin acetyltransferase gene, which confers resistance to the herbicide phosphinothricin ("PPT"); IAAH, the indoacetic acid hydrolase gene; Cah, a cyanamide hydrolase gene (Maier-Greiner et al., "Isolation and Properties of a Nitrile Hydratase from the Soil Fungus *Myrothecium verrucaria* that is Highly Specific for the Fertilizer Cyanamide and Cloning of its Gene," *Proc. Natl. Acad. Sci. USA* 88:4260–4264 (1991), which is hereby incorporated by reference in its entirety); Amp, the ampicillin resistance gene; Neo, the neomycin phosphotransferase gene; and Puro, the puromycin acetyltransferase gene, and any others known in the art. Other suitable selection markers include, without limitation, those shown in Table 2, below, and those known in the art. Suitable detection genes for the first and second plasmids of this aspect of the present invention include, for example those encoding visible markers, including, without limitation, Gus, and gfp, LacZ or luciferase. Any genes that provide a way to detect the integrated plasmid(s) in the organism's genome are suitable as a detection gene for the first plasmid and the second plasmid in this aspect of the present invention.

The presence of nucleic acids encoding a selectable marker and a detectable marker in a single plasmid combine the advantages of the individual gene-trap and enhancer-trap plasmids as described in above. Combining these two features into a single plasmid doubles the likelihood of identifying a disrupted gene, without increasing the number of transgenic organisms to be examined. An exemplary plasmid of this aspect of the present invention containing both an enhancer-trap and a gene-trap feature is shown in FIG. 6.

Thus, the first plasmid provided in this aspect of the present invention also contains all of the elements described above as "gene-trap" and "enhancer-trap" feature. This involves including one or more detection genes, with least one of the one or more detection genes is located inside the boundaries of the transposon recognition sequence, and is operably linked to a promoter element and a 3' terminator element. One such nucleic acid molecule is placed under the control of a minimal promoter in the plasmid that only expresses when inserted near a cis-acting enhancer in the host chromosome, creating an enhancer-trap. Transposition of the transposon recognition sequence to a site proximal to an enhancer region allows expression of the visible marker, thereby "tagging" the transposition site. A second nucleic acid encoding a detection marker is placed in the plasmid without a promoter, creating a gene-trap. Because the marker is dependent upon a promoter in the chromosome of the organism to direct its expression, its expression following transposition identifies the site of insertion as transcribed region or a promoter region of the chromosome.

The nucleic acid molecules included in either of the plasmids of this embodiment are also operably linked to one or more 5' promoter elements. The promoters of the first and second plasmids may be inducible (which is meant herein to include repressible promoters) or constitutive. When temporal control of gene expression is required, for example, to trigger a transposition event at a particular time or developmental stage of the organism, an inducible promoter is preferable. When an inducible promoter is used, the method of the present invention also includes a step of treating a transgenic organism with the corresponding inducing agent. Whenever possible, a germline specific promoter should be used. Exemplary promoters include, without limitation, the *Arabidopsis* anther specific promoter ("AP3"); the 35S CaMV gene promoter; the 1' and 2' promoters from a plasmid of *Agrobacterium* ("1'P" and "2'P"); the rice actin1 promoter ("Act1"), the maize ubiquitin gene promoter ("Ubi"); rice actin4 promoter ("A4P"); the zebrafish heat-shock-inducible promoter ("Hsp70") (Halloran et al., "Laser Induced Gene Expression in Specific Cells of Transgenic Zebrafish," *Develop.* 127:1953–1960 (2000), which is hereby incorporated by reference in its entirety), the cytomegalovirus gene promoter ("CMV"); the EF1a enhancer regulatory sequence promoter from *Xenopus* (Johnson et al., "pXex, a Vector for Efficient Expression of Cloned Sequences in *Xenopus* Embryos," *Gene* 147:223–226 (1994), which is hereby incorporated by reference in its entirety); SH3, the histone H3 promoter from salmon (Hanley et al., "Isolation and Functional Analysis of the Histone H3 Promoter from Atlantic Salmon (*Salmo salar* L.)," *Mol. Marine Biol. &Biotech.* 7:165–172 (1998), which is hereby incorporated by reference in its entirety); ARP, the acidic ribosomal phosphoprotein gene promoter (Ju et al., "Faithful Expression of GFP in Transgenic Zebrafish Embryos Under Control of Zebrafish Gene Promoters," *Develop. Genet.* 25:158–167 (1999), which is hereby incorporated by reference in its entirety); the Prm1 promoter (Fischer et al., "Regulated Transposition of a Fish Transposon in the Mouse Germ Line," *Proc. Natl. Acad. Sci. USA* 98: 6759–6764 (2001), which is hereby incorporated by reference in its entirety); the SV40 viral early promoter ("SV40") (see Fischer et al., "Regulated Transposition of a Fish Transposon in the Mouse Germ Line," *Proc. Natl. Acad. Sci. USA* 98: 6759–6764 (2001), which is hereby incorporated by reference in its entirety), and the phosphoglycerate kinase gene promoter ("PGK") (Luo et al., "Chromosomal Transposition of a Tc1/Mariner-Like Element in Mouse Embryonic Stem Cells," *Proc. Natl. Acad. Sci. USA* 95:10769–10773 (1998), which is hereby incorporated by reference in its entirety). Other useful promoters can also be used which are not named herein, but are known to those in the art.

Suitable 3' terminator elements for inclusion in the plasmid of the present invention are selected from among those that are capable of providing correct transcription termination and polyadenylation of mRNA for expression in the host organism or cell of choice, operably linked to the nucleic acid molecule of choice. Many 3' terminators are known. Examples suitable for use in this plasmid include, without limitation, those described above and those shown in Table 1, above, or Table 2, below.

In another aspect of this embodiment of the present invention, the first plasmid provided also contains a Cre-lox recombinase recognition sequence within the boundaries of the transposon-specific sequence molecule. lox is the 34 bp recognition sequence for the Cre recombinase gene (Ow, D. W., "Recombinase-Directed Chromosome Engineering in Plants," *Curr. Opin. Biotech.* 7:181–186 (1996), which is hereby incorporated by reference in its entirety). Cre is a 38 kDa recombinase protein from bacteriophage P1 which mediates site specific recombination between lox sites. A lox site consists of two inverted 13 bp repeats separated by an 8 bp asymmetric spacer region (for review see Sauer, B., Methods in Enzymology 225:890–900 (1993), which is hereby incorporated by reference in its entirety). The components of an exemplary lox-containing transformation plasmid of this aspect of the present invention is shown in FIG. 7. The plasmid of FIG. 7 is an enhancer-trap, gene-trap transformation plasmid composed of the same components as FIG. 6, with the addition of the lox site.

In the case where the integrated plasmid contains one lox site, as in FIG. 8, the introduction of a Cre-containing plasmid that also includes an intact copy of the gene Y results in the introduction of the intact gene Y into the transgenic organisms. This results in the replacement of the gene disrupted by transposition, thereby providing a "gain of function" phenotype. It is particularly useful for the nucleic acid encoding the Cre recombinase to be under the control of an inducible promotor. This is explained in greater detail in Example 16, below.

When there are two lox sites in the integrated plasmid (such as shown in FIGS. 9A–B), the activation of the Cre-recombinase catalyzes a reaction that results in excision of the DNA sequence located between the lox sites. FIG. 9A shows a segment of target DNA, flanked by two lox sequences. The Cre enzyme binds to each inverted repeat of each lox site, splicing the lox sites in half, releasing the intervening DNA, as a circular DNA, and then joins together the two halves of the lox sites. The excised target DNA is then degraded by cellular nucleases. In order to accomplish replacement, the two lox sites must be in direct orientation in the transformed organism, as shown in FIG. 9A. After the intervening DNA sequence is excised, it leaves one lox site in the genome of the organism. This transgenic organism becomes similar to that originally harboring a plasmid that includes only one lox site. Thus, this transgenic organism can be re-transformed with a plasmid that contains an intact copy of the disrupted gene Y for a gain-of-function test.

In one aspect of the present invention, the first plasmid also contains a nucleic acid sequence that is endogenous to the organism in which the library is being constructed for rapid analysis of copy number of the transgene. It is not required that the CN sequence be expressed, therefore it may be full-length or truncated, and does not require regulatory elements. It may be located in the insert either in side or outside of the transposon-recognition sequence.

This embodiment also relates to providing a second plasmid that includes a transposase gene, i.e., a nucleic acid molecule encoding a transposase enzyme and its flanking sequences ("TPase" or "TPase gene" herein) specific for the transposon recognition sequence integrated into the first plasmid. Examples of transposase genes suitable for this aspect of the present invention, without limitation, are shown in Table 2. This plasmid also contains one or more promoters and, optionally, additional enhancer elements, operably linked to the transposase gene. Exemplary promoters and enhancers include, without limitation, all those described herein or those known in the art. Promoters used in this plasmid may be constitutive or inducible. Inducible promoters are particularly useful for the second plasmid of this aspect of the present invention, as this allows temporal control of transposition within the transgenic organism following co-transformation with the first and second plasmids of this embodiment of the present invention. A suitable 3' terminator is also operably linked to the transposase gene.

The second plasmid of this aspect also has one or more selection marker genes, with each selection marker gene operably linked to a promoter element and a 3' regulatory element and where the first selection marker gene is different from the second selection marker gene. In this way, successful co-transformants harboring both the first and the second plasmid are readily identifiable as those organisms exhibiting the attributes conferred by the selection markers contained in both plasmids. As shown in Table 2, exemplary selection markers include, without limitation, Hpt, Bar, IAAH, Cah, Amp, Neo, and Puro.

In another aspect of the present invention, the second plasmid also contains a nucleic acid sequence that is endogenous to the organism in which the library is being constructed for rapid analysis of copy number of the transgene. It is not required that the CN sequence be expressed, therefore it may be full-length or truncated, and does not require regulatory elements.

In another aspect of the present invention, the second plasmid also contains a nucleic acid sequence encoding a tobacco matrix region ("TMAR"), which is inserted in the plasmid near the promoter element which is operably linked to the transposase gene of the plasmid.

In another aspect of the present invention, the second plasmid also contains a Cre recombinase gene, operably linked to a 5' promoter region and 3' regulatory element that are suitable for expression in the host of choice. The promoter may be a constitutive promoter, or an inducible promoter. When the promoter is inducible, the method of the this aspect of the present invention further involves treating the host cell containing the second plasmid with a suitable inducing agent at such time as induction of Cre gene expression is desirable.

The vector of choice, enzyme recognition clusters, promoters, transposon recognition sequence, selection cassettes, reporter cassettes, and appropriate 3' terminator(s) can be ligated together to produce the first and second plasmids of this aspect of the present invention using well known molecular cloning techniques as described in Sambrook et al., *Molecular Cloning: A Laboratory Manual*, Second Edition, Cold Spring Harbor Press, NY (1989), and Ausubel et al., *Current Protocols in Molecular Biology*, Wiley, Supplement 29 (1993), which are hereby incorporated by reference in their entirety.

Table 2, below, lists some of the essential components of plasmids that have been successfully used for transforming different living organisms. For simplicity of illustration, only four organisms are listed as examples. The same or similar components listed below can be used in many other organisms, and are suitable for the preparation of the plasmids of the present invention.

TABLE 2

Essential Components in Transposon Systems in Different Organisms

| Organism | Transposon System | Promoters from Gene | Selectable markers | Visible Marker | Method for Transformation[1] |
|---|---|---|---|---|---|
| *Arabidopsis thaliana* | Ac/Ds | AP3, 35S, 1' and 2' | Hpt, Bar, IAAH, Cah | Gus, GFP | *Agrobacterium* |
| *Oryza sativa* (rice) | Ac/Ds | Act1, Ubi, 35S, AP4, 1' and 2' | Hpt, Bar, IAAH, Cah | Gus, GFP | *Agrobacterium* |
| *Danio rerio* (zebrafish) | Tc1, Tc3 Mos1/peach | Hsp70, CMV, EF1a, SH3, ARP | Amp, Puro | LacZ, GFP | Microinjection of embryos |
| Mouse and Mouse cells | SB | Prim1, SV40, CMV, PGK | Neo, Puro | LacZ, GFP | Microinjection; Electrofusion |
| Human Cells | Tc1, SB | CMV, PGK | Neo | | Transfection |

[1] Retroviral vector-based infection and transfection of zebrafish embryos were not used because gene trap experiments cannot be done.

This method further involves co-transforming a plurality of organisms with the first and second plasmids described above, to produce a plurality of transformed organisms with the plasmids integrated at different locations within the genome of the organism. "Organism" as used herein is meant to include intact organisms as well as cells and cell lines, from sources including plants, invertebrates, and vertebrates. Transformation is carried out using methods appropriate for stable integration of the plasmids into the chromosome of the organism or cell of choice. For example, the *Agrobacterium*-based method for plants can be used as described in Sundaresan et al., "Patterns of Gene Action in Plant Development Revealed by Enhancer Trap and Gene Trap Transposable Elements," *Genes &Develop.* 9:1797–1810 (1995), and Shimamoto et al., "Trans-Activation and Stable Integration of the Maize Transposable Element Ds Cotransfected with the Ac Transposase Gene in Transgenic Rice Plants," *Mol. Gen. Genet.* 239: 354–360 (1993), which are hereby incorporated by reference in their entirety. Microinjection methods for zebrafish can be carried out as described in Raz et al, "Transposition of the Nematode *Caenorhabditis elegans* Tc1 or Tc3 Element in the Zebrafish *Danio rerio*," *Curr. Biol.* 8:82–88 (1998), and Fadool et al., "Transposition of the Mariner Element from *Drosophila Mauritania* in Zebrafish," *Proc. Natl. Acad. Sci. USA* 95:5182–5186 (1998), which are hereby incorporated by reference in their entirety. Microinjection for mouse and mouse cells can be carried out as described by Fischer et al., "Regulated Transposition of a Fish Transposon in the Mouse Germ Line," *Proc. Natl. Acad. Sci. USA* 98: 6759–6764 (2001), which is hereby incorporated by reference in its entirety) and for vertebrate cells, including human, transfection methods can be used as described in Schouten at al., "Transposon Tc1 of the Nematode *Caenorhabditis elegans* Jumps in Human Cells," *Nucleic Acids Research* 26:3013–3017 (1998), which is hereby incorporated by reference in its entirety. Microinjection aggregation of cells between transformed mouse embryonic stem cells and in mouse embryos can be carried out as described by Salminen et al., "Efficient Poly A Trap Approach Allows the Capture of Genes Specifically Active in Differentiated Embryonic Stem Cells and in Mouse Embryo," *Develop. Dynamics* 212:326–333 (1998), which is hereby incorporated by reference in its entirety. Other methods known in the art are also suitable. In one embodiment of the present invention, some of the members of the host of choice (e.g., plants or cells) can be transformed separately with the first plasmid, and some separately with the second plasmid to produce stable transformants.

Transformed plants are allowed to regenerate, and organisms or cells are cultured in suitable medium until stabilized. The copy number of the transgene in each transgenic cell, cell line, or T0 plant is determined using PCR with primers complementary to the nucleic acid sequence of the endogenous gene contained in each plasmid, or another sequence known to be present in each plasmid. Plants with only one copy of each transgene are chosen. The locations of the integrated plasmid in the transgenic plants are mapped in the chosen organisms, using TAIL-PCR as described in detail in Examples 1 and 9 below, and anchor transgenic plant lines with the integrated plasmid suitably spaced within the genome of the plants are identified.

In plants or other hosts in which co-transformation of the first and second plasmids provided in this aspect of the present invention was not used, the homozygous anchor transposon-specific recognition sequence transgenic plant lines are crossed with a plant having a nucleic acid molecule encoding a transposase ("TPase") to form progeny plants. Crossing activates transposition of a portion of the plasmid bounded by the 5' and 3' ends of the transposon-specific recognition sequence to form a plurality of progeny plants having different genes disrupted. In plants in which the "activator," i.e., TPase element, is under the control of an inducible promoter, induction is now carried out with an appropriate promoter-inducing agent to activate a transposition event within the transgenic host.

The transgenic organisms are subjected to a restriction enzyme digestion with the appropriate restriction enzymes to release a DNA fragment from each of the transgenic progeny plants, and the size of each of the released DNA fragments is measured by gel electrophoresis to determine transposition distances in each of the transgenic progeny plants. Progeny transgenic plants, or other host organisms, are selected with transposition distances which are different from the transposition distances of the other transgenic organisms by a distance of between 3 and 6 kilobases to prepare an indexed, non-redundant, saturation, gene-disruption library.

The present invention also relates to a transformation plasmid for constructing a gene-disruption library having an insert containing a transposon-specific recognition sequence with 5' and 3' ends which form the boundaries of the transposon-specific recognition sequence, and 2 clusters of restriction enzyme recognition sites. One cluster is located inside the boundaries of the transposon-specific recognition sequence and the second cluster is located outside the boundaries of the transposon-specific recognition sequence. The enzyme recognition sites in one cluster are identical to the enzyme recognition sites in the second cluster but the enzyme recognition sites in both clusters either do not exist or are rare in the organism which is to be transformed with the plasmid. This plasmid also includes one or more promoter elements operably linked to each gene in the plasmid, and one or more 3' terminator elements linked 3' to each gene in the plasmid. This plasmid also has one or more first selection marker genes, which is located inside the boundaries of the transposon-recognition sequence and which is operably linked to a promoter element and a 3' terminator element. The plasmid also contains one or more detection genes located inside the boundaries of the transposon-recognition sequence and which is operably linked to a promoter element and a 3' terminator element. In one aspect of the present invention, this plasmid also contains a nucleic acid sequence that is endogenous to the organism in which the library is being constructed for rapid analysis of copy number of the transgene. It is not required that the CN sequence be expressed, therefore it may be full-length or truncated, and does not require regulatory elements. It may be located in the insert either in side or outside of the transposon-recognition sequence. In another aspect of the present invention, the plasmid also contains a Cre-lox recombinase recognition sequence, located inside the boundaries of the transposon recognition sequence. FIG. 6 shows a generic version of such a gene-trap, enhancer-trap containing transformation plasmid. "V" is suitable a vector, and may include the left and right border sequence of *Agrobacterium*, in the case of a plant transformation plasmid, "CN" is a nucleic acid sequence endogenous to the plant added for rapid analysis of copy number of the transgene, SM1 and SM2 are selectable marker genes 1 and 2, 3' Ds and 5' Ds are recognition sequences of the mini maize Ac transposon, PM1, PM2, and PM3 are promoters, which may be constitutive or inducible, VM1 and VM2 are visible marker genes, E1 and E2 are rare restriction enzyme recognition sites, 3SA is splicing acceptor sequences, and I is an intron. Note that VM1 is under the control of a promoter, while VM2 is not, thereby creating the enhancer-trap and gene-trap features, respectively.

FIG. 10 shows an exemplary gene-trap, enhancer-trap, transformation plasmid designed specifically for transformation of *Arabidopsis*. Suitable vectors for construction of this plasmid of the present invention, enzyme recognition sites, 5' promoter elements, 3' terminator elements, selection markers and visible markers, as well as methods for construction of this plasmid are as described above.

Another aspect of the present invention relates to organisms, including plants, invertebrate cells, and vertebrate cells, including, but not limited to, human cells, transformed with the gene-trap, enhancer-trap transformation plasmid as described just above, and the progeny thereof which harbor the transgene of the transgenic parent(s).

Another aspect of the present invention is a method of constructing a non-redundant, indexed, saturation, gene-disruption activation-tagging library in an organism. This method involves providing a plasmid having a transposon-specific recognition sequence with 5' and 3' ends which form the boundaries of the transposon-specific recognition sequence, and 2 clusters of restriction enzyme recognition sites. One cluster is located inside the boundaries of the transposon-specific recognition sequence and the second cluster is located outside the boundaries of the transposon-specific recognition sequence. The enzyme recognition sites in one cluster are identical to the enzyme recognition sites in the second cluster but the enzyme recognition sites in both clusters either do not exist or are rare in the organism in which the library is being constructed. Also included in this plasmid is a transposase gene, which is located outside the boundaries of the transposon-specific recognition sequence and is operably linked to an inducible promoter and a 3' terminator element. The plasmid also contains one or more 5' promoter elements operably linked to each gene in the plasmid, and also has one or more 3' terminator elements operably linked to each gene in the plasmid. The plasmid also contains one or more enhancer elements which are located inside the boundaries of the transposon-recognition sequence and are located next to a promoter. Also included is a Cre recombinase gene which is outside the boundaries of the transposon-recognition sequence and which is operably linked to a promoter element and a 3' terminator element. In addition, the plasmid contains one or two Cre-lox recombinase recognition sequences, where at least one lox sequence is located inside the boundaries of the transposon recognition sequence. The plasmid also contains one or more selection marker genes, with at least one of the selection marker genes located in the plasmid inside the boundaries of the transposon-recognition sequence, and where each selection marker gene is operably linked to a promoter element and a 3' terminator element. This method also involves transforming a plurality of organisms with the plasmid to produce a plurality of transformed anchor organisms having the plasmid integrated at different sites within the transgenic organisms' genome, where the integration site of a plasmid due to transformation is defined as a plasmid's anchor location. A plurality of anchor transgenic organisms are selected, each having one copy of the plasmid integrated into the anchor transgenic organism's genome. The anchor location of each integrated plasmid in the plurality of transgenic organisms is mapped to identify anchor transgenic lines, where each identified anchor transgenic line harbors a plasmid within its genome at a location least 200–600 kilobases away from the location of a plasmid in other anchor transgenic lines. Expression of the transposase gene in the anchor transgenic organisms is induced, where inducing activates transposition of a portion of the plasmid bounded by the 5' and 3' ends of the transposon recognition sequence to form a plurality of transposants having different genes disrupted. The transposon-specific recognition sequence of the plasmid transposes from its anchor location to a different reintegration location in the anchor transgenic organism's genome, which defines a "transposition distance" between the anchor location and the reintegration location in a transposant's genome. Next, the transposition distances of transposed transposon-specific recognition sequences in a plurality of transposants in a given anchor line are determined. A plurality of transposants are selected, each having a transposition distance which is different from the transposition distance of the other transposants to prepare non-redundant, indexed, saturation, gene-disruption library.

This aspect of the present invention is shown in FIG. 12 in Steps A–J. Step A involves preparing the gene-disruption activation-tagging transformation plasmid of the present invention having a transposon-specific recognition sequence having 3' and 5' boundaries, one cluster of rare restriction endonuclease recognition sites inside the boundaries of the transposon element, and a second identical cluster of restriction endonuclease recognition sites in the plasmid outside the boundaries of the transposon-specific recognition sequence, a transposase gene under the control of inducible promoter, an endogenous nucleotide sequence for transgene copy number determination, at least one selection marker gene and at least one detection gene. Exemplary plasmids of this aspect of the present invention include, without limitation, those shown in FIGS. 11A–B.

As shown in Step B of FIG. 12, this aspect further involves transforming a plurality of cells or organisms with the gene-disruption transformation plasmid of the present invention to produce a plurality of transformed anchor cells or organisms with the transformation plasmid integrated at different locations within the genome of the transgenic organism. Transformation is carried out as described above or as described in Sambrook et al., Molecular Cloning: A Laboratory Manual, Second Edition, Cold Spring Harbor Press, NY (1989), which is hereby incorporated by reference in its entirety.

As shown in Step C of FIG. 12, identification of transgenic plants or cells is made based on the selection marker gene in the plasmid. For example, if the selection marker is the Hpt gene, (as in FIGS. 11A–B) the plants are grown in media containing hygromycin. Only those transformants that harbor the transformation plasmid having the Hpt gene will grow.

Next, those transformants selected are tested for transgene copy number, using PCR as described above with primers designed to hybridize to the endogenous nucleotide sequence, as well as the truncated sequence included in the transformation plasmid, represented by "CN" in FIGS. 11A–B. In Step E of FIG. 12, anchor organisms or cells are selected which preferably contain only one copy of the transgene. Next, as shown in Step F, the locations of the integrated plasmids in the transgenic organisms are mapped after determining the sequences flanking the boundaries of the transposon recognition sequence as described above, to identify the physical location of the transgene in the chromosome for each anchor transgenic cells or organisms. In Step G, anchors are chosen, each harboring one copy of the integrated plasmid evenly spaced within the genome of the cell or organism, with a distance of approximately 200–600 kilobases between adjacent anchor lines. Next, as shown in Step H, the inducible promoter of the transformation plasmid is activated by treatment with, or exposure to, a suitable inducing agent, thereby triggering transposition of the portion of the transformation plasmid bounded by the 5' and 3' ends of the transposon recognition sequence to form a plurality of transposants having different genes disrupted.

In Step I of FIG. 12, long PCR is employed to determine the transposition distance of the plasmid from its anchor site. Long PCR refers to a method that results in longer and more accurate DNA extension over standard PCR protocols by combining two thermostable polymerases: a non-proofreading polymerase as the main polymerase in the reaction, and a proofreading polymerase (3' to 5' exonuclease), which is present at a lower concentration (Barnes et al., "PCR Amplification of Up to 35-kb DNA with High Fidelity and High Yield from Lambda Bacteriophage Templates," *Proc. Natl. Acad. Sci. USA* 91:2216–2200 (1994), which is hereby incorporated by reference in its entirety). Routine amplification of genomic DNA targets from 10 kb to 40 kb in have been produced using this method (Cheng et al., "Effective Amplification of Long Targets from Cloned Inserts and Human Genomic DNA," *Proc. Natl. Acad. Sci. USA* 91:5695–5699 (1994), which is hereby incorporated by reference in its entirety). Thus, transposition distances up to 10 kb can be determined using long PCR, as described above, carried out on the genomic DNA of the transposants using one primer based on a known anchor flanking sequence and a second primer based on the sequence of the 3' boundary of the transposon-specific recognition element. For transposition distances beyond 10 kb from the anchor site, long PCR is carried out step-wise, moving along the chromosome in the direction corresponding to the direction the transposon has moved relative to its anchor site. This involves designing consecutive primers based on the sequence identified from the previous PCR product, beginning from 3' to the position of a previous transposant with a transposition of approximately 10 kb.

The principle of a rapid, PCR-based determination of transposition distance is further illustrated in FIG. 13. Starting from a specific anchor line, shown as Anchor A in FIG. 13, assume that 2,000 transposants are produced after transposition. Four of those transposants are shown here to illustrate the principle of the determination of the transposition distance relative to the Anchor A position, represented by the square in FIG. 13. The newly transposed site is represented by the triangle in FIG. 13.

If transposition in Transposant 1 of FIG. 13 occurred to the right of the anchor line, and the transposition distance is approximately 3 kb, that distance is simply measured by the size of the PCR product. For obtaining the PCR product, two primers are used. Primer 1 ("P1") sequence is derived from the right-hand side flanking genomic sequence of Anchor A before transposition. Primer 2 ("P2") sequence is derived from a portion of the 3' Ds sequence. After the PCR step, a 3-kb product is expected and the size can be determined accurately (±0.2 kb) after agarose gel electrophoresis simply by comparing with DNA size markers. Similarly, in Transposant 2, the PCR product is shown to be 10 kb (±0.5). It is assumed herein that long PCR can amplify a fragment of DNA up to 10 kb from the plant genome.

For a transposition distance between 10 and 20 kb from the anchor site, a similar procedure is used except that the sequence for primer 6 ("P6") is derived from the flanking sequence ("NS") of Transposant 2 of FIG. 13. By using primers P6 and P2, a 5-kb PCR product is expected from Transposant 3, and a 9-kb PCR product from Transposant 4 of FIG. 13 is generated.

By using the same strategy in cases in which transposition occurred to the right of the anchor position but with orientation inverted, primers P1 and P3 are used, as shown in FIG. 24B. In cases in which transposition occurred to the left of the anchor position, primers P4 and P5 are used, such as shown in FIG. 24D. In cases in which transposition occurred to the left, but with orientation inverted, primers P2 and P5 are used, as shown in FIG. 24E.

As discussed earlier, among all Ac/Ds based transposants, approximately 30% are expected to transpose within 300 kb from the anchor site (approximately 15% to the right and 15% to the left) based on literature reports in both *Arabidopsis* and rice. Therefore, out of 2,000 transposants, 300 are expected to transpose to the right of the anchor site within 300 kb, with an average distance of 1 kb between adjacent transposants. Following this reasoning, the probability of finding the PCR product to be approximately 3 kb from the anchor position is 1%. On the other hand, the probability of finding a PCR product to be 2, 3, or 4 kb in size (all three sizes are acceptable) is 3%. If these three transposants are all found, the transposant with a 3 kb PCR product is chosen to be a member of the insertion mutant library. However, those transposants that transposed within 1 to 2 kb from the chosen transposant are saved for future use because they may serve as allelic mutants and can help verify the relationship between a specific insertion mutant and an observed phenotype (or expressed gene as detected by the reporter gene present within the integrated plasmid).

The reason for generating 2,000 transposants from each anchor line is to provide a threefold safety factor in finding the transposants every 3 kb (±1 kb) to satisfy our need for producing an indexed insertion-mutant library.

Finally, as shown in Step J of FIG. 12, transposants of the third embodiment of the present invention are then selected which have transposition distances different from the transposition distances of the other transposants by between 3 and 6 kilobases.

Another aspect of the present invention relates to relates to an activation-tagging transformation plasmid for gene disruption in an organism having a transposon-specific recognition sequence having 5' and 3' ends which form boundaries of the transposon-specific recognition sequence and 2 clusters of restriction enzyme recognition sites. One cluster is located inside the boundaries of the transposon-specific recognition sequence and the second cluster is located outside the boundaries of the transposon-specific recognition sequence. The enzyme recognition sites in one cluster are identical to the enzyme recognition sites in the second cluster, but the enzyme recognition sites in both clusters either do not exist, or are rare, in the organism in which the library is being constructed. This plasmid of the present invention also includes a transposase gene, which is located outside the boundaries of the transposon-specific recognition sequence and is operably linked to a promoter element and a 3' terminator element. The plasmid also contains one or more 5' promoter elements operably linked to each gene in the plasmid, and one or more 3' terminator elements operably linked 3' to each gene in the plasmid. This plasmid also contains one or more selection marker genes located inside the boundaries of the transposon-recognition sequence and which is operably linked to a promoter element and a 3' terminator element. The plasmid also contains one or more detection genes located inside the boundaries of the transposon-recognition sequence, and where each detection gene is operably linked to a promoter element and a 3' terminator element. Also included in this plasmid are one or more enhancer elements located inside the boundaries of the transposon-recognition sequence next to a promoter. The plasmid also contains a nucleic acid encoding a Cre recombinase gene located outside the boundaries of the transposon-recognition sequence and which is operably linked to a promoter element and a 3' terminator element. There is also included in this plasmid one or two Cre-lox recombinase recognition sequences, with at least one lox sequence located inside the boundaries of the transposon-recognition sequence.

The gene-disruption transformation, activation-tagging plasmid of this aspect of the present invention is an improvement over the earlier plasmids described in the present invention. This plasmid include both elements of a two-component transposon system, in addition to an "activation tagging" feature. The presence of both elements of a two-component transposase system provides for a single transformation event, eliminating much time and effort. The term "activation tagging" refers to the possibility of activating endogenous genes by a component in the transformation plasmid. The "activation-tagging" feature is provided in the plasmid by inserting an enhancer, for example, the 35S enhancer from the CaMV 35 S promoter, into the portion of the plasmid bounded by the transposon-specific sequence. In FIGS. 11A–B, "35S Enh" designates four copies of the 35S enhancer element (350 bp per copy) from the CaMV 35S promoter, providing the activation tagging feature to both transformation plasmids. When transposition occurs and the portion of the Ds element bounded by the 3' and 5' ends relocates on the chromosome, the promoter of an endogenous gene that happens to be adjacent to the enhancer located within the transposed Ds border is activated and overexpressed. Overexpression of an endogenous gene is equivalent to "gain-of-function," which often leads to a change of the phenotype of the organism. In an anchor plant, the integrated activation plasmid can transpose to many locations in the chromosome and thus activate many genes to generate different members of the mutant library without the need to transform each gene individually for overexpression.

The plasmid may also include a nucleic acid sequence (CN) endogenous to the organism in which the library is being constructed for rapid determination of the copy number of the integrated plasmid in the transgenic cell line or organism. It is not required that the CN sequence be expressed, therefore it may be full-length or truncated, and does not require regulatory elements. It may be located in the insert either in side or outside of the transposon-recognition sequence. At least one lox sequence is included inside the boundaries of the transposon sequence. When a second lox site is included, it may be positioned anywhere in the plasmid outside of the portion bounded by the transposon recognition sequence. The location of the second lox provides for other manipulations of the transgenic organism making use of the Cre-lox system of DNA recombination, further described below. Choice of suitable components for the construction of the plasmid of this aspect of the present invention is guided by the choice of host organism in which the gene-disruption library is desired. Suitable vectors for construction of this plasmid of the present invention, restriction endonuclease recognition sites, 5' promoter elements, 3' terminator elements, selection markers, and visible markers, as well as methods for construction of this plasmid are as described above. Suitable transposon elements are those listed above, for example, those shown in Table 2, and are chosen based on the desired host organism. The vector of choice, enzyme recognition clusters, promoter elements, transposon recognition sequence, nucleic acid encoding a TPase, selection cassettes, reporter cassettes, and an appropriate 3' terminator can be ligated together to produce the plasmid of this aspect of the present invention using well known molecular cloning techniques as described in Sambrook et al., *Molecular Cloning: A Laboratory Manual*, Second Edition, Cold Spring Harbor Press, New York (1989), and Ausubel et al., *Current Protocols in Molecular Biology*, Wiley, Supplement 29 (1993), which are hereby incorporated by reference in their entirety.

FIGS. 11A–B show two examples of activation-tagging plasmids of the present invention which harbor both an Ac-transposase gene and a Ds element. These plasmids also include a self-activating, self-inactivating feature controlling the expression of TPase.

The self-activating, self-inactivating capacity of this plasmid of the present invention is provided by positioning an enhancer element immediately adjacent to a promoter. In the plasmids shown in FIGS. 11A–B, this feature is provided by the "35SP-35S Enh" cassette inside the border of the 3' Ds (i.e., the 3' border of the transposon recognition sequence). Because an enhancer is present, the 35SP can activate the TPase gene even when a segment of DNA (3' Ds) is between the gene and the enhancer-promoter complex, as shown in FIGS. 11A–B. The activation of the TPase triggers the transposition event, causing the relocation of the Ds element from its initial anchor site. "Self-inactivating" here means that after transposition, TPase is no longer adjacent to the "3' Ds-35SP-35S Enh" cassette. Thus, in both FIG. 11A–B, the TPase is inactivated by the occurrence of the transposition event. In FIG. 11A, where there is no other promoter provided for the TPase gene, transposition results in permanent inactivation of TPase in that plasmid. In FIG. 11B, however, the TPase has also been placed adjacent to another promoter, i.e., the glucocorticoid inducible promoter, GIP.

Thus, the TPase gene can again be re-activated, even following transposition, if desired, by treatment to induce GIP. The advantage of using a plasmid with an inducible promoter is that transposition of the resulting transgenic cells or plants can be initiated upon induction with a specific inducer (such as dexamethasone to induce GIP) for additional transposition after the initial transposition event. However, when the inducing agent is removed, the promoter is no longer active, and consequently, TPase is "self-inactivated," i.e., is no longer expressed. In both plasmids shown in FIGS. 11A–B, which have the self-inactivating features of the present invention, there is no need to carry out a genetic cross between an Ac- and a Ds-transformant, or a cell fusion between a TPase-containing cell and a transposon recognition sequence-containing cell. As a result, much time and effort is saved over other methods. Moreover, there is no need to remove the transposase gene by genetic segregation because without application of an appropriate inducing agent to the plants or cells, the TPase gene remains inactive, and transposition will not occur.

Another feature of this embodiment of the present invention is that after transposition the ActP promoter is adjacent to the Bar gene making the plant sensitive to the herbicide ammonium glufosinate, which makes it easy to detect transposants among many sublines in which no transposition occurred. All the components described herein as suitable for the construction of the other transformation plasmids of the present invention are also useful in constructing this self-activating, self-inactivating, activation-tagging plasmid of the present invention. Promoters, terminators, selection markers, and a suitable transposon system to be inserted in the activation-tagging plasmid are chosen based on the organism(s) to be transformed with the plasmid. Table 1 and Table 2 list exemplary components for this embodiment of the present invention for various host organisms, and others known in the art can also be used. Plasmid preparation and transformation methods as described above herein are also suitable for this single plasmid embodiment of the present invention.

Another aspect of the present invention relates to organisms, including plants, invertebrate cells, and vertebrate cells, including but not limited to, human cells, which are transformed with the activation-tagging plasmid of the present invention, and the progeny thereof which harbor the transgene of the transgenic parent(s).

EXAMPLES

Example 1

Preliminary Analysis of the Transgenic Plants

Figure 5:
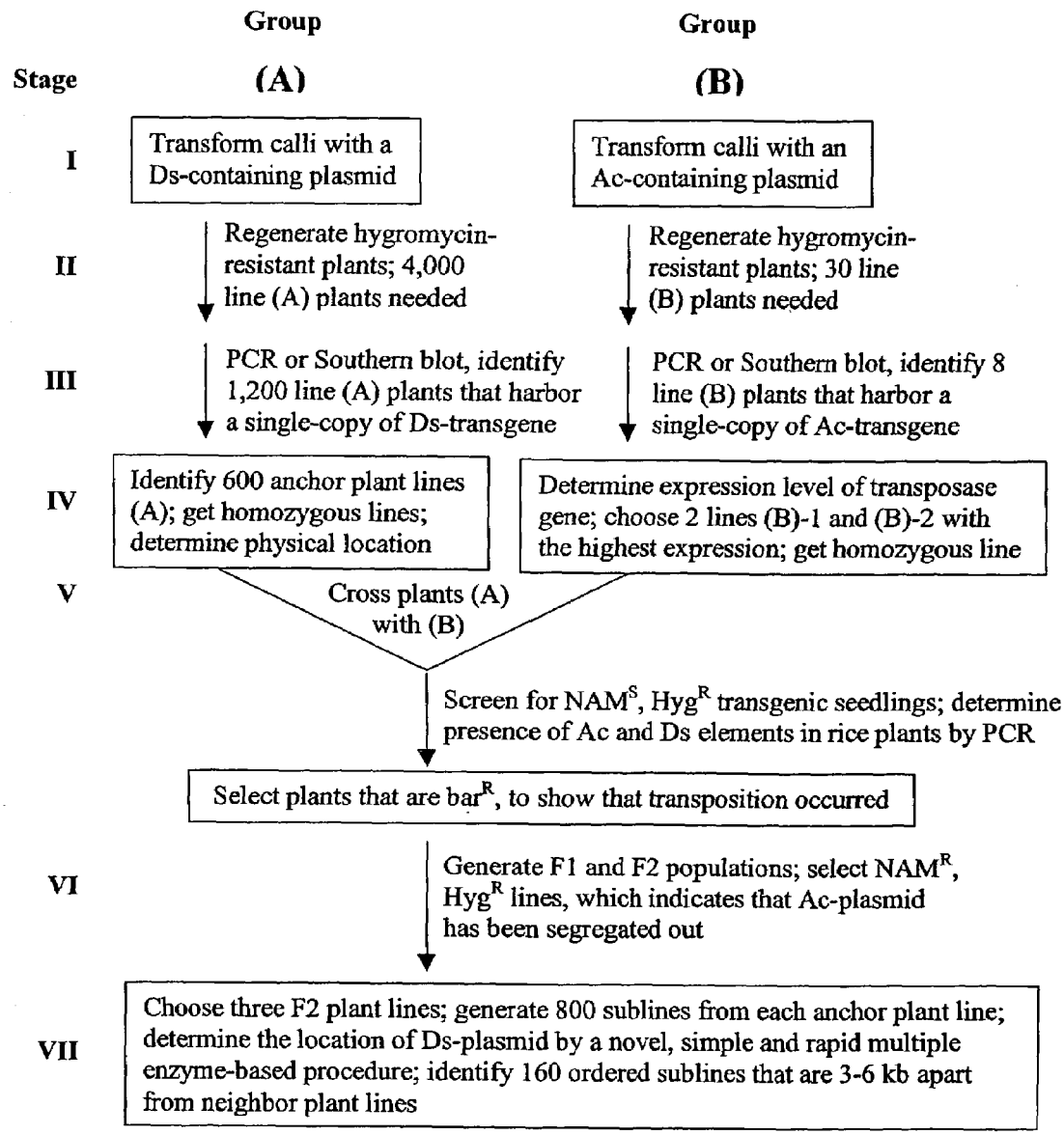
FIG. 5 is a schematic diagram of the main steps of the first embodiment of the present invention, detailed as Stages I–VII. The steps involving transformation of a Ds containing plasmid occur along the "A" line (left side of page, moving from top to bottom), and steps involving Ac-containing transformation occur along the "B" line (right side of page, moving from top to bottom).

Nipponbare rice variety is used as an example to illustrate the principle and different analytic steps of the enzyme-based procedure of the present invention. FIG. 5 diagrams the steps, or Stages, I through VII, of the method of the first embodiment of the present invention. These include simple procedures, which are much faster than the different published procedures, especially suitable for plant genome disruption. Stages I and II, shown in FIG. 5, and described below, are essentially the same as those reported by Sundaresan et al., "Patterns of Gene Action in Plant Development Revealed by Enhancer Trap and Gene Trap Transposable Elements," *Genes &Develop.* 9:1797–1810 (1995), which is hereby incorporated by reference in its entirety. Stage III incorporates the simple and more rapid method of the present invention.

In Stage I, calli are transformed either with a Ds-containing plasmid, the "A" line of FIG. 5, or with an Ac-containing plasmid, shown in FIG. 5 as the "B" line. Next, as shown in FIG. 5, Stage II, "A" or "B" plants are grown in a medium containing a selectable marker. The transformed plants are identified by growth in hygromycin, and the hygromycin resistant plants containing the Hyg gene are regenerated. Alternatively, haploid cells such as those derived from rice anther-culture are used for transformation with a plasmid such as the one shown in FIG. 8, which includes both an inducible promoter to drive the transposase gene and the Ds-containing component. The major advantage of using haploid cells is that the regenerated transgenic plants are also haploid and do not include a copy of the corresponding chromosome with copy of the plasmid used for insertion mutagenesis. Therefore, it is more likely to see the phenotype changes of the insertion-mutant plants.

In Stage III, transgenic plants are chosen that harbor only one copy of an unrearranged version of the plasmid as shown in FIGS. 1A, 2A, and 3A. These plants are chosen after either Southern blot analysis (Southern, E. M., "Detection of Specific Sequences Among DNA Fragments Separated by Gel Electrophoresis," *J. Mol. Biol.,* 98:503–17 (1975), which is hereby incorporated by reference in its entirety), or by a new application of the polymerase chain reaction (PCR) (Erlich et al., "Recent Advances in the Polymerase Chain Reaction," *Science* 252:1643–51 (1991), which is hereby incorporated by reference in its entirety). The application of a PCR method for copy number determination uses primers complementary to both the endogenous and the partially deleted single-copy endogenous gene segment that was included in the plasmid to detect the copy number of the deleted gene in comparison to the copy number of the normal gene in the allegedly transformed plant. An example of a suitable endogenous gene is a 132-bp segment of the rice cytochrome c gene, which was shortened to 107-bp from the middle of this segment. Homozygous R1 Ac-containing plants that harbor a single copy of the gene are used for further analysis.

At Stage 1V, FIG. 5, the homozygous R1 Ac-containing plants, line "B," are analyzed for the level of Ac expression. Since it is known that the Ac activity at different T-DNA insertion sites gives different levels of activity in *Arabidopsis* (Smith et al., "Characterization and Mapping of Ds-GUS-T-DNA Lines for Targeted Insertion," *Plant J.* 10: 721–732 (1996), which is hereby incorporated by reference in its entirety), this may also occur in other plants, and a simple test can determine the level of Ac expression, thereby optimizing the system. The level of the transposase mRNA can be determined by RNA blot or RT-PCR techniques. Two or three plants with the highest activity will be used to cross with Ds-containing plants.

Also in Stage IV, the approximate physical location of different anchor plant lines is determined for the Ds-containing transformants. Only those plant lines are chosen for further analysis that harbor a single copy of a Ds-containing plasmid suitably distributed on the plant genome (e.g., approximately 200 to 600 kb apart from neighboring plant lines). If 700 anchor plant lines are identified, for example, the average distance will actually be 600 kb apart for rice, because the rice genome is $4.3 \times 10^5$ kb. This is exemplary for the rice genome; for other plants the number of anchor lines needed will vary according to genome size.

The flanking sequence of each of the 5,000 plant lines, shown in Table 3, below, is determined, using the thermal asymmetric interlaced PCR ("TAIL-PCR") method (Liu et al., "Efficient Isolation and Mapping of *Arabidopsis thaliana* T-DNA Insert Junctions by Thermal Asymmetric Interlaced PCR," *Plant J.* 8:457–463 (1995), which is hereby incorporated by reference in its entirety). TAIL-PCR utilizes nested sequence-specific primers together with a shorter arbitrary degenerate primer to sequence the DNA adjacent to the known DNA segments of the transposon element, moving from the known sequence flanking of the transposon outward into the adjacent chromosomal sequence. The chromosomal sequences determined by TAIL-PCR are compared with the public databases for the genome of interest. It is estimated that approximately 70% of the sequences will match those in the databases whose chromosomal locations are also known. Out of the 1,200 to 1,600 plant lines that each harbor a single copy of the inserted plasmid, approximately 700 may be suitably spaced to become anchor plant lines. In this aspect of the present invention, "suitably spaced" means anchor lines occurring at approximately 600 kb apart along the genome of the transformed population.

Even though it is preferable to find between 600 and 700 well distributed anchor plant lines, 400 is sufficient. If the transported elements are relatively equally distributed in the rice genome, the average distance between anchor plant lines will be 1,080 kb. By adding more cycles of the chromosome-walking step of the present invention, it is readily feasible to walk 500 kb from either side of an anchor plant line to cover a 1,000-kb region. The plants identified as anchor plants are then used directly for Stage V, production of homozygous plant lines in R2.

In the second method, chromosomal DNA is isolated from the leaves of transformed plants, digested with I-PpoI enzyme, followed by pulse-field gel electrophoresis ("PFGE"), and the size of the released DNA fragment is determined by probing with a telomere sequence (Liu et al., "Protection of Megabase-Sized Chromosomal DNA from Breakage by DNase Activity in Plant Nuclei," *BioTechniques* 26: 258–26 (1999), which is hereby incorporated by reference). In this method, no flanking sequence needs to be determined. In principle, the physical location of the plasmid in anchor plant lines can be determined if the integrated copy of the I-PpoI-containing plasmid is within 10 mb from either end (telomeric region) of the chromosome. For example, in a 40-mb rice chromosome, in those plants in which the location of the integrated plasmid is within and up to 10 mb from each end, the location can be mapped by this method.

The error of this method for size determination is approximately ±8% of the distance between the inserted plasmid and one of the telomeres. For plant lines in which the physical location is within 3 mb from a telomere, the error is about ±0.2 mb with the current method, which is acceptable for the purpose of the present invention.

In order to fill major gaps, if they exist, a PCR-based approach, as shown in FIG. 14, is used that does not require the determination of the flanking sequence of each inserted plasmid in different plant lines. This is accomplished by using a variation of the method reviewed by Walbot, "Strategies For Mutagenesis and Gene Cloning Using Transposon Tagging and T-DNA Insertional Mutagenesis," *Annu. Rev. Plant Physiol. Plant Mol. Biol.* 43: 49–82 (1992), which is hereby incorporated by reference, and by Bensen et al., "Cloning and Characterization of the Maize An1 Gene," *Plant Cell* 7: 75–84 (1995), which is hereby incorporated by reference, which involves the use of a pair of PCR primers, one from the end of the Ds-containing plasmid (for primer 1 and/or primer 3), and one from a known rice sequence (for primer 2 and/or primer 4), as shown in FIG. 14. A useful rice sequence includes a known gene, a cDNA, an RFLP or a SSLP marker (Bell et al., "Assignment of 30 Microsatellite Loci to the Linkage Map of *Arabidopsis,*" *Genomics* 19:137–144 (1994); Li et al., "Assignment of 44 Ds Insertions to the Linkage Map of *Arabidopsis,*" *Plant Mol. Biol. Reporter* 17:109–122 (1999), which are hereby incorporated by reference), that is already mapped on the rice chromosome with an accuracy of approximately 1 cM (230 kb), or is located on a mapped BAC clone. Any one from among several thousand sequences whose location is known can be utilized as a primer. Using rice as an example, approximately 2,000 sequences are chosen that are evenly distributed in the rice chromosomes (e.g., one sequence for approximately 800 kb or so to cover the entire rice genome). Primer sites for PCR amplification at this step are shown in FIG. 14. PCR amplification (e.g., between primer 2 and primer 1, or between primer 3 and primer 4, shown in FIG. 14) can occur only if the distance between a pair of primers is below 8 kb. A fragment of up to 8 kb can be produced by using a long-range DNA polymerase for PCR (Barnes et al., "PCR Amplification of Up to 35-kb DNA with High Fidelity and High Yield from Lambda Bacteriophage Templates," *Proc. Natl. Acad. Sci. USA* 91:2216–2200 (1993), which is hereby incorporated by reference). Based on each of those sequences, primers 2 and 4 are synthesized and used for PCR. Any positive PCR result can be immediately used to define the physical location of the Ds-containing plasmid in an anchor plant line.

As soon as several anchor plant lines are located, homozygous plant lines can be obtained from among the R2 generation. At the same time, some of the R2 plants during flowering stage will be crossed with an Ac-containing plasmid, as shown in Stage V, FIG. 5. After that, many F2 and F3 seeds will be collected from each cross to proceed with the analysis of sublines after transposition events have occurred.

At this point, if there are gaps larger than 800 kb, it is possible that the gap regions may contain large stretches of repetitive sequences such as those around the centromere region. This can be checked with the DNA sequences in the public database. If this is the case, then this region will not need to be covered by subsequent steps.

The next step in this aspect of the method of the present invention involves obtaining homozygous anchor plant lines of second generation plants. This is shown as Stage V of FIG. 5. A homozygous Ac-plant is crossed with different homozygous Ds-plants, allowing transposition to occur, and many F1 generation plants are produced from 10 anchor plant lines. In some of these plants, transposition of the Ds element has occurred. Plants in which an inducible promoter is used are treated with the suitable inducing agent (e.g., dexamethasone for the glucocorticoid inducible promoter) at a time shortly before pollen mature or shortly after pollination. In this way, transposase is activated shortly after fertilization to allow germline transposition events to occur. Different F1 transgenic plants are allowed to self-pollinate and to produce many more F2 seeds. Among these plants, some seeds (approximately 25%) become homozygous by losing the Ac-containing plasmid (and the IAAH gene). Thus, the seedlings that germinate from these plant lines are NAM resistant (NAM$^R$), and the NAM$^R$, Hyg$^R$ transgenic rice seedlings are grown into plants. Next, a small amount of leaves from each plant is used to extract DNA to test, by PCR, whether transposition has occurred. PCR-positive plants can be confirmed by Southern blot hybridization. The plants that show transposition give additional hybridizing bands when the SDsG fragment is used as the probe. Those plants that show transposition are selected by analyzed further by the method of the present invention, as described below, following generation of F1 and F2 populations, selected for, as shown in Stage VI of FIG. 5, plants in which the Ac-plasmid has segregated out.

If the anchor plant lines do not span the entire genome of a plant, Stage V of FIG. 5 can be repeated, starting with specific plant lines after the first transposition event to allow additional anchor plant lines to be produced.

Example 2

Analysis of Plant Lines Containing Transposed Ds-Associated Sequences to Determine the Location of Different Transposants The principle of the method for determining the position after transposition and the distance of transposition from the anchor position is discussed first.

Using current published methods of analysis, the locations of the plasmid in the anchor position in a Ds plant, both before and after transposition, are determined by a genetic mapping method (Sundaresan et al., "Patterns of Gene Action in Plant Development Revealed by Enhancer Trap and Gene Trap Transposable Elements," *Genes &Develop.* 9:1797–1810 (1995); Bancroft et al., "Transposition Pattern of the Maize Element Ds in *Arabidopsis thaliana,*" *Genetics* 134:1211–1229 (1993), which are hereby incorporated by reference in their entirety). This genetic mapping method is very time-consuming, because it involves the restriction fragment length polymorphism ("RFLP") method and requires a large recombinant inbred (RI) population. An additional problem is that genetic mapping does not give the precise physical location of the plasmids in different plant lines before and after transposition. Although the simple sequence length polymorphism ("SSLP") method, which is much faster than the RFLP method, can also be used for mapping *Arabidopsis* (Bell et al., "Assignment of 30 Microsatellite Loci to the Linkage Map of *Arabidopsis,*" *Genomics* 19:137–144 (1994); Li et al., "Assignment of 44 Ds Insertions to the Linkage Map of *Arabidopsis,*" *Plant Mol. Biol. Reporter* 17:109–122 (1999), which are hereby incorporated by reference in their entirety), it also suffers from the same problem in not being able to give the precise physical location of the plasmids in different plant lines. The precision of either mapping method is likely to have an error of over 20 kb. Thus, investigators cannot choose those plant lines that have an integrated plasmid approximately 3–6 kb intervals throughout the genome.

For the purpose of illustration, and to demonstrate how the published genetic-based methods have been used, a 150-kb segment of a chromosome from the same anchor plant line A and 8 different F2 plant lines (sublines), instead of 160, are shown in positions 1 to 8 in FIG. 15B.

Example 3

Analysis of Transgenic Plants Using the Published Genetic-Based Method

FIGS. 15A–B show an analysis of transgenic plants for determining the location (distance) of transposition. The letter A in FIG. 15A represents the location of the integrated plasmid on a chromosome of anchor transgenic plant A. A-1, FIG. 15B, is the location of transposed and reintegrated Ds-containing portion of the integrated plasmid after transposition, and "A" indicates the empty site after transposition.

In this example, it is assumed that the exact distance of transposition is known, and the distance is written on top of each line in FIG. 15B. For example, in plant #1, location A1 may be approximately 50 kb away from location "A," etc. Thus, out of these 8 plant lines, since the locations of the newly transposed sequences in sublines #1, #2, and #3 are very close, so are sublines #4 and #5, they are redundant in tagging the same gene. Therefore, only two out of five lines are useful in tagging a gene of interest.

As can be seen from FIG. 15B, several large and small gaps exist in the 150-kb DNA fragment, because only 8 sublines are placed instead of 160 in this figure. The major difficulty is the genetic method cannot identify how many of these 8 sublines in FIG. 15B 160 sublines are actually generated) are redundant in tagging the same gene, thus most of the 160 sublines need to be analyzed by time-consuming procedures from this step on, including all the procedures in Step two of Phase III analysis. A comparison between the systematic approach of producing insertional-mutant rice libraries provided by the present invention and those already published is shown below in Table 3.

TABLE 3

Comparison of Five Methods to Construct a Saturation Gene-Disruption Rice Library for Functional Genomics[1]

| Method | Method of constructing an insertional-mutant library | Number of primary transformants needed[2] | Number of mutant plant lines need to be extensively analyzed[4] | Can one identify mutants with no phenotype? | Ease of obtaining revertants |
| --- | --- | --- | --- | --- | --- |
| A | T-DNA method[a] | 1,200,000 | 400,000 (400,000)[5] | No | Difficult |
| B | Tos17 system[b] | 12,000[3] | 400,000 (400,000)[5] | No | Difficult |
| C | Ac/Ds system[c] | 12,000 (3,600) | 400,000 (400,000)[5] | No | Easy |
| D | Ac/Ds system plus gene and enhancer traps[d] | 12,000 (3,600) | 400,000 (400,000)[5] | Yes | Easy |
| E | Method of the present invention (similar to D, but much improved) | 5,000 (1,600) | 96,000 (8,000) or less[6] | Yes | Easy |

[1]Note that all of the numbers in this table have been estimated, based on known facts and assumptions. The numbers may vary +30% without affecting the general principle of the present invention. To achieve a 99% probability that every rice gene (5 kb apart) has been tagged, the well-known formula is used: $P = 1 - (1 - f)^n$ or $n = \ln(1 - p)/\ln(1 - f)$ (see Krysan et al., "T-DNA As an Insertional Mutagen in *Arabidopsis*," Plant Cell 11: 2283–2290 (1999), which is hereby incorporated by reference in its entirety), for the source of formula and simple calculation), where P is the probability and f is the average distance (density) of genes in rice. n is the number of insertional mutants needed. For rice, $P = 1 - (1 - [5/430,000])^n$, and thus n = 400,000.
[2]According to the published results from the laboratory of Komari (Hiei et al., "Efficient Transformation of Rice (*Oryza sativa* L) Mediated by *Agrobacterium* and Sequence Analysis of the Boundaries of the T-DNA," Plant J. 6:271–282 (1994), which is hereby incorporated by reference in its entirety) using the *Agrobacterium*-mediated method for transformation, and our own data, approximately 30% of the transformants have a single copy of the transgene. Thus, to compensate for this observation, one needs to obtain 3 fold more initial transformants to work with only those plants that have a single copy of the transgene. Here 5,000 primary transformants will be produced, out of which approximately 1,600 are likely to harbor only one copy of the integrated plasmid in order to select 700 well-spaced anchor plant lines. Thus, numbers in parentheses are the expected number of rice plants with a single copy of the transgene.
[3]Assuming the tissue culture procedure to activate Tos17 transposon (Hirochika, H., "Retrotransposons of Rice as a Tool for Forward and Reverse Genetics," In Molecular Biology of Rice (Shimamoto, K., ed.), Springer, pp. 43–58 (1999), which is hereby incorporated by reference in its entirety, is equivalent to transformation of rice cells by the Ac/Ds system.
[4]Number of sublines of rice plants that need to be analyzed to achieve a 99% probability that every gene has been tagged.
[5]Numbers in parentheses indicate the number of flanking sequences that need to be determined. Assuming that only one (not both) flanking sequence for each insertional mutant line is sufficient. Many fewer flanking sequences need to be determined by the method of the present invention, because our pre-selected final sublines are linked to specific anchor plant lines. On the contrary, all other mutant libraries produce sublines that are not linked, and thus each one has to be analyzed separately.

TABLE 3-continued

Comparison of Five Methods to Construct a Saturation Gene-Disruption
Rice Library for Functional Genomics[1]

| Method | Method of constructing an insertional-mutant library | Number of primary transformants needed[2] | Number of mutant plant lines need to be extensively analyzed[4] | Can one identify mutants with no phenotype? | Ease of obtaining revertants |
|---|---|---|---|---|---|

[e]96,000 final, ordered plant lines resulted after the rapid pre-selection of approximately 400,000 random sublines. To determine the location of the 700 anchor plant lines, the flanking sequences do not need to be sequenced. To determined the location of all sublines, the maximum number of flanking sequences that need to be determined is estimated to be 3,000 at the most. However, if the flanking sequence of an anchor line and a long stretch of sequences on both sides is known and match those in the databank, a much smaller number of flanking sequences than 3,000 needs to be determined.
[a]Feldmann, K. A., "T-DNA Insertion Mutagenesis in *Arabidopsis*: Mutational Spectrum," Plant J. 1: 71–83 (1991), which is hereby incorporated by reference in its entirety.
[b]Hirochika, H., "Retrotransposons of Rice as a Tool for Forward and Reverse Genetics," In Molecular Biology of Rice (Shimamoto, K., ed.), Springer, pp. 43–58 (1999), which is hereby incorporated by reference in its entirety; assume that each plant has 5 copies of the endogenous Tos17 transposon.
[c]Shimamoto et al., "Trans-Activation and Stable Integration of the Maize Transposable Element Ds Cotransfected with the Ac Transposase Gene in Transgenic Rice Plants," Mol. Gen. Genet. 239: 354–360 (1993), which is hereby incorporated by reference in its entirety.
[d]Sundaresan et al. "Patterns of Gene Action in Plant Development Revealed by Enhancer Trap and Gene Trap Transposable Elements," Genes & Develop. 9:1797–1810 (1995), which is hereby incorporated by reference in its entirety.

In analyzing the insertional mutant plant lines in the field to look for altered phenotypes, assuming that 5 plants of each mutant line needs to be planted, using any of the shotgun method generated mutant plant lines, 2,000,000 plants need to be planted and examined for phenotype changes. In contrast, with systematically generated mutant plant lines of the present invention, only 480,000 plants need to be examined, which is only 24% the number needed for randomly generated plants. In conclusion, as can be seen from Table 3, the method of the present invention (E) is much superior than all the published approaches (A–D).

Example 4

Principal of Novel Biochemistry-Based Method

In contrast to the genetic-based method, the distance between plant lines or sublines can be can rapidly and accurately measured using the first, second, or third embodiments of the present invention, which provide three major advantages. First, only a small fraction of the time and labor is needed to analyze the same number of plant lines for their chromosomal location. Second, for each pre-selected anchor plant line, it is necessary only to sequence the flanking sequences of a small number of transposants by TAIL-PCR (Liu et al., "Thermal Asymmetric Interlaced PCR: Automatable Amplification and Sequencing of Insert and Fragments from P1 and YAC Clones for Chromosome Walking," *Genomics* 10: 674–681 (1995), which is hereby incorporated by reference in its entirety). Third, this method leaves practically no gaps in this 150-kb region or any other regions in the entire genome. In other words, all the genes can be systematically tagged.

For the construction of a saturation insertional-mutant rice library, only approximately 700 primary plant lines and 96,000 sublines need to be extensively analyzed. Moreover, the flanking sequences of less than 3,000 transposants need to be determined because the different plant lines generated from the same anchor plant line are "linked." This means that the approximate location of each subline is known relative to the location of the parent anchor line by the simple and rapid enzyme- and gel-based analysis of the present invention utilizing the two clusters of restriction enzyme recognition sites included in every plasmid of the present invention. If, after determining the flanking sequence of a given anchor plant line, and perhaps several of the sublines within the 700-kb region, the sequence of that region, or certain segments within this region, is already known, then the work can be simplified. Thus, the method of the present invention has a tremendous benefit over the published shotgun methods of constructing (Step one) and analyzing the insertional-mutant plant lines (Step two).

Figure 16:
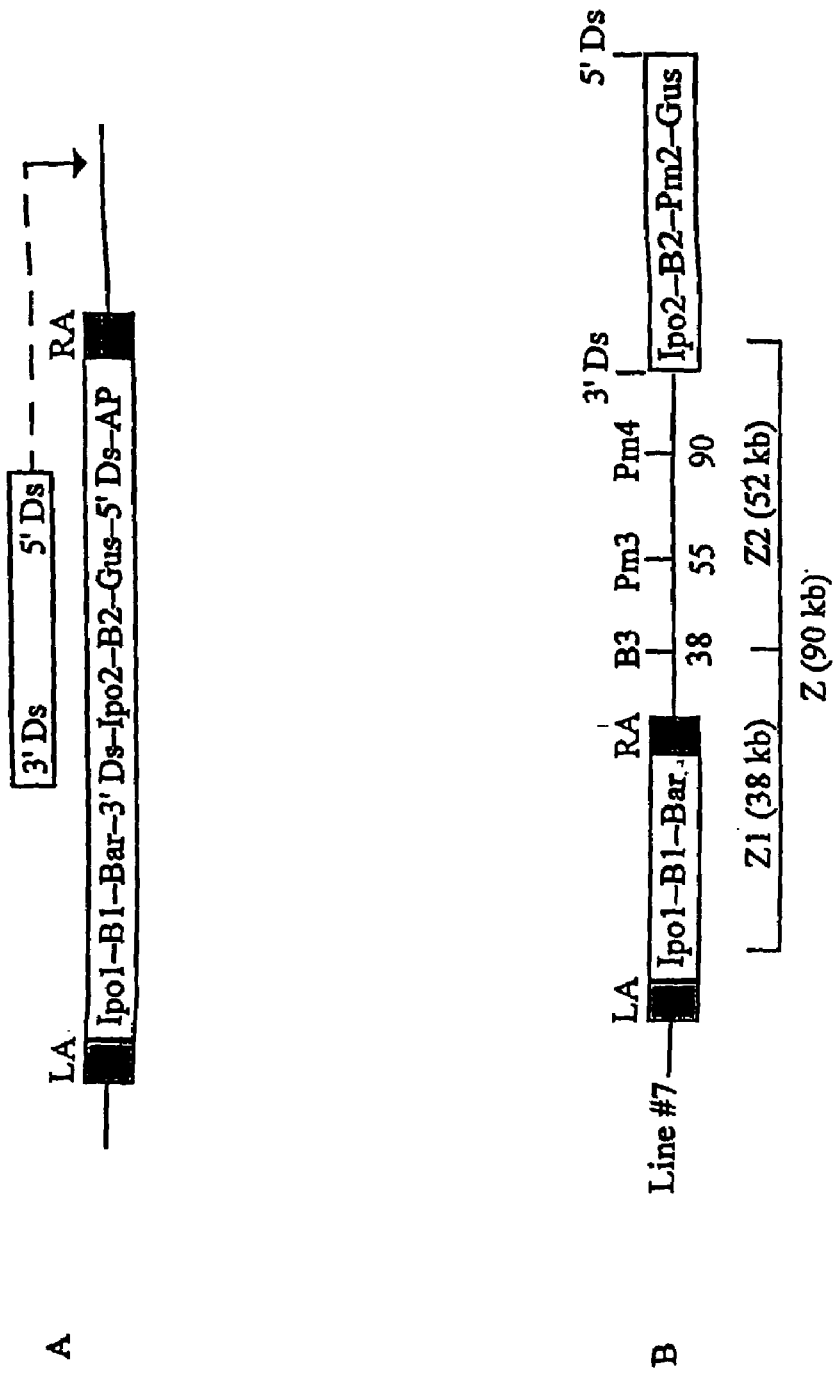

In the design of the super plasmids of the present invention, each Ds-containing plasmid contains two clusters of enzyme recognition sequences (including I-PpoI, I-CeuI, SfiI, NotI, PmeI, ApaI and SmaI). Digestion of total plant chromosomal DNA is carried out by incubation with one of the enzymes that cleaves the DNA at two informative locations on the plant chromosomal DNA. One location is within the Ds elements, and the other is outside the Ds elements. For simplicity of illustration, only the relevant sites in anchor line A and F2 line A-7 ("#7") are shown in FIG. 16. Note that in anchor line A, before transposition, the components are based on those shown in FIG. 3A, but further abbreviated by including only relevant components.

Example 5

Analysis of Transgenic Plants Resulting from a Single Anchor Plant Line, Using the Method of the Present Invention In Stage VI, shown in FIG. 5, F1 and F2 plant lines are chosen that have segregated out the Ac-containing plasmid, as indicated by the plant's resistance to NAM and Hyg. Next, in Stage VII, F2 plant lines are chosen for the next step in the analysis, which involves determining the location of the Ds-plasmid using the enzyme-based method of the present invention to determine the site of the plasmid insert before and after translocation occurs.

First, the restriction sites surrounding the plasmid insertion site in anchor plant lines need to be determined if such information is not in any available database. However, for rice and *Arabidopsis*, the information of a large percentage of the genome is already in the public database. Information about the nucleotide sequence of the restriction sites at the site of plasmid insertion (due to transposition) into the anchor plant lines is needed to more accurately determine the transposition distance of many transposants (secondary plant lines) that resulted after transposition. If the DNA sequence surrounding the anchor site is not known, it can be determined as follows. Selected restriction sites chosen from among those present in the two clusters of enzyme-recognition cutting sites in the plasmid are analyzed using anchor plant line "A" as an example, as shown in FIG. 17. FIG. 17 shows the restriction sites on the right-hand side of anchor line A, (shown in FIG. 15A) before transposition. SR1, SR2, SR3, etc. are the approximate locations of SmaI sites on the right-hand side of the integrated plasmid A (shown in the open box containing "A" in FIG. 17). "LA" represents the plant sequence immediately beyond the left border of the integrated plasmid, and "RA" represents the sequence beyond the right border of the plasmid. SR1 is the first SmaI site on the right side of "A". The steps for restriction site analysis are as follows.

Next, determine the flanking sequences on the left-side (LB) and right-side (RB) of plasmid insertion site in anchor plant "A" by using a traditional method, such as inverse PCR or TAIL-PCR (Liu et al., "Efficient Isolation and Mapping of *Arabidopsis thaliana* T-DNA Insert Junctions by Thermal Asymmetric Interlaced PCR," Plant J. 8:457–463 (1995), which is hereby incorporated by reference in its entirety).

Then use LB and RB sequences separately as probes to determine the position of different restriction sites on both sides of integrated plasmid A as follows. First, digest genomic DNA with I-PpoI and SmaI, followed by agarose gel electrophoresis and hybridization. By using either the LA or RA sequence as the probe, the approximate distances between SL1 and A, as well as SR1 and A can be determined (based on the size of the hybridizing band in comparison with the mobility of DNA size markers). Similarly, digestion of genomic DNA with I-PpoI and PmeI shows the distance between Pme R1 and the I-PpoI site (Ipo) in A. Finally, partial digestion with SmaI enzyme, and probing with RA, gives the approximate distances of SR2, SR3, etc., from Ipo site in integrated plasmid A.

Note that a partially digested plant DNA sample can be used also for many other probes, such as "RB" (right-hand flanking sequence of an anchor plant B), to determine the restriction sites flanking other anchor plant lines (such as anchor plant B), and so on.

Using the same principle and other restriction enzymes, such as SfiI, NotI, etc., together with I-PpoI, to digest genomic DNA in anchor plant line A, at least 400 kb on the left-side and the right-side can be reached, spanning a region of approximately 800 kb.

Next, the plasmid transposition distances are determined. FIGS. 16A–B illustrate the analysis of an F2 plant line in which the Ds-containing segment from pSDsG is assumed to be transposed to a location approximately 90 kb away from the anchor position. Note in FIG. 16B that after transposition the Bar gene selectable marker is now adjacent to the AP promoter, and, thus, the plants become resistant to the herbicide phosphinothricin. By using phosphinothricin for selection, those plant lines where transposition has occurred can be easily identified.

FIG. 16A shows Anchor line A before transposition (an abbreviated version of the plasmid is shown in FIG. 2). Abbreviations are the same as described above, except that LA represents the plant sequence immediately beyond the left border of the plasmid, and RA represents the plant sequence beyond the right border. Ipo1 and Ipo2 are the two Ipo restriction enzyme recognition sites; B1 and B2 are the two BglI recognition sites. Open box(es) represent portions of the plasmid used for transformation; thin horizontal lines represent genomic DNA. After transposition, the DNA sequence within the borders of 3' Ds and 5' Ds is transposed to a different location on the plant genome, as shown in FIG. 16B.

If the distance of transposition in different plant sublines is between 1 kb up to 50 kb, the transposition distance can be accurately determined as follows. The chromosomal DNA is digested with Ipo1, followed by agarose gel electrophoresis and probing with a nucleic acid probe designed to hybridize the DNA sequence of the Bar marker. The size of the hybridizing band gives the distance of transposition. By this simple and rapid procedure, 1,000 plants can be analyzed within a few weeks. Out of these, it can be expected that a number of well-spaced sublines with transposition distances of approximately 5, 10, 15, 20, 25, 30, 35, 40, 45, and 50 kb from the anchor position can found. It is also expected a number of plants can be found in which the transposition distance is between 50 and 100 kb. For example, it may not be possible to clearly distinguish the transposition distance of 80 kb from 85 kb. However, a more accurate determination of the distance can be made as follows.

As shown in FIG. 16B, if it is assumed the transposition distance is 90 kb, this distance can be measured more accurately by cleaving it into two smaller fragments and measuring the size of each. To achieve this goal, genomic DNA from plant line #7 (shown in FIG. 15B) is digested with I-PpoI enzyme to release a fragment Z. Following agarose gel electrophoresis (0.45% gel) and hybridization with 3'Ds DNA sequence as the probe, the approximate size of fragment Z can be measured by comparison with several DNA size markers used during electrophoresis (the accuracy is approximately 90 kb±5 kb). The size of fragment Z is determined more accurately by digesting the genomic DNA with I-PpoI enzyme, plus another restriction enzyme such as BglI ("B"). On average, the recognition sequence of BglI (B) is found every 20 kb in the plant genome (see Table 4, below), thus, it is likely that fragment Z contains one or two BglI sites. If there is one BglI site such as B3 in fragment Z as in FIG. 16B, after digestion with BglI, the size of Z1 and Z2 can be determined accurately by using two different probes: one with the Bar sequence to detect fragment Z1, and the other with 3'Ds to detect fragment Z2. Since Z1 and Z2 are shorter than Z, the size of each fragment can be measured more accurately because electrophoretic mobility is a log function of molecular weight. In this example, Z1=38 kb, Z2=52 kb, and accuracy of measurement is +2 kb. Similarly, the distance between Ipo1 and Pm3 can be determined (it is 55 kb in this example) after probing with Bar.

TABLE 4

Average Fragment Size of Restriction Enzyme-Digested Plant DNA*

| Enzyme | SfiI | AscI | NotI | PmeI | ApaI | BglI | SmaI | SalI | XhoI | EcoRI |
|---|---|---|---|---|---|---|---|---|---|---|
| Fragment Size (kb) | 400 | 400 | 200 | 60 | 25 | 20 | 10 | 6 | 4 | 4 |

*(New England BioLabs Catalog 1998–99, p. 277)

If the approximate distance of transposition in a particular subline is already determined, as just described, the distance of another transposant that transposed farther along the genome (in the same direction away from the anchor line) can be determine. This principle is illustrated by using the specific example shown in FIG. 18.

Relative to the original anchor position in plant A, assume that the approximate location of B3, Pm3, Pm4 has already been determined as shown in FIGS. 16A–B. First, the genomic DNA from subline #7 is digested with I-PpoI enzyme, followed by agarose gel electrophoresis and probing with Bar. In this example, it is assumed that the distance is approximately 130 kb±10 kb. The measurement can be made more precisely by digesting the genomic DNA with Pme1, followed by gel electrophoresis and probing with 3' Ds. In this example, the fragment size between Pm4 and Ipo2 is 40 kb±0.2 kb. Because the distance between Ipo1 and Pm4 is already known to be 90 kb, then the distance of transposition in this subline #7 is 130 kb.

By repeating this process of specialized chromosome-walking, step-by-step, the transposition distance of many other transposants (sublines) can be determined relatively accurately, because only ordinary agarose gel electrophoresis is needed. It is expected that this procedure can reach at least 400 kb to the right, and 400 kb to the left, from the original location of the Ds-containing plasmid in this anchor line "A". Thus, a total distance of approximately 800 kb surrounding this or any other anchor line can be fully covered.

Analysis of many more F2 plant lines in which the Ds-containing segment from pSDsG is assumed to be transposed to many different locations, in different plant lines, all starting from a single anchor position, can be made in the same manner by applying the method of the present invention.

Each anchor plant line (such as anchor line A) can be used to produce several thousands of F2 (or F3) sublines after transposition in order to span approximately 800 kb. Recall that the final aim of the present invention is to construct a saturation, insertional mutant library with an insertion in each 3–6 kb of the host genome. Thus, approximately 160 F2 plant lines are needed to span the 800 kb adjacent to anchor line A. In order to obtain 160 suitably spaced F2 plant lines, between 800 and 1,200 F2 plant lines may need to be analyzed by agarose gel-based analysis.

The determination of the transposition distance in different plant lines starting from anchor line A of FIG. 15A–B, using the method of the present invention for analysis, is demonstrated by FIG. 19. In this example, transposition distance is 50 kb. Estimation of the distance of transposition in each plant line, such as plant lines #1 to #8 in FIG. 15B, can be accurately determined as follows.

FIG. 19 shows an expanded map of the right-hand side of anchor line A before transposition, where ER1, ER2, ER3, etc., are the approximate location of the recognition site of a rare restriction enzyme on the right-hand side of A. This information is useful, because it drives the decision of which transgenic lines to analyze further by determining their flanking sequences. The flanking sequences of the inserted Ds-containing plasmid can be easily determined, using PCR methodology with primer design based on the known sequences at that location and compared to those in the GenBank. If the sequence of this region of the genome is already known, then the location of ER1 to ER6 and SmaR1 and SmaR2 would also be known.

Another use of the plasmid of the present invention to determine sequences after transposition is shown in FIG. 20. FIG. 20 shows transformed plant A-2, where position of the reinserted Ds-containing part of the plasmid is shown as in the center of this figure, represented by box "A2", which includes the Gus marker, and where 2L and 2R represent the left- and right-side flanking sequences in plant A-2. After digesting the genomic DNA in plant A-2 with I-PpoI enzyme, followed by gel electrophoresis, the distance between the two Ipo sites can be determined accurately (in this example, 18 kb) by comparison with the mobility of DNA markers.

After discovering the approximate position of A2 in plant A-2, the flanking sequence on the right-hand side (2R) is determined by simple PCR as follows. If the sequence in this region is known by comparison with those in the GenBank, then by using primer 8 (P8, whose sequence is known) and primer 7 (P7, whose sequence is complementary to a portion of A2), the sequence between them can be amplified and determined. If the nucleotide sequence in this region, between ER3 site and Ipo1 site, is not known, then one can use the commonly adopted methods of inverse PCR or TAIL-PCR to determine the sequence (Liu et al., "Efficient Isolation and Mapping of *Arabidopsis thaliana* T-DNA Insert Junctions by Thermal Asymmetric Interlaced PCR," *Plant J.* 8:457–463 (1995), which is hereby incorporated by reference in its entirety). The sequence of 2R is then used as a probe to determine more exactly the distance of other plant lines such as plant A-4 as shown in FIG. 21 and described above.

In plant A-4, the distance of transposition is approximately 37 kb from Ipo2 site in A (the distance may be 37 kb±3 kb), and it is known that there is an SR2 site approximately 33 kb from the Ipo2 site, as seen in FIG. 21. In order to determine the distance between the Ipo2 and Ipo1 sites more accurately in plant A-4, the 2R probe in plant A-2 is used for hybridization (note that the position of 2R, which is the flanking sequence in the genome, is approximately 18 kb from Ipo2, but the DNA sequence between two Ds elements is not present next to 2R in plant A-4). The strategy is to measure the distance between the Ipo1 site and 2R, instead of between the Ipo1 and Ipo2 sites. In this example, genomic DNA in plant A-4 is digested with I-PpoI and SmaI enzyme (which cuts at SR1 and SR2), followed by gel electrophoresis. Then, by hybridizing with 2R as the probe, the hybridizing fragment size is determined to be 17 kb. Next, by using Gus as the probe, a fragment of 4 kb is found, which represents the distance between Hyg in A4 and the SR2 site. Since the distance between SR1 and Ipo2 is known to be 16 kb, then the distance between Ipo1 and Ipo2 is 16+17+4=37 kb. Here, the error of size estimation is reduced to approximately ±1 kb.

For determination of transposition distances of up to 400 kb, the type of analysis described with reference to FIG. 21 is repeated, resulting in accurate transposition distances in other transgenic lines. In the case of plant line A-4 shown in FIG. 21, the 4R flanking sequence of A-4 plant is determined and, then, 4R is used as the probe for the next set of plants. In principle, this type of selective chromosome walking can allow the accurate determination of the location of the transposed segment in many transgenic plant lines, up to at least 600 kb away from the anchor plasmid position. Similar analysis can be done using LB probe and place many plant lines in the left-hand side of the anchor plasmid in plant A.

The final result of the above analysis is that the accurate distance of transposition of many plant lines that are derived from the same anchor plant line A can be determined. By analyzing 600–800 plant lines, those plant lines can be chosen that have transposition distances, for example, approximately 3–6 kb between any adjacent plant lines. For example, it can expected that approximately 80 sublines (secondary plant lines) can be identified with transposition/reinsertion sites of approximately 5, 10, 15, and 20 kb, etc., up to 400 kb on the left-hand side, and 80 plant lines on the right-hand side of the integrated plasmid position in anchor plant A. In this method of analysis, it is not necessary to determine the flanking sequences of each of these 160 sublines, which span 800 kb of DNA. At the most, the determination of the flanking sequence of one plant line out of 10 plant lines is adequate. Thus, a large amount of time is saved by eliminating the need to carry out inverse PCR analysis on all 800 plant lines, which is required when the published shotgun procedures from other laboratories are utilized.

Because the approach of the present invention is a systematic approach, it can be assumed that approximately 800 of the sublines are within a 800 kb region centered around an anchor line A, and that all these sublines are linked to the anchor line A, with approximate distance known after an enzyme-based analysis. Approximately 160 sublines can be selected out of this 800 kb region. The remaining 640 sublines are not useless, because they represent sublines that have insertions in this region with an average distance of 1 to 3 kb apart. Some of them may be useful in regions where the gene size is 2 or 3 kb instead of 3–6 kb. Thus, these sublines can be saved.

In order to demonstrate the validity of the principle of this invention, a simpler plasmid, pEDI, was first constructed. This plasmid, shown in FIG. 22 in an abbreviated form, includes two I-PpoI sites, for transformation of *Arabidopsis*. Plasmid pEND4K (Klee et al., "Vectors For Transformation of Higher Plants," *Bio/Technology* 3: 637–642 (1985), which is hereby incorporated by reference in its entirety), is used as the vector. LB and RB are the left and right borders of the T-DNA, respectively. The 5' Ds and 3' DS sequence are from Hehl (Hehl et al., "Induced Transposition of Ds By a Stable Ac in Crosses of Transgenic Tobacco Plants," *Mol. Gen. Genet.* 217: 53–59 (1989), which is hereby incorporated by reference in its entirety). All other components of this plasmid are from commonly available sources. Methods for the construction of the pEDI used the common procedures as described in Ausubel et al., *Current Protocols in Molecular Biology*, Wiley, Supplement 29 (1993), which is hereby incorporated by reference in its entirety. The plasmid was first tested by digestion with I-PpoI enzyme, and a 400-bp DNA fragment was released as expected.

Plasmid pEDI was transformed into *Arabidopsis thaliana* C24 by an *Agrobacterium*-mediated method. First-generation plants were screened by germinating plants on agar plates that contain 30 mg/L of kanamycin. Kanamycin-resistant plants were obtained.

For illustration, *Arabidopsis* is used to show the principle of the design and the method of the analysis of transgenic gene-disrupted plants in accordance with the present invention. The same principle can be used for any monocot or dicot, including the production of gene-disrupted mutants in trees. In principle, this invention can be applied to any plant species, as long as transformation and regeneration systems are available, and the Ac/Ds system can operate in that species (for a review, see Federoff, "Maize Transposable Elements," In: *Mobile DNA* (Berg, D. D. and Howe, M. M., eds.), pp. 375–411 (1989); Martienssen, "Functional Genomics: Probing Plant Gene Function and Expression with Transposons," *Proc. Natl. Acad. Sci. USA* 95:2021–2026 (1998); Enoki et al., "Ac as a Tool for the Functional Genomics of Rice," *The Plant J.* 19:605–613 (1999); Wu, "Report of the Committee on Genetic Engineering: Functional Genomics of Plants," *Rice Genetics Newsletter* 16:10–14 (1999), which are hereby incorporated by reference in their entirety.)

Example 6

Preliminary Analysis of Transgenic *Arabidopsis* Plants

Following transformation with pEDI as described above, over 700 first-generation plants were screened by germinating the seeds in the presence of kanamycin. Most plants were resistant to kanamycin, indicating that they harbored the pEDI plasmid. Second- and third-generation plants (R2 and R3) were screened again with kanamycin and the segregation pattern scored. Over 300 plants, which were shown to harbor a single copy of the pEDI plasmid, have become homozygous. R3 plants were further analyzed using molecular biology techniques.

Example 7

Analysis of Transgenic *Arabidopsis* Plants Using Molecular Biology Techniques

Out of 300 plant lines analyzed, over 50 were randomly selected for DNA blot hybridization (Southern blot) analysis. Each was shown to contain an integrated copy of the pEDI plasmid. Additional analysis was carried out on 39 transgenic plant lines by isolating the chromosomal DNA using the agarose embedding technique (Liu et al., "Thermal Asymmetric Interlaced PCR: Automatable Amplification and Sequencing of Insert and Fragments from P1 and YAC Clones for Chromosome Walking," *Genomics* 10: 674–681 (1995), which is hereby incorporated by reference in its entirety). After preliminary pulsed-field gel electrophoresis (PFGE) for 8–12 hours to remove broken DNA, the DNA in the gel plug was removed and digested with I-PpoI enzymes. After longer PFGE (24–36 hours), the DNA in the gel was blotted onto nylon filters. DNA blot hybridization was carried out using the *Arabidopsis* telomere sequence as the probe. Hybridizing bands within the size range of 0.1 to 5 Mb were found in different samples, indicating that the fragments include a chromosomal end. Without further mapping the exact location of these plants, each plant (about 10) was used in the next step by crossing with Ac-containing plants.

Example 8

Crossing Ds Containing Plants with Ac Containing Plants

Each Ds-containing plant (that showed hybridizing bands after digesting the DNA with I-PpoI enzymes, followed by PFGE) was crossed with two different Ac-containing plants (lines Ac2 and Ac5), obtained from Sundaresan et al., "Patterns of Gene Action in Plant Development Revealed by Enhancer Trap and Gene Trap Transposable Elements," *Genes &Develop.* 9:1797–1810 (1995), which is hereby incorporated by reference in its entirety. Seeds from each cross were collected and germinated. A portion of each three-week-old F1 plantlet was used for PCR analysis to identify those plants in which transposition has occurred. Later on, PCR analyses were carried out with F2 plants. Those plants in which transposition has occurred give different patterns of PCR-produced DNA bands.

In the next step, DNA from the plants that showed transposition were used for further analysis by digestion with the I-PpoI enzymes. Then, electrophoresis was carried out to look for the appearance of a new DNA band. Regular agarose gel electrophoresis was used first which can detect the appearance of new DNA bands with the size range of 2 kb to 50 kb. Those samples that gave new DNA bands larger than 50 kb were further analyzed by PFGE. In both cases, the approximate size of the new DNA band gave the distance of transposition.

Example 9

Plants Co-Transformed with Separate Plasmids Containing Transposon System Elements Again, *Arabidopsis* is used to illustrate the principle of the present invention. The goal is to achieve a 99% probability that every gene has been tagged by producing an indexed, insertion-mutant cell or plant lines in which every mutant line is approximately 3–6 kb apart from neighboring lines. By using the specially-designed plasmids of the present invention, one needs to generate only about 50,000 ordered, indexed, insertion mutation lines, which can be readily derived from a suitable number of anchor lines (such as 700, spaced approximately 200 kb (but up to as much as 600 kb) apart throughout the genome. This is especially advantageous over published methods in which 230,000 randomly generated insertion-mutant plant lines need to be produced and analyzed. Thus, the systematically produced indexed library taught herein needs to be only 22% as large as any randomly produced library.

In order to carry this aspect of the present invention, different transposon-specific recognition sequence-containing and transposase-containing plasmids were constructed in accord with the method of the present invention for use with *Arabidopsis*. FIGS. 6, 7, and 10 show exemplary plasmids containing a transposon-specific recognition sequence from maize, the Ds element.

*Arabidopsis* plants were transformed or co-transformed with Ds- and/or Ac-containing plasmids, using the *Agrobacterium*-mediated transformation procedure (Sundaresan et al., "Patterns of Gene Action in Plant Development Revealed by Enhancer Trap and Gene Trap Transposable Elements," *Genes &Develop.* 9:1797–1810 (1995), which is hereby incorporated by reference in its entirety). Since different selectable markers were used in each of the plasmids used for co-transformation, hygromycin in the Ds plasmid, as in the plasmid shown in FIG. 1, and the NPT II gene for kanamycin resistance in the Ac plasmid, shown in FIG. 4C, plantlets that were resistant to both hygromycin and kanamycin indicate the presence of both the Ac and Ds plasmids. *Arabidopsis* plants were also transformed separately with a Ds-containing plasmid and an Ac-containing plasmid. The goal is to produce at least 3,000 transformants, each including one copy of the Ds-containing T-DNA, and 20 plants that harbor only one copy of the Ac-containing plasmid.

Next, the copy number of the transgenes were determined. When the T1 plants grown in soil were one month old, PCR was carried out to determine the copy number of the transgene in each plant by using a PCR-based method. The principle of this method is as follows.

In the Ds plasmid, shown in FIG. 10, is included a partially deleted *Arabidopsis* GPA-1 gene (GP-del), abbreviated as CN, which was derived from a portion of the *Arabidopsis* GPA-1 gene (Ma et al., "Molecular Cloning and Characterization of GPA1, a G Protein α-Subunit Gene from *Arabidopsis thaliana*," *Proc Natl Acad Sci USA* 87(10): 3821–25 (1990), which is hereby incorporated by reference in its entirety) by deleting 409 bp from the center part to produce GP-com. After PCR analysis using T0 generation *Arabidopsis* genome DNA, compare the band density of GP-del from the transgene with the endogenous GP-com. Because the transgene in T0 plants is hemizygous, and the endogenous GP-com is homozygous, for plants with a single copy of the transgene, GP-del/GP-com=0.5, and those with a ratio of one means there are two copies of the transgene. In addition, the zygosity of T1 plants can be determined by the same PCR method. In homozygous T1 plants that contain a single copy of the transgene, GP-del/GP-com=1; in heterozygous plants, GP-del/GP-com=0.5.

Only those T1 plants that harbor one copy of the Ds-transgene and one copy of the Ac-transgene were used for ease of subsequent biochemical and genetic analyses. This minimizes the probability of transgene silencing that is often related to multi-transgene events (Holmes-Davis et al., "Nuclear Matrix Attachment Regions and Plant Gene Expression," *Trends Plant Sci* 3:91–96 (1998), which is hereby incorporated by reference in its entirety). It also makes interpreting results easier, as no backcross of plants is needed to separate different copies of the transgene in plants containing a single copy of the transgene, and only one backcross is needed for plants containing two copies of the transgene. The results of PCR analysis were verified by genomic blot analysis on a small percent of the plants.

Next, the physical location of Ds-containing T-DNA in anchor plant lines was determined. The chromosomal location of the Ds-T-DNA inserts in transgenic plants or cell lines is determined by using TAIL-PCR method or by the walking-adaptor method (Siebert et al., "An Improved PCR Method For Walking in Uncloned Genomic DNA," *Nucleic Acids Res.* 23: 1087–1088 (1995), which is hereby incorporated by reference in its entirety). The isolated flanking DNA fragments are sequenced and the sequence searched against the public *Arabidopsis* genome databases. By using either or both methods, it is expected that at least 80% of the flanking sequences to match known sequences in the *Arabidopsis* databases and thus define the chromosomal locations of each transgenic plant. By producing approximately 700 evenly spaced anchor lines, the average distance between sequential insertion sites in different plant lines is 200 kb because the *Arabidopsis* genome is 125,000 kb. Because up to 50% of anchor lines may be relatively inactive in transposition, only 350 actively transposing anchor lines are needed to generate the 50,000 insertion-mutant sublines, each of which contains the gene-trap and enhancer-trap feature when the plasmid shown in FIG. 10 is used, and the activation-trap feature when the plasmids shown in FIGS. 11A–B are used.

In a plasmid for generating activation-trap mutants, where both the TPase gene and Ds-containing segment are in the same plasmid, before transposition the transposase gene is already active in plants that harbor the plasmids such as that shown in FIGS. 11A and B. This is because each plasmid has a TPase gene under the control of a constitutive promoter 35S P. Therefore, transposition can occur. After transposition, the TPase gene is separated from 35S promoter and thus becomes inactive. In the event the TPase gene needs to be activated, one can treat plants with dexamethasone so that the Ac transposase gene driven by the glucocorticoid-inducible promoter (as in FIG. 11B) is activated to again initiate transposition. In plants transformed separately with a Ds plasmid or an Ac plasmid, T1 or T2 generation plants are crossed so that transposition can occur. Up to 4,000 germline transposants (sublines) can be generated from each 350 active anchor line. Transposants are readily recognized in sublines by selection with both Basta and hygromycin.

Example 10

Combined Gene-Trap and Enhancer-Trap Library

When the embodiment of the present invention is carried out in which a single plasmid contains both gene-trap and enhancer-trap features, the resultant gene-disruption library is equivalent to two randomly produced libraries, one with a gene-trap and one with an enhancer-trap. Thus, the method of the present invention that combines the gene-trap and enhancer-trap saves an enormous amount of time and labor in post-transposition analysis. An exemplary plasmid of this aspect of the present invention is shown in FIG. 10.

For simultaneously generating both a gene-trap and an enhancer-trap library, 4,000 transposants are generated from each 350 active anchor lines. This amounts to a total of approximately 1,400,000 transposants. This number of transposants represents a 14-fold redundancy over that of the 50,000 each of indexed, gene-trap and enhancer-trap mutant lines. The large redundancy is considered requisite for the following reasons. First, from the report of Parnov et al., "Analysis of Flanking Sequences From Dissociation Insertion Lines: A Database For Reverse Genetics in *Arabidopsis*, *Plant Cell* 11:2263–2270 (1999), which is hereby incorporated by reference in its entirety, there is a fourfold preference of insertion into the 5' ends of an *Arabidopsis* gene, which includes 500 bp before the initiation codon ATG, and 1,000 bp after the initiation codon. In fact, a preference of insertion into the 5' ends is of advantage for generating a gene-trap library, because disrupting the gene in this region will give the greatest chance of producing useful mutants (on the other hand, insertion near or beyond the 3' part of a gene is much less likely to produce useful mutants). Second, including several fold redundancy ensures the chance of including several useful allelic mutants for each indexed, mutant line. Third, since approximately 40% of the *Arabidopsis* genome is either intergenic or contains highly repetitive sequences, including the rDNA genes, insertion of the Ds element into these regions is not useful.

In this example, only 280 sublines out of 4,000 transposants are chosen, although other numbers may be selected. There are approximately 800 that transposed within 200 kb and serve as allelic mutant lines. The remaining 3,200 transposants transposed to a distance beyond 200 kb from either side of the specific anchor positions. Out of these transposants, perhaps several hundred may show a visible phenotype. When needed, these transposants are analyzed by determining the flanking sequence and placed on the chromosomal map, as described above. From the chromosomal location, it is known whether any transposant is already included in the indexed, mutant library. If not, the transposants represent additional sublines that will be further analyzed to determine the function of the corresponding disrupted gene.

Example 11

Activation-Trap Library

For producing an activation-trap library of 50,000 insertion mutants, 2,000 transposants need to be generated from each separate set of 330 anchor lines.

The transposition distance of each subline (each transposant) is determined by long PCR. In this example, the plasmid shown in FIG. 10 is used to transform *Arabidopsis*. The integrated plasmid in an anchor plant A2-3 (A2-3 means chromosome 2, and anchor line 3) is used as an example. For simplicity, some components of FIG. 10 are not shown, such as the 3' terminator. By using long PCR, segments of over 30 kb in length have been obtained (Barnes et al., "PCR Amplification of Up to 35-kb DNA with High Fidelity and High Yield from Lambda Bacteriophage Templates," *Proc. Natl. Acad. Sci. USA* 91:2216–2200 (1994), which is hereby incorporated by reference in its entirety). However, for *Arabidopsis*, a PCR product of up to 10 kb was generated so far.

The essential feature of the plasmid shown in FIG. 11 is similar to the activation-trap plasmid used by Weigel et al., "Activation Tagging in *Arabidopsis*," *Plant Physiol.* 122: 1003–1013 (2000), which is hereby incorporated by reference in its entirety.

Example 12

The Structure of Integrated Plasmid in Anchor Plants and Determining Transposition Distances Between 0–10 kb Using a Strategy Based on Long PCR Following transformation with a plasmid of the present invention that contains a transposition-specific sequence, a gene-trap, an enhancer trap, and a lox recombinase recognition sequence, the plasmid is integrated at some unknown site on the chromosome of anchor plant A. An exemplary anchor plant, A2-3 is shown in FIG. 24A, where "RA" is the right-side flanking sequence of anchor plant A2-3, and designates the "anchor position."

After the transposase is activated, either due to the crossing of plants each having a plasmid containing transposon-specific element with a plant or containing a transposase gene (as in the second embodiment of the present invention) or as a result of induction of the TPase by treatment with an inducer suitable to activate the inducible promoter driving the TPase gene, (as in the third embodiment of the present invention) the transposon-specific element (in this example the maize "Ds" dissociation element) jumps to a different site on the chromosome. As shown in FIG. 24B, this Ds element jumped approximately 10 kb from the anchor position to the right of anchor "RA", due to the transposition event, while maintaining the same orientation (3'Ds→5'Ds) as it had following transformation. FIG. 24B shows the transposition of the transposon element, bounded by the 3' and 5' ends. The distance from the anchor site to the transposition site is determined by long PCR, using template DNA from anchor plant A2-3, with the following primers: P1/RA/F, a forward primer based on the sequence of RA, and P2/3'Ds/F, a forward primer based on the sequence of 3' Ds. The location of the primers relative to the anchor site and the transposition site is shown in FIG. 24B. The expected PCR product in this plant is RA~3' Ds. The size of the PCR product is estimated after electrophoresis on an agarose gel by comparison with the mobility of DNA size markers. No hybridization is needed. The flanking sequence of 3'Ds after transposition is shown as "NS" in FIG. 24B. This sequence is determined by TAIL-PCR and is used later as the basis to designed a primer for the PCR reaction for subline walking, described in Example 8, below. In the event the DNA sequence around this anchor position is already in the DNA databank, there is no need to determine the NS sequence.

During the transposition event the transposon element may "flip" end-to-end, reinserting in the reverse, or inverse, orientation to that it had at the anchor site. FIG. 24C shows an inverse reinsertion of the Ds-containing element shown in FIG. 24A for anchor plant or cell A. Long PCR is used to determine the transposition distance from the anchor site, using primers P1/RA/F, a forward primer based on the sequence of RA, and P3/5' Ds/R, where P3 is the reverse primer based on the sequence of 5' Ds.

FIG. 24D shows a transposition to the left from the anchor site of the plasmid shown in FIG. 24A, in the direct orientation during reinsertion of Ds-containing segment. Primers for PCR are P4: P/5'Ds/F, and P5: P/Bar/R, where P4 is based on the known nucleotide sequence of 5' Ds, and Bar is based on the nucleotide sequence encoding resistance to.

FIG. 24E also shows a transposition to the left, and in the inverted orientation. PCR primers are: P2/3'Ds/R, and P5/Bar/R, based on the 3'Ds and the sequence of the Bar gene.

Thus, by using five different primers in four PCR reactions, all four transposition patterns can be distinguished. If the size of the PCR product is 10 kb or less, one expects to see a band whose size can be measured with an accuracy of ±0.5 kb. If the band is between 15 and 20 kb in size, it can be measured with an accuracy of ±1 kb.

In the present invention up to 4,000 transposants can be collected from each anchor plant or animal cell line that demonstrates occurrence of a transposition event. The transposition distance for the majority of the sublines can vary between 1 kb and over 2,000 kb (and some even transposed to another chromosome). During the first four sets of PCR reaction using primers P1 to P5, PCR products of up to 10 kb are measured. In other words, any sublines that transposed within 10 kb would be expected to give a band on the gel after the PCR step. Based on published information (Smith et al., "Characterization and Mapping of Ds-GUS-T-DNA Lines for Targeted Insertion," *Plant J.* 10: 721–732 (1996) and Machida et al., "Characterization of the Transposition Pattern of the Ac Element in *Arabidopsis Thaliana* Using Endonuclease I-SceI," *Proc. Natl. Acad. Sci. USA* 94:8675–8680 (1997), which are each hereby incorporated by reference in their entirety), it is estimated that approximately 1% of the transposants may transpose within 10 kb from the anchor position. Thus, 40 positive samples out of 4,000 samples can be expected.

By pooling 50 samples, both horizontally and vertically as follows, leaves from 2,500 transposants can be made into 50 pools and can be handled at once. Genomic DNA can be isolated from each of the 50 pools and PCR can be carried out from which results can be obtained within a day. Out of each pool of 50 samples, one positive reaction may be expected (i.e., a band will be seen after gel electrophoresis). The single positive plant is then tested again by PCR to confirm the result and to estimate the size of the band. Thus, the transposition distance can be determined. In this example, from anchor plant (or cell line) A2-3, one can select sublines A2-3-1R to represent 3 kb transposition to the right side of the anchor, A2-3-2R to represent 6 kb to the right side of the anchor, and so on. Similarly, A2-3-1L represents a 3 kb transposition to the left side of the anchor position, and so on. All these samples are chosen based on direct orientation during re-insertion and thus represent gene-trap samples. Similarly, a same number of samples may be expected based on inverted orientation during reinsertion and represent enhancer-trap samples. They are designated as A2-3-1RE, A2-3-2RE, etc. Note that these 16 sublines are all different. By naming it A2-3-1R, it means that the transposition distance is approximately 3 kb (it can be any distance between 2.5 and 3.5 kb).

The reason for generating 2,000 transposants from each anchor line is to provide a threefold safety factor in finding the transposants every 3 kb (±1 kb) to satisfy our need for producing an indexed insertion-mutant library.

Example 13

Determining Transposition Distance Between 10 and 20 kb from Anchor Site

Subline walking is used to determine distances of plasmids that are transposed between 10 and 20 kb from anchor position. FIG. 25 illustrates this process. Note that the integrated plasmid structure is further simplified for this illustration. The 3' Ds flanking sequence "NS" is determined as described above, using TAIL-PCR. This sequence is then used to design primer 6 ("P6"), for use as a forward primer P6/NS/F, along with primer 2: P2/3' Ds/F, to carry out long PCR on this transgenic plant to determine the distance between NS and the Ds element. In the example shown in FIG. 25, the expected PCR product is NS~3' Ds. The size of this product is determined as described above, using long PCR.

Thus, the chromosomal position of different sublines can be defined. For example, A2-3-5R is transposed to approximately 13 kb on the right side of the anchor (or 3 kb from NS), A2-3-6R to 16 kb from anchor, A2-3-7R to 19 kb from anchor and A2-3-7R to 22 kb from anchor position. Similarly, sublines can be designated as A2-3-5RE, A2-3-5L and A2-3-5LE, etc.

By 18 additional steps of subline walking, a distance of 200 kb from the anchor position can be reached. Since transposition can occur to both the left side and the right side of the anchor position, a total of 20 steps can cover a distance of 400 kb. In fact, from any anchor position, a much longer distance can be reached with additional steps of subline walking. This may be needed in some cases to overlap the transposant from the adjacent anchor.

Example 14

Potential Blockade and Ways to Jump Over it

When subline walking reaches long stretches of repetitive DNA sequences greater than 10 kb, it may be difficult to continue the walking process (unless long PCR as applied to genomic DNA can reach 20 or 30 kb). When a blockade is reached, two things can be done. First, if the genome sequence in this region is already known, primers can be designed approximately 10, 20, or 30 kb away from the point of blockage based on the known DNA sequence, and subline walking is resumed from beyond the blockade. If the genomic sequence is not known, genomic DNA can be "cut" at the rare enzyme sites, such as IppoI (same as E1 in FIG. 10), which is a part of all Ds-containing plasmids by design. Since an IppoI sequence is present in two locations in the integrated plasmid (but not in the genome of *Arabidopsis*, except in the ribosomal RNA gene), after digestion, followed by agarose gel electrophoresis, the size of the DNA can be measured accurately up to 40 kb by regular gel electrophoresis, or up to 800 kb by pulse-field electrophoresis, to determine the size of longer stretches of repetitive DNA sequences. Then, PCR-based subline walking can proceed by using a primer beyond the distal end of this repetitive DNA stretch.

Example 15

Use of the Cre-lox System to Delete a DNA Segment of any Size in Vivo

The Cre-lox-based method can delete a segment of up to 400 kb from any one of the plants in the indexed, insertion-mutant library of the present invention.

FIGS. 9A–B show the use of a Cre-lox system to delete a DNA segment from the genome of a transposant using a Cre-lox containing plasmid of the present invention. The wavy lines depict chromosomal DNA (fragments "a" and "b") of the *Arabidopsis* plant transformed with such a plasmid. FIG. 9A shows the integrated version of the plant-specific activation-tagging plasmid shown in FIG. 11B (in an abbreviated form for simplicity of illustration), with TPase under the control of the glucocorticoid inducible promoter GIP, and the Cre recombinase gene under the control of the estradiol-activated inducible promoter EIP. The transformation plasmid is prepared with one of the two requisite lox sites located inside the boundaries of the transposon-specific element, and the second lox site located outside the transposon. Hosts are transformed with the plasmid shown in FIG. 11B, using transformation methods as described herein. Transgene copy number is determined by PCR using the CN sequence, and the anchor site within the chromosome is determined as described above. Transformants are selected that have one copy of the transgene, and, in the case of plants, regenerated using well-known procedures. The transformed anchor plant included a self-activating TPase, and it catalyzes transposition. In FIG. 9B, reintegration occurs to the right of its transformation anchor position in the chromosome, between chromosomal fragments "b" and "c."

The plant is then treated with estradiol, thereby activating the Cre recombinase gene. A molecule of the Cre enzyme moves to the lox sites, binding to the inverted repeats of the two lox sites, splicing each lox sequence in half, excising the intervening nucleic acid segment including the genomic fragment b and a portion of the original plasmid, as shown in FIGS. 26A–B. Cre then splices together, i.e., recombines, the remaining halves of the two lox sites, shown in the left side structure in FIG. 26A or FIG. 26B. The excised fragment b, is degraded by cellular nucleases. In this process, the Cre-lox system allows the deletion at will of any DNA fragment of any size, from any known location of the *Arabidopsis* genome as long as that DNA fragment is located between two lox sites of the same orientation. For example, in FIGS. 9B and 26B, if the two lox sites in the integrated plasmid after transposition are 15 kb apart, a 15 kb fragment at this precise location can be deleted in vivo (fragment b shown in FIG. 26B) after activating the Cre recombinase with the appropriate inducing agent. If the resulting transgenic plant shows a phenotype that is different from that exhibited by the plant before this deletion process, it suggests that within this 15 kb fragment there is a gene (or several genes) that may be responsible for the observed phenotype. Thus, this type of plasmid is useful for future use in determining the function of genes from a library produced by the methods of the present invention.

Example 16

Utilization of the lox-Site-Containing Sequence in the T-DNA Integrated in the Transgenic Plant or Cell The Cre-lox system can be used to put back a wild-type gene that corresponds to the disrupted gene for future use in a gain-of-function test to confirm the proposed function of a gene of interest. The utilization of the lox-site containing sequence in the T-DNA integrated in the transgenic plant is shown in FIGS. 27A–E. FIG. 27A shows a portion of an exemplary transposon recognition sequence-containing plasmid of the present invention. This plasmid, suitable for plant transformation, has a maize Ds element, with a first selection marker, the Bar gene for resistance to the herbicide phosphinothricin ("PPT") after transposition (FIG. 27C). To the right of the 3' boundary of the transposon recognition sequence; and inserted between the 3' and 5' ends of the transposon recognition sequence are a second selection marker, Hpt, which confers antibiotic resistance to hygromycin to transformants during the initial transformation event; a visible marker, the Gus gene; a cluster of restriction endonuclease recognition sites, abbreviated here as "E1;" and a lox site. Beyond the 5' end of the Ds element is an *Arabidopsis* actin 2 promoter, "A2P". Note that for simplicity of presentation, 3' terminators are not included in this plasmid. This plasmid is transformed into an appropriate host plant, for example, *Arabidopsis*, using a *Agrobacterium*-mediated transformation (Krysan et al., "T-DNA As an Insertional Mutagen in *Arabidopsis*," *Plant Cell* 11: 2283–2290 (1999), which is hereby incorporated by reference in its entirety). FIG. 27B shows the *Arabidopsis* genome after the transformation plasmid is integrated into the plant genome of an exemplary plant. The wavy lines represent plant DNA flanking the insertion site of the transformation plasmid.

Selection of transformed plants is made by growing transformed plants in hygromycin. Plants are then screened by PCR for transgene copy number, using primers based on the sequence of the endogenous "CN" sequence which is also included in the transformation plasmid, although not shown in FIGS. 27A–E. Plants with one copy number are chosen for further analysis.

The anchor position of the Ds element is determined using TAIL-PCR, where one primer based on the known sequence of the Ds element (either 3' or 5', or both) and the second primer is a shorter arbitrary degenerate primer designed to sequence the DNA adjacent to the known DNA segments of the transposon element, moving from the known sequence flanking of the transposon outward into the adjacent chromosomal sequence. Once the anchor site has been identified, transposition is then effected in the anchor plant. This can be carried out in accordance with either any embodiments of the present invention. The first embodiment includes crossing the Ds-containing plant with a TPase-containing plant; the second embodiment involves activating an inducible TPase-containing plasmid that was co-transformed into the plant with the Ds-containing plasmid. If the third embodiment was used, the Ds-containing plasmid shown in FIG. 27A also included a TPase-encoding nucleic acid molecule, under the control of either a constitutive or an inducible promoter.

The structure of the exemplary anchor plant following the transposition event is shown in FIG. 27C. The transposon element has jumped to the right of its anchor position, to a site on the plant genome between chromosomal elements "b" and "c." The flanking sequences of 3'Ds and 5' Ds in the plant are determined using TAIL-PCR as described above, moving outward into the genomic sequence from the flanking Ds boundaries. A comparison of the nucleotide sequence on each side with the genomic database for *Arabidopsis* will indicate the chromosomal segment to which the Ds element has transposed. In FIG. 27D, the site of transposition is shown as the segment of the plant chromosome containing gene "Y," which has been disrupted by the transposition of the Ds-containing part of the integrated T-DNA into this gene to produce Y1 and Y2. The plant line carrying the disrupted "Y" gene is propagated, and observed for mutant phenotype. To confirm the function of gene Y, a gain-of-function experiment is carried out by putting back an intact Y gene. This can be achieved by using seeds from this plant to produce calli. The nucleic acid sequence of "Y" is prepared and used to insert into a Cre-lox containing plasmid. The nucleic acid for "Y" can be prepared from the organism itself, using well-known DNA isolation and recombinant DNA technology, or can be synthesized using any automated DNA synthesizing machine, and then inserted into a Cre-lox-containing gene-disruption transformation plasmid, shown in FIG. 27E, using well known molecular cloning techniques as described in Sambrook et al., Molecular Cloning: A Laboratory Manual, Second Edition, Cold Spring Harbor Press, NY (1989), which is hereby incorporated by reference in its entirety.

The calli of the propagated transposant plant are then transformed by the biolistic method with a circular plasmid such as that shown in FIG. 27E, by joining the two ends, where BS is the pBluescript vector (Stratagene, La Jolla, Calif.), EIP is an estrogen-inducible promoter (Zuo et al., "Chemical-Inducible Systems for Regulated Expression of Plant Genes," Current Opin. Biotech. 11: 146–151 (2000), which is hereby incorporated by reference in its entirety), Cre is the Cre recombinase gene (Ow, D. W., "Recombinase-Directed Chromosome Engineering in Plants," Curr. Opin. Biotech. 7:181–186 (1996), which is hereby incorporated by reference in its entirety), and Y is the nucleic acid molecule encoding the gene that is to replace the interrupted "Y" gene. Other vectors, promoters, and nucleic acid molecules, including, but not limited to, those described above, are suitable for the preparation of the gene-disruption plasmid for this aspect of the present invention.

Transgenic plants are regenerated and the presence of the Cre-containing plasmid confirmed by PCR. The transgenic plant is then induced with the promoter-inducing agent allowing for the expression of the Cre recombinase. Expression of the Cre recombinase catalyzes the "gene switch" reaction by binding to the lox sites in the integrated T-DNA, which has undergone transposition, to give the structure shown in FIG. 27F. The presence of an intact Y (which includes its promoter and terminator) in re-transformed exemplary plant "A2-3-7A" would restore the mutant phenotype. When estradiol is removed from the system, further Cre-mediated reaction is prevented. Thus, if a gain of function (i.e., reversing the mutant phenotype) is observed, it confirms that the disrupted gene Y in A2-3-7A is responsible for a given phenotype.

The present invention can be applied to a number of crop plants, such as rice and tobacco. As a side benefit, another utility of the Cre-lox system is for future use to introduce and overexpress other useful genes in the lox site of the integrated T-DNA to produce valuable products. It is known that in different chromosomal locations, the level transcription activity varies. Transcription in some locations is much more active and these positions are revealed by the levels of gfp or GUS activity (based on visible marker genes built into several of the Ds plasmids) in different transgenic plants. By introducing a gene of interest into transgenic plants (such as rice or tobacco) via the Cre-lox feature, plants with a high level of transcriptional activity can be made to produce large amounts of a commercially valuable product.

Example 17

Use of Mouse Stem Cell Systems to Produce an Insertion-Mutant Library by Combining with a Transposon System The poly A-trap approach can also be combined with the method of the second and third embodiments of the present invention, which use plasmids that contain transposable elements, to produce a saturation, indexed, gene-disruption library, for example, in mouse cells. The reason for using this combined approach is that the mouse genome is very large, approximately $3.0 \times 10^6$ kb. Thus, the production of a saturation, indexed, insertion-mutant library of mouse with an insertion of the input plasmid every 6 kb would require close to one million mutant mice for 95% probability of covering the entire genome. For a randomly produced mutant library, the number is even higher. The labor and cost of producing a saturation, insertion-mutant library of mouse would be tremendous. Because mouse probably contains up to 60,000 genes, a good alternative is to transform mouse embryonic stem (ES) cells to produce up to 60,000 poly A-trapped insertion-mutant ES cell clones, each representing an expressed gene, to include most of the expressed genes in mouse. These cell clones can be tested in different ways, for example, as to their response to specific chemicals (including drugs and hormones), or physical stress (such as UV radiation or high temperature). Those ES cell clones that gave positive and potentially interesting responses to any of the above mentioned treatments can then be introduced into cells in mouse embryos and generate live animals by using the procedure of Salminen et al., "Efficient Poly A Trap Approach Allows the Capture of Genes Specifically Active in Differentiated Embryonic Stem Cell and in Mouse Embryos," *Develop. Dynamics* 212:328–333 (1998), which is hereby incorporated by reference in its entirety).

It would be too time consuming to introduce a specific plasmid individually into an extremely large number of mouse ES cells with the probability of producing over one million potentially useful cell clones in order to obtain 60,000 poly A-tagged cell clones. Therefore, by combining the poly A-trap approach with a transposon system, only a relatively small number of anchor ES cell clones need to be generated. After activation of the transposase gene in the integrated plasmid in these anchor cell clones, transposition allows many more cells clones (transposants) to be produced from each anchor ES cell clone to trap most of the expressed genes in mouse.

Note that the same type of analysis as shown in Example 6 through Example 17 can be carried out in plants, animals, or cells, once they are tagged with a polyA-trap-transposon system of choice, to assess and define the indexed, saturation, insertion-mutant library produced using the poly A-trap-containing plasmid. In plants such as rice it is possible to use haploid cells for transformation and to regenerate a library of polyA-tagged plants. These haploid plants have the advantage that it would be much more likely to detect a phenotype change since in diploid plants one copy of the chromosome is not mutated and may be sufficient to give normal phenotypes.

The present invention teaches a strategy to construct indexed, saturation, insertion-mutant libraries of any plant or animal genome This method starts with transferring a suitable transposon (see Table 2) into a heterologous plant or animal, or cell therefrom, to produce a number of evenly-spaced anchor lines. Next, large numbers of secondary insertion-mutant sublines (transposants) are derived from each anchor line as a result of transposon-based transposition. All approaches using this principle prior to the present invention have been based on the random (shotgun-type) approach. For *Arabidopsis*, the average gene density in gene-rich regions is approximately 3 kb. To achieve a 99% probability of tagging all the *Arabidopsis* genes, approximately 230,000 randomly tagged lines are needed based on statistical calculation and assuming that insertion of the transposon into the chromosome is random (Krysan et al., "T-DNA As An Insertional Mutagen In *Arabidopsis*," *Plant Cell* 11:2283–2290 (1999), which is hereby incorporated by reference in its entirety). It is known that a significant amount of time and effort are required, in several stages, in order to analyze large numbers of redundant transposon lines in mutant populations generated via any random approach. Even with such a large population, investigators do not know what percent of the genome is actually tagged since transposition is not entirely random. In contrast, the systematic method of the present invention allows one to produce an indexed, insertion-mutant library that covers the entire genome, and redundant lines are eliminated in an earlier stage of analysis to save time and effort in analyzing many redundant samples in different steps, including growing up large numbers of plants. Moreover, in the method of the present invention, if a specific region is not covered with the transposon even with a calculated tenfold coverage of the genome, it is known where this region is located and it can be concluded that there are probably no genes in this region. It is known that in transgenic Ds/Ac *Arabidopsis* plants, 30% of transpositions occur within 300 kb from either side of the anchor position (Smith et al., "Characterization and Mapping of Ds-GUS-T-DNA Lines for Targeted Insertion," *Plant J.* 10: 721–732 (1996); Machida et al., "Characterization of the Transposition Pattern of the Ac Element in *Arabidopsis thaliana* Using Endonuclease I-SceI," *Proc. Natl. Acad. Sci. USA* 94:8675–8680 (1997); Parnov et al., "Analysis of Flanking Sequences From Dissociation Insertion Lines: A Database For Reverse Genetics in *Arabidopsis*, *Plant Cell* 11:2263–2270 (1999), which are hereby incorporated by reference in their entirety).

The maize Ac/Ds system was improved by using enhancer- and/or gene-trap plasmids (Sundaresan et al., "Patterns of Gene Action In Plant Development Revealed by Enhancer Trap and Gene Trap Transposable Elements," *Genes &Develop.* 9:1797–1810 (1995); Ramachandran et al, "Transposons As Tools For Functional Genomics," *Plant Physiol. Biochem.* 39:243–252 (2001), which are hereby incorporated by reference in their entirety). After transposition, gene-trapped transgenic plants detect many disrupted genes that have no mutant phenotype by expression of reporter genes (such as uidA and gfp), whereas the enhancer-trap plasmid detects the presence of endogenous enhancers. More recently, activation-trap plasmids have been used (Weigel et al., "Activation Tagging in *Arabidopsis*," *Plant Physiol.* 122:1003–1013 (2000), which is hereby incorporated by the reference in its entirety).

Activation-trap plasmids include strong enhancers to amplify the expression of an endogenous gene at or near insertion sites. It is known that a large percent of the genes in eukaryotic organisms are functionally redundant. Plants in the activation-tagging library, which shows gain-of-function phenotypes, can detect the function of genes when they are redundant in the genome. Many genes can be potentially activated once the activation-trap based insertion-mutant library is constructed. Thus, it is not necessary to transfer each gene separately via the time-consuming transformation procedure.

Here, different superior plasmids were constructed. For example, one of them can be used to generate mutant lines that include both the gene-trap and enhancer-trap features. Another plasmid can be used to generate an activation-trap based mutant line. In both of these plasmids, the transposase gene is included but regulated so that there is no need to cross a Ds anchor line with an Ac line. Moreover, a major advantage of these Ac/Ds-based insertion-mutant libraries is that the revertants, which allow verification of gene sequence function correlation, can be obtained and identified relatively easily (Martienssen, R., "Functional Genomics: Probing Plant Gene Function and Expression With Transposons," *Proc. Natl. Acad. Sci. USA* 88:4260–4264 (1998), which is hereby incorporated by reference in its entirety).

For functional analysis, in the future, in general, the percent of visible changes in phenotype in different *Arabidopsis* mutant plant lines amounts to less than 10% of the total population. However, this percentage presumably can be significantly increased by subjecting the mutant lines to different biotic and abiotic stresses, which can also be applied to transformed cells. Thus, to maximize the probability of success for future screening of this mutant library, it is desirable to produce all four types of insertion libraries: a gene-trap, an enhancer-trap, an activation-trap, and a polyA-trap mutant library. These libraries can accelerate the discovery of many thousands of genes from any given organism. However, the subject of this invention is limited to the description of a novel method to produce indexed, saturation, insertion-mutant libraries. These libraries will make future analysis of gene function much easier and faster than using any of the currently available, randomly-generated mutant libraries.

For example, for *Arabidopsis*, by using the published, random methods, the total number of insertion-mutant lines in the first three types of libraries would be 3×230,000=690,000 lines. Even though, in principle, with these randomly produced insertion-mutant libraries, one could find out the chromosomal location of the 690,000 *Arabidopsis* mutant lines by determining the flanking sequence of each mutant; however, it would require a tremendous amount of effort and time. On the other hand, for larger genomes such as rice, the total number required would be 3×660,000=1,980,000 lines, which is simply not practical to determine the flanking sequence of each of these mutant lines. For maize, the number required would be close to eight million lines.

Not only is the determination of the chromosomal location of a very large number of transposants by analyzing the flanking sequence extremely time consuming, but a sizable percent of the samples are not likely to give results. This is because in most eukaryotic organisms the percentage of repetitive DNA sequences, including endogenous transposons, in the genome is high. For example, over 40% in rice and in the human genome consist of repetitive sequences that are present in at least ten copies for each type of repetitive sequence. Therefore, when transposants are located in or near any repetitive sequence, the location of the transposants cannot be assigned.

On the contrary, by using the systematic method of the present invention, only two indexed, insertion-mutant libraries need be generated. For *Arabidopsis*, one library of 50,000 lines represents both a gene-trap and an enhancer-trap plant (or cell line) within the same population. The second library of 50,000 lines represents the activation-trap population. Equally important is the fact that by using the systematic approach of the present invention, the chromosomal location of only a small number of anchor lines and mutant sublines need to be determined by analyzing the flanking sequence, which amounts to less than 8,000 for *Arabidopsis*. Thus, a great deal of time and effort can be saved using the plasmids and methods taught herein.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of constructing a non-redundant, indexed, saturation, gene-disruption plant library comprising:
   providing a plasmid having:
      two identical clusters of unique enzyme-cutting sites and a dissociation element having two ends;
   transforming a plurality of plants with the plasmid to produce a plurality of transformed plants with the plasmid integrated at different locations within the genome of the plants;
   mapping the locations of the integrated plasmid in the transgenic plants to identify anchor transgenic plant lines each having the integrated plasmid within its genome at a location from about 200 to about 600 kilobases away from the location of an integrated plasmid in any other anchor transgenic line;
   obtaining homozygous transgenic anchor plant lines;
   crossing each of the homozygous anchor transgenic plant lines with a plant having an activator element to form progeny plants, wherein said crossing activates transposition of a portion of the plasmid bounded by the two ends of the dissociation element to form a plurality of progeny plants having different genes disrupted;
   selecting progeny plants having the activator element segregated out;
   digesting the plant genome at different unique enzyme-cutting sites to release a DNA fragment produced by digestion of the unique enzyme-cutting sites from each of the transgenic progeny plants, wherein said digesting is carried out by serial, separate use of a plurality of restriction enzymes, specific to one of the unique enzyme-cutting sites;
   measuring the size of each of the released DNA fragments to determine transposition distances in each of the transgenic progeny plants; and
   selecting the progeny transgenic plants with the transposition distances which are different from the transposition distances of the other progeny transgenic plants by a pre-determined amount to prepare a non-redundant, indexed, saturation, gene-disruption plant library.

2. A method according to claim 1 further comprising:
   sequencing regions flanking the integrated plasmid in selected progeny plants of the non-redundant, indexed, saturation, gene-disruption plant library to mark the disrupted genes.

3. A method according to claim 1 further comprising:
   observing the phenotype of the plants of the non-redundant, indexed, saturation, gene-disruption plant library having disrupted genes;
   comparing the phenotype of plants having disrupted genes to plants not having disrupted genes; and
   correlating the phenotype difference with the disrupted genes.

4. A method according to claim 1, wherein said digesting is carried out until the gene fragment is less than 30 kilobases.

5. A method according to claim 1, wherein the plasmid has an insert, wherein the insert comprises:
   the dissociation element having two ends and the two identical clusters of unique enzyme-cutting sites, wherein 1 cluster of unique enzyme-cutting sites is between the two ends of the dissociation element in the insert and the other cluster of unique enzyme-cutting sites is not between the two ends of the dissociation element in the insert.

6. A method according to claim 1, wherein the dissociation element is a maize dissociation element.

7. A method according to claim 1, wherein the identical clusters of unique enzyme-cutting sites are formed from 2 or more adjacent enzyme-cutting sites selected from the group consisting of I-PpoI, CeuI, AscI, NotI, PmeI, ApaI, BglI, SmaI, SalI, XhoI, and EcoRI.

8. A plasmid having an insert, wherein the insert comprises:
   a dissociation element having two ends and
   two identical clusters of unique enzyme-cutting sites, wherein 1 cluster of unique enzyme-cutting sites is between the two ends of the dissociation element in the insert and the other cluster of unique enzyme-cutting sites is not between the two ends of the dissociation element in the insert.

9. A plasmid according to claim 8, wherein the dissociation element is a maize dissociation element.

10. A plasmid according to claim 8, wherein the identical clusters of unique enzyme-cutting sites are formed from 2 or more contiguous enzyme-cutting sites selected from the group consisting of I-PpoI, CeuI, AscI, NotI, PmeI, ApaI, BglI, SmaI, SalI, XhoI, and EcoRI.

11. A plant transformed with the plasmid according to claim 8.

12. A plant according to claim 11, wherein the dissociation element is a maize dissociation element.

13. A plant according to claim 11, wherein the identical clusters of unique enzyme-cutting sites are formed from 2 or more contiguous enzyme-cutting sites selected from the group consisting of I-PpoI, CeuI, AscI, NotI, PmeI, ApaI, BglI, SmaI, SalI, XhoI, and EcoRI.

14. A plant resulting from crossing a homozygous anchor plant derived from the plant according to claim 11 with a plant having an activator element.

15. A plant according to claim 14, wherein the dissociation element is a maize dissociation element.

16. A plant according to claim 14, wherein the identical clusters of unique enzyme-cutting sites are formed from 2 or more contiguous enzyme-cutting sites selected from the group consisting of I-PpoI, CeuI, AscI, NotI, PmeI, ApaI, BglI, SmaI, SalI, XhoI, and EcoRI.

17. A progeny plant, comprising said plasmid, produced from the plant according to claim 14.

18. A progeny plant according to claim 17, wherein the dissociation element is a maize dissociation element.

19. A progeny plant according to claim 17, wherein the identical clusters of unique enzyme-cutting sites are formed from 2 or more contiguous enzyme-cutting sites selected from the group consisting of I-PpoI, CeuI, AscI, NotI, PmeI, ApaI, BglI, SmaI, SalI, XhoI, and EcoRI.

20. A method of constructing a non-redundant, indexed, saturation, gene-disruption genomic library of a plant comprising:
   providing a first plasmid comprising:
      a transposon-specific recognition sequence having 5' and 3' ends which form boundaries of the transposon-specific recognition sequence;
      2 identical clusters of restriction enzyme recognition sites,
   wherein one cluster is located inside the boundaries of the transposon-specific recognition sequence and a second cluster is located outside the boundaries of the transposon-specific recognition sequence, and wherein the enzyme recognition sites in one cluster are identical to the enzyme recognition sites in the second cluster but the enzyme recognition sites in both clusters either do not exist or are rare in the plant in which the library is being constructed;
      one or more genes operably linked to one or more constitutive promoter elements in the plasmid;
      one or more 3' terminator elements operably linked 3' to each gene in the plasmid;
      one or more first selection marker genes located inside the boundaries of the transposon recognition sequence and operably linked to a promoter element and a 3' terminator element;
      one or more detection genes, wherein at least one of the one or more detection genes is located inside the boundaries of the transposon recognition sequence and is operably linked to a promoter element and a 3' terminator element;
   providing a second plasmid comprising:
      a transposase gene operably linked to at least one inducible promoter element and a 3' terminator element;
      one or more second selection marker genes operably linked to a promoter element and a 3' terminator element wherein the first selection marker gene is different from the second selection marker gene;
   co-transforming a plurality of plants with the first and second plasmids to produce a plurality of co-transformed anchor transgenic plants having the first and second plasmids integrated at different sites within the transgenic plants' genome, wherein the integration site of a plasmid due to transformation is defined as a plasmid's anchor location;
   selecting a plurality of anchor transgenic plants having one copy of the first and second plasmid integrated into the genome;
   mapping an anchor location for each integrated first plasmid in the plurality of transgenic plants to identify anchor transgenic lines, wherein each identified anchor transgenic line harbors a first plasmid within its genome at a location from about 200 to about 600 kilobases away from the location of a first plasmid in the other anchor transgenic lines;
   allowing transposition to occur to produce a plurality of transposants having different genes disrupted, wherein the transposon-specific recognition sequence of the first plasmid has transposed from its anchor location to a different reintegration location in the transposant's genome, thereby defining a transposition distance between the anchor location and the reintegration location;
   determining transposition distances of the transposed transposon-specific recognition sequence in a plurality of transposants in a given anchor line; and
   selecting a plurality of transposants wherein each transposant has a transposition distance that is different from transposition distances of the other transposants to prepare a non-redundant, indexed, saturation, gene disruption library.

21. The method according to claim 20, wherein the mapping an anchor location comprises:
   identifying nucleotide sequences flanking an integrated first plasmid in an anchor transgenic line;
   comparing the identified flanking sequences with genomic sequences in a public DNA database; and
   determining a physical location of the integrated first plasmid within the anchor transgenic line's genome.

22. The method according to claim 20, wherein said determining transposition distances comprises:
   measuring transposition distances of a plurality of transposants by carrying out long PCR in a stepwise manner which comprises using a first pair of specific primers, wherein one primer is based on nucleotide sequences flanking the integrated first plasmid in a given anchor line and a second primer is based on either end of the transposed transposon-specific recognition sequence;
   identifying the individual transposant from among the plurality of transposants that has the greatest transposition distance measurable by long PCR with the first pair of specific primers; and
   determining nucleotide sequences flanking the transposon-specific recognition sequence identified as having the greatest transposition distance measurable using the first pair of specific primers.

23. The method according to claim 22 further comprising:
   measuring transposition distances of a plurality of additional transposants by carrying out long PCR using a second pair of specific primers, wherein one primer is based on nucleotide sequences flanking the transposed transposon-specific recognition sequence measurable by the first pair of long PCR primers and a second primer is based on either end of the transposon-specific recognition sequence;
   identifying the individual transposants that have the greatest transposition distance capable of being measured with the second pair of specific primers; and
   determining nucleotide sequences flanking the transposon-specific recognition sequence in the individual transposant identified as having the greatest transposition distance measurable using the second pair of specific primers.

24. The method according to claim 23 further comprising:
   carrying out long PCR in a plurality of additional transposants in a stepwise manner until 200–600 kilobases flanking a given anchor location within the genome have been determined, wherein each long PCR step comprises:

designing a successive specific pair of primers, wherein one primer is based on a flanking nucleotide sequence of the transposed transposition-specific recognition sequence having a transposition distance measurable using the previous pair of specific primers, and a second primer is based on either end of the transposition-specific recognition sequence;

measuring additional transposition distances of a plurality of selected transposants by carrying out long PCR using the successive pair of specific primers;

identifying the individual transposants that have the greatest transposition distance capable of being measured with the pair of specific primers; and determining nucleotide sequences flanking the transposon-specific recognition sequence identified as having the greatest transposition distance measurable using the successive pair of specific primers.

25. The method according to claim 20, wherein said selecting results in a non-redundant, indexed, saturation, gene disruption library having a plurality of transposants, wherein each transposant has a transposition distance that is different from the transposition distances of the other transposants by between 3 and 6 kilobases.

26. A method according to claim 20, wherein the second plasmid further comprises a TMAR sequence located near the promoter element linked to the transposase gene.

27. A method according to claim 20, wherein the transposon-recognition sequence is from the maize Ds/Ac transposon system.

28. A method according to claim 20, wherein the transposase gene is from the maize Ds/Ac transposon system.

29. A method according to claim 20, wherein the cluster of rare enzyme recognition sites is formed from 2 or more adjacent enzyme recognition sites selected from the group consisting of I-PpoI, CeuI, AscI, NotI, PmeI, ApaI, BglI, and SmaI.

30. A method according to claim 20, wherein the constitutive promoter is selected from the group consisting of Ap 3, CaMV 35 S, *Agrobacterium* plasmid promoter 1', *Agrobacterium* plasmid promoter 2', rice actin1, maize ubiquitin promoter, rice actin4, and CMV.

31. A method according to claim 20, wherein the inducible promoter is selected from the group consisting of a heat shock 70 promoter, a glucocorticoid inducible promoter, an estrogen inducible promoter, and a salicylic acid-inducible promoter.

32. A method according to claim 20, wherein the first or second selection marker is selected from the group consisting of Hpt, Bar, IAAH, Cah, Amp, Puro, and Neo.

33. A method according to claim 20, wherein the detection marker is selected from the group consisting of green fluorescent protein, GUS, and LacZ.

34. A method according to claim 20 further comprising:
inducing expression of the transposase gene in the second plasmid following said co-transforming, wherein said inducing activates the transposition of a portion of the first plasmid bounded by the 5' and 3' ends of the transposon-recognition sequence forming a plurality of transposant plants having different genes disrupted.

35. A method according to claim 20, wherein the plant is selected from the group consisting of monocots and dicots.

36. A method according to claim 35, wherein the plant is a monocot.

37. A method according to claim 35, wherein the plant is dicot.

38. The method according to claim 1, wherein the predetermined amount is from about 2 kb to about 10 kb.

39. The method according to claim 1, wherein the predetermined amount is from about 10 kb to about 20 kb.

40. The method according to claim 1, wherein the predetermined amount is greater than 20 kb.

* * * * *